(12) United States Patent
Kopchick

(10) Patent No.: US 7,060,437 B1
(45) Date of Patent: Jun. 13, 2006

(54) GROWTH HORMONE-REGULATABLE BROWN ADIPOSE TISSUE GENES AND PROTEINS AND USES THEREOF

(75) Inventor: John Joseph Kopchick, Athens, OH (US)

(73) Assignee: Ohio University, Athens, OH (US)

( * ) Notice: Subject to any disclaimer, the term of this patent is extended or adjusted under 35 U.S.C. 154(b) by 0 days.

(21) Appl. No.: 09/959,714

(22) PCT Filed: May 5, 2000

(86) PCT No.: PCT/US00/12145

§ 371 (c)(1),
(2), (4) Date: Mar. 19, 2002

(87) PCT Pub. No.: WO00/66784

PCT Pub. Date: Nov. 9, 2000

Related U.S. Application Data

(60) Provisional application No. 60/132,670, filed on May 5, 1999.

(51) Int. Cl.
*C12Q 1/68* (2006.01)
*C07H 21/02* (2006.01)
*C07H 21/04* (2006.01)

(52) U.S. Cl. .................. 435/6; 536/23.1; 536/24.3
(58) Field of Classification Search .................. 435/6; 536/23.1, 24.3
See application file for complete search history.

(56) References Cited

U.S. PATENT DOCUMENTS 5,350,836 A  9/1994 Kopchick et al.

FOREIGN PATENT DOCUMENTS

EP  0158973  4/1985

OTHER PUBLICATIONS

Adan et al., *Diagnostic Markers of Permanent Idiopathic Growth Hormone Deficiency*, Journal of Clinical Endocrinology and Metabolism, vol. 78, No. 2, pp. 353-358, 1994.
Alexander et al., *The effect of social stress on adrenal axis activity in horses: the importance of monitoring corticosteroid-binding globulin capacity*, Journal of Endocrinology, No. 157, pp. 425-432.
Banine et al., *Positive and negative elements modulate the promotor of the human liver-specific 2-HS-glycoprotein gene*, Eur. J. Biochem, No. 267, pp. 1214-1222, Feb. 2000.
Braun et al., *A novel human muscle factor related to but distinct from MyoD1 induces myogenic conversion in 10T1/2 fibroblasts*, The EMBO Journal, vol. 8, No. 3, pp. 701-709, 1989.

Chan et al., *Molecular Cloning and Localization to Chromosome 6 of Mouse INT1L1 Gene*, Somatic Cell and Molecular genetics, vol. 15, No. 6, pp. 555-562, 1989.
Cousin et al, *Occurence of brown adipocytes in rat white adipose tissue: molecular and morphological characterization*, Journal of Cell Science, vol. 103, pp. 931-942, 1992.
Costa et al., *Transgenic rabbits overexpressing growth hormone develop acromegaly and diabetes mellitus*, The FASEB Journal, vol. 12, pp. 1455-1460, Nov. 1998.
Dantoine et al, *Decrease of Serum Paraoxonase Activity in Chronic Renal Failure*, Journal of the American Society of Nephrology 9, pp. 2082-2088, Nov. 1998.
Galizzi et al, *Molecular cloning of a cDNA encoding the human interleukin 4 receptor*. International Immunology, vol. 2, No. 7, pp. 669-675, 1990.
Gregoraszczuk et al., *Response of porcine theca and granulosa cells to GH during short-term in vitro culture*, Animal Reproduction Science 58, pp. 113-125, Feb. 2000.
He et al., *Molecular Cloning Of Androgen Receptors From Divergent Species With A Polymerase Chain Reaction Technique: Complete cDNA Sequence Of The Mouse Androgen Receptor And Isolation Of Androgen Receptor cDNA Probes From Dog, Guinea Pig And Clawed Frog*, Biochemical and Biophysical Research Communications, vol. 171, No. 2, pp. 697-704, Sep. 1990.
Robert A. Hegele, *Paraoxonase genes and disease*, The Finnish Medical Society Duodecim, Ann Med, No. 31, pp. 217-224, Jun. 1999.
Hermansson et al., *Measurement of Human Growth Hormone Receptor Messenger Ribonucleic Acid by a Quantitative Polymerase Chain Reaction-Based Assay: Demonstration of Reduced Expression after Elective Surgury*, Journal of Clinical Endocrinology and Metabolism, vol. 82, No. 2, pp. 421-428, 1997.
Iwata et al., *Structure of the Mouse Tyrosine Hydroxylase Gene*, Biochemical and Biophysical Research Communications, vol. 182, No. 1, pp. 348-354, Jan. 1992.
Jansson et al., *Plasma growth hormone pattern and androgens indluence the levels of corticosteroid-binding globulin in rat serum*, Journal of Endocrinology, No. 122, pp. 725-732, Sep. 1989.
Kalaby et al., *Human Recombinant Alpha2-HS Glycoprotein is Produced in Insect Cells as a Full Length Inhibitor of the Insulin Receptor Tyrosine Kinase*, Horm. Metab. Res. 30, pp. 1-6, Jan. 1998.
Knapp et al., *Growth Patterns and Body Composition of Transgenic Mice Expressing Mutated Bovine Somatotropin Genes* [1,2], J. Amin. Sci., vol. 72, pp. 2812-2819, 1994.

(Continued)

Primary Examiner—Ethan Whisenant
(74) Attorney, Agent, or Firm—Iver P. Cooper

(57) ABSTRACT

Growth hormone-regulatable brown adipose tissue genes and proteins have been identified. They may be used as diagnostic markers of pathologies of adipose tissue.

16 Claims, 2 Drawing Sheets

OTHER PUBLICATIONS

Kohler et al., *Molecular Cloning of Mouse Glycolate Oxidase*, The Journal of Biological Chemistry, vol. 274, No. 4, pp. 2401-2407, Jan. 1999.

Kopchick et al., *Transgenic Models of Growth Hormone Action*, Annual Rev. Nutr., vol. 19, pp. 437-461, 1999.

Lemmey et al., *Differential regulation of tissue insulin-like growth factor-binding protein (IGFBP)-3, IGF-I and IGF type 1 receptor mRNA levels, and serum IGF-I and IGFBP concentrations by growth hormone and IGF-I*, Journal of Endocrinology, vol. 154, No. 2, pp. 319-328, 1997.

Malhotra et al., *Identification of differentially expressed mRNAs in human fetal liver across gestation*, Nucleic Acids Research, vol. 27, No. 3, pp. 839-847, Feb. 1999.

Marschall et al., *Human Liver Class I Alcohol Dehydrogenase Isozyme: The Sole Cytosolic 3-Hydroxysteroid Dehydrogenase of Iso Bile Acids*, Hepatology, vol. 31, No. 4, pp. 990-996, Apr. 2000.

Mizukoshi et al., *Serum Levels of Soluble Interferon Alfa/Beta Receptor as an Inhititory Factor of Interferon in the Patients With Chronic Hepatitis C*, Hepatology, vol. 30, No. 5, pp. 1325-1331, Nov. 1999.

Nahmias et al., *Molecular characterization of the mouse 3-adrenergic receptor: relationship with the atypical receptor of adipocytes*, The EMBO Journal, vol. 10, No. 12, pp. 3721-3727, 1991.

Panduro et al., *Liver-Specific Gene Expression in Various Pathophydiologic States*, Hepatology, vol. 7, No. 1, pp. 10S-18S, 1987.

Quaife et al., *Histopathology Associated with Elevated Levels of Growth Hormone and Insulin-Like Growth Factor I in Transgenic Mice*, Endochrinology, vol. 124, No. 1, 1989.

Ren et al., *In its active form, the GTP-binding protein rab8 interacts with a stress-activated protein kinase*, Proc. Natl. Acad. Sci. USA, vol. 93, pp. 5151-5155, May 1996.

Saggese et al., *Diagnosis and Treatment of Growth Hormone Deficiency in Children and Adolescents: Towards a Consensus*, Hormone Research, vol. 50, pp. 320-340, Dec. 1998.

Sharp et al., *Expression of an Ovine Growth Hormone Transgene in Mice Causes Organomegaly and Hepatic Lesions Which Resolve Following Transgene Inactivation*, Laboratory Animal Science, vol. 45, No. 5, Oct. 1995.

Shen et al., *Cirrhotic Liver Expresses Low Levels of the Full-Length and Truncated Growth Hormone Receptors*, Journal of Clinical Endocrinology and Metabolism, vol. 83, No. 7, Jul. 1998.

Soto et al., *Rib Metastasis Revealing Hepatocellular Carcinoma*, Scand J. Gastroenterol, vol. 35, pp. 333-336, 2000.

Le Stunff et al., *Growth Hormone Stimulates Interferon Regulatory Factor-1 Gene Expression in the Liver*, Endocrinology, vol. 139, No. 3, pp. 859-866, Mar. 1998.

Sumimoto et al., *Complementary DNA for the Mouse Homolog of the Small Subumit of Human Cytochrome $_{558}$*, Biochemical and Biophysical Research Communications, vol. 165, No. 2, pp. 902-906, Dec. 1989.

Van Kerkhof et al., *Endocytosis and Degradation of the Growth Hormone Receptor Are Proteasome-dependent*, The Journal of Biological Chemistry, vol. 275, No. 3, pp. 1575-1580, Jan. 2000.

Viguerie-Bascands et al., *Evidence for Numerous Brown Adipocytes Lacking Functional $_3$-Andrenoceptors in Fat Pads from Nonhuman Primates*, Journal of Clinical Endocrinology and Metabolism, vol. 81, No. 1, 1996.

Wang et al., *3-Hydroxy-3-methylglutaryl coenzyme A lyase (HL); cloning and characterization of a mouse liver HL cDNA and subchromosomal mapping of the human and mouse HL genes*, Mammalian Genome, vol. 4, pp. 382-387, 1993.

Yang et al., *Glomerulosclerosis and Body Growth Are Mediated by Different Portions of Bovine Growth Hormone*, Laboratory Investigation, vol. 68, No. 1, pp. 62-70, 1993.

Yatsuhashi et al., *Immunohistochemical analysis of hepatic interferon alpha-beta receptor level; relationship between receptor expression and response to interferon therapy in patients with chronic hepatitis C*, Journal of Hepatology, vol. 30, No. 6, pp. 995-1003, Jun. 1999.

Bjørn-Hansen Gøtzsche, et al., *The influence of growth hormone and thyroxina on iodothyronine deiodinase activity in the liver, kidney and brown adipose tissue in hypophysectomized rats*, Acta Endocrinologica, vol. 125, pp. 219-226, 1991.

Carvalho, et al., *Hormonal regulation of malic enzyme and glucose-6-phosphate dehydrogenase in brown adipose tissue*, AM. J. Physiol., vol. 264, No. 6, part 1, pp. E874-E881, 1993.

Charalampaki, et al., *Insulin-like growth factor binding protein-3 levels during early and late follow-up after surgery in acromegalic patients*, Exp. Clin. Endocrinol. Diabetes, bol. 106, pp. 130-134, 1998.

Nijland, et al., *A five day treatment with daily subcutaneous injections of growth hormone-releasing peptide-2 causes response attenuation and does not stimulate insulin-like growth factor-1 secretion in healthy young men*, European Journal of Endocrinology, vol. 139, pp. 395-401, 1998.

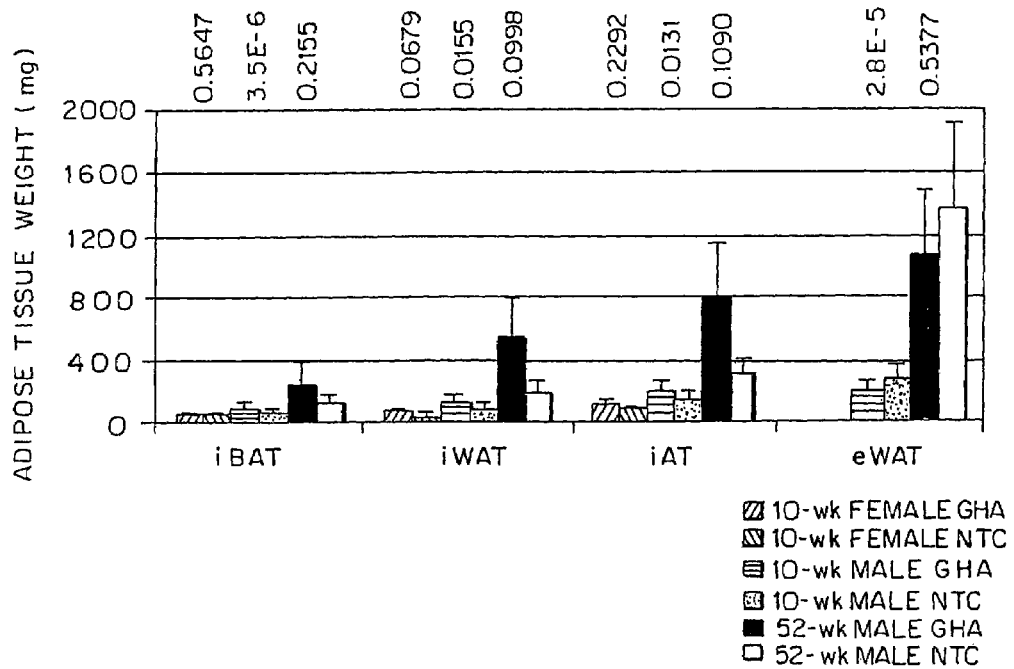
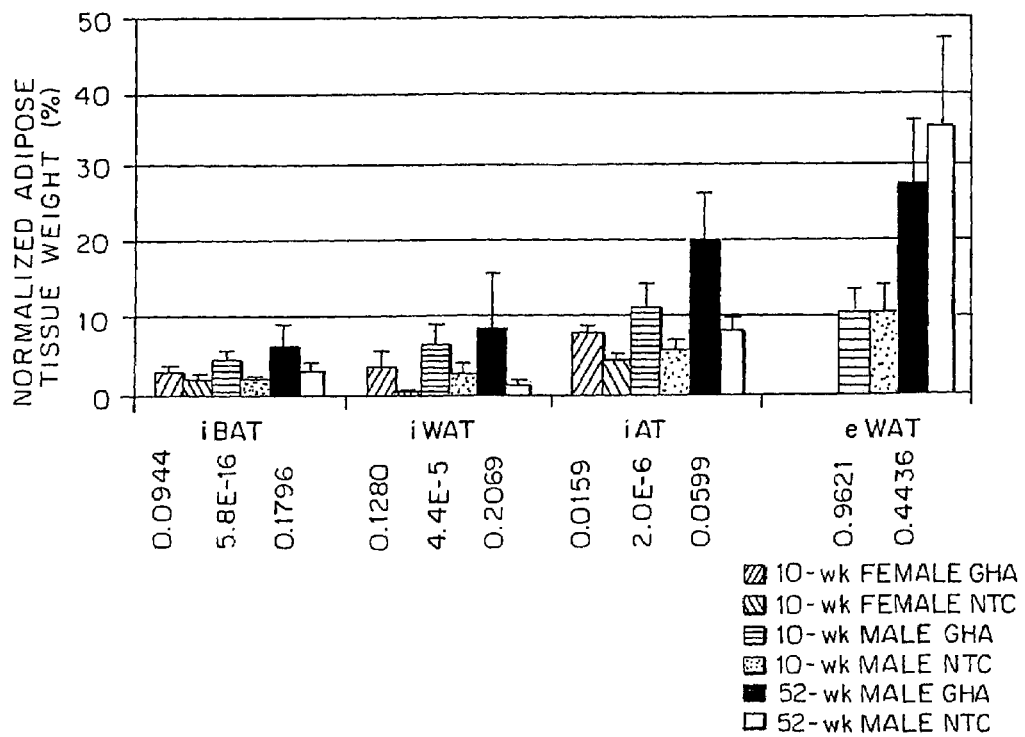

GROWTH HORMONE-REGULATABLE BROWN ADIPOSE TISSUE GENES AND PROTEINS AND USES THEREOF

REFERENCE TO RELATED APPLICATIONS

The present application is the national stage under 35 U.S.C. 371 of international application PCT/US00/12145, filed May 5, 2000, which designated the United States, and which international application was published under PCT Article 21(2) in the English language.

PCT/US00/12145 is a nonprovisional of Provisional Ser. No. 60/132,670, filed May 5, 1999.

BACKGROUND OF THE INVENTION

1. Field of the Invention

This invention relates to the diagnosis of abnormal GH activity or general pathological activity in brown adipose tissue.

2. Description of the Background Art

Brown Adipose Tissue:

Brown adipose tissue (BAT) is known as a major site of heat production or thermogenesis where it normally consumes fat derived from white adipose tissues (WAT). Brown adipocytes generally reside in capillary beds and are abundant in cytochromes and proteins, particularly uncoupling protein-1 ($UCP_1$). A BAT depot is located in the interscapular space in rodents, but exists in the abdominal, neck, and upper back areas in human neonates. In contrast to rodents, BAT gradually disappears as children grow. Recent studies demonstrated that brown adipocytes can also be found in rat and baboon WAT during cold stress (Cousin et al. 1992 and Viguerie-Bascands et al. 1996).

Growth Hormones:

The growth hormones are vertebrate proteins with about 191 amino acid residues, the number varying from species to species. There are four cysteine residues, and two disulfide bridges. The 3D-structure of porcine GH is known; it is composed of four major antiparallel alpha-helices, at residues 7–34, 75–87, 106–127 and 152–183.

The 3D structure of the hGH:hGH receptor complex is also known. Each molecule of hGH binds two molecules of the receptor. hGH binds to two binding sites on hGH receptor. *Helix* 4, the loop residues 54–74, and, to a lesser extent, helix 1, mediate binding to binding site 1. *Helix* 3 mediates binding to binding site 2.

See generally Harvey, et al., *Growth Hormone* (CRC Press:1995). GH is synthesized and secreted by the somatotrophic and somatomammotrophic cells of the lateral anterior pituitary. The control of GH production and secretion is complex, but is mainly under the influence of growth hormone releasing hormone (GHRH) and somatostatin, which stimulate and inhibit it, respectively. The shifting balance between these regulatory agents is responsible for the pulsatile nature of GH secretion, with normal human concentrations ranging from a baseline value <1 μg/L to peaks of 25–50 μg/L. Glucocorticoids and thyroid hormones, and various carbohydrates, amino acids, fatty acids and other biomolecules, are also known to directly or indirectly regulate GH secretion.

Most GH is secreted at night, during deep sleep, but some is secreted in response to exercise and other forms of physical stress. About 500 μg/m2 body surface area are secreted by women, and 350 by men. GH secretion rates are highest in adolescents and lowest in the elderly. GH has a plasma half-life of about 20–25 min. and is cleared at a rate of 100–150 ml/m2 body surface area.

Metabolic and Clinical Effects of Growth Hormone:

Chronic elevation of growth hormone levels in humans usually results in either gigantism or acromegaly. GH, besides affecting skeletal growth, can also influence other organ systems, in particular, the liver and kidney. In the kidney, it has been associated with glomerulosclerosis and nephropathy. In the liver, it has been shown to cause an increase in liver size, as a consequence of both hyperplasia and hepatocyte hypertrophy. The hepatocellular lesions associated with high GH levels progress with age. See Quaife, et al, Endocrinol., 124: 49 (1989).

There is reason to believe that excessive GH activity in the liver is deleterious to health. Mice that express GH transgenes typically live to only about one year of age, while the normal life expectancy for mice is 2–2.5 years. A major cause of death in the GH transgenic mice has been liver disease.

Growth hormone (GH) is an essential regulator of carbohydrate and lipid metabolism, participating in glucose uptake and usage, accelerating fat expenditure, preventing triglyceride accumulation, and facilitating lipid mobilization in adipose tissues. Growth patterns and body compositions of transgenic mice expressing GH analogs have been characterized in our laboratory (Knapp et al. 1994). One transgenic mouse line expresses a GH antagonist (GHA) and is dwarf. As these mice age, they become obese.

Chronic depression of GH levels can also impair health.

Growth Hormone Antagonists:

In view of the foregoing, it has been suggested that if a subject is suffering from excessive GH activity, it can be useful to inhibit such activity by inhibiting the production, release or action of GH, or facilitating the elimination of GH.

Among the agents useful for this purpose are those which are competitive binding antagonists of GH. It was discovered that certain mutants of GH are useful for this purpose. Kopchick, U.S. Pat. No. 5,350,836.

In order to determine whether it is appropriate to initiate or terminate use GH antagonists or other GH-inhibiting drugs, it is important to be able to monitor GH activity.

Monitoring of GH Activity:

The most straightforward marker of GH activity is the serum level of GH per se. For humans, the mean GH concentration (ug/L) in blood is

| | | |
|---|---|---|
| preadolescent | 4.6 | |
| early adolescent | 4.8 | |
| late adolescent | 13.8 | |
| adult | 1.8 | |
| ISS (10 y old) | 3.5 | |
| GH deficient | 1.4 | |
| IDDM (boys) | 9.0 | |
| Obese (male) | 0.66 | (lower than controls) |
| Fasting | 6.7 | (higher than controls) |
| Hyperthyroid | 1.9 | (higher than controls) |

ISS = idiopathic short stature,
IDDM = insulin dependent diabetes mellitus
See Harvey (1995), supra.

While there is definitely a correlation between high levels of GH in serum, and high levels of GH activity, it must be recognized that both the total number of GH receptors, and the distribution of those receptors among the various organs, will vary from individual to individual. Hence, in determining whether an individual is suffering from excessive GH activity, and prone to develop adverse clinical sequelae, it is helpful to identify a metabolite which is produced or released in direct or indirect response to GH and, in particular, one which is substantially liver-specific so that the specific threat to liver function can be assessed.

Another marker of GH activity is insulin-like growth factor-1 (IGF-1). IGF-1 is a 70 amino acid single chain protein, with some structural similarity to proinsulin, which is closely regulated by GH secretion. While the majority of IGF-1 synthesis occurs in the liver, many other tissues, including bone and skeletal muscle, also release IGF-1 in response to GH. IGF-1 levels have been used by clinicians to confirm suspected cases of acromegaly. However, it would be desirable to have a marker, or combination of markers, which was more liver specific than IGF-1, for use in monitoring and predicting the effect of chronic elevation of GH levels on liver function.

SUMMARY OF THE INVENTION

Applicants have identified certain genes whose expression in brown adipose tissue is elevated or depressed as a result of higher than normal GH levels.

By use of nucleic acid binding agents to bind messenger RNA transcripts produced by the transcription of any of these genes (or to bind the corresponding complementary DNAs synthesized in vitro), or by use of a protein binding agent to bind a protein encoded by any of these genes, it is possible to assay the level of transcription of the gene in question, or the level of expression and secretion of the corresponding protein, and to correlate such level with the level of GH activity in brown adipose tissue.

BRIEF DESCRIPTION OF THE DRAWINGS

FIG. 2 Northern Blot of UCP1 in BAT from Different Transgenic Mouse. Hybridizing total RNA prepared from various tissues of 10-week old male and female NT mice with 605-bp probe, a portion of UCP1 ORF sequence, the UCP1 signals are only observed in iBAT in male transgenic mice and NT littermates after 2-hr exposure even prolonged exposure. The mRNA level of UCP1 is enhanced in GHA and GHR/BPKO mice and is reduced in bGH mice when comparing that in NT littermates. The ratio of intensity volume of UCP1 to β-actin demonstrates that these changes are substantial.

DETAILED DESCRIPTION OF THE PREFERRED EMBODIMENTS OF THE INVENTION

Figure 1A:
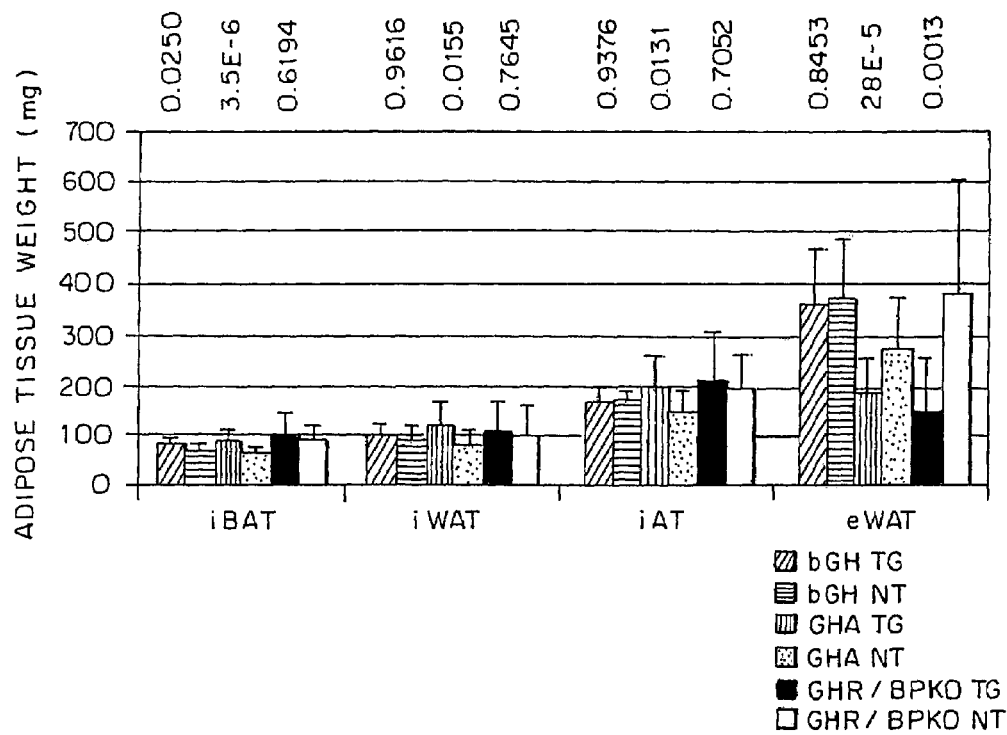
FIG. 1 Analysis of Brown Adipose Tissue Growth in Transgenic Mice. In upper panel (A), 10-week old male GHA mouse has remarkably-enlarged size of iaT ($p=0.0131$), iBAT ($p=3.5 \times 10^{-6}$), and iWAT ($p=0.0155$) comparing to their nontransgenic littermates. This overgrowth has been observed at least at a similar significant level for iAT ($p=2.0 \times 10^{-6}$), IBAT ($p=5.8 \times 10^{-16}$), and iWAT ($p=4.4 \times 10^{-5}$) if normalized by their body weights. In lower panel (B), since the body size of GHR/BP is about 51.8% of NT littermate, the size for those adipose tissues are not significantly different from NT littermate by gram. However, when normalized by its body weight in percentage, the enlargement has been observed at a significant level for iAT ($p=4.5 \times 10^{-4}$), iBAT ($p=5.8 \times 10^{-16}$), and iWAT ($p=1.0 \times 10^{-5}$). In both dwarf mice, the size of eWAT tends to be proportional to that of entire body by weight. The significant difference for eWAT weight ($p=2.8 \times 10^{-5}$ in GHA group and $p=0.0013$ in GHR/BPKO group) may be due to their small body size. Although iBAT weight of bGH mouse is greater than that of NT littermate ($p=0.0250$), normalized iBAT weight in percentage does not exhibit any significant difference for iAT, IBAT, iWAT, and eWAT, suggesting that, in bGH mice, those adipose tissues grow rather proportionally to the body weight and that any impairment of GH signaling may result in an overlarged size of interscapular adipose tissue which constitutes of iBAT and iWAT.
Figure 1B:
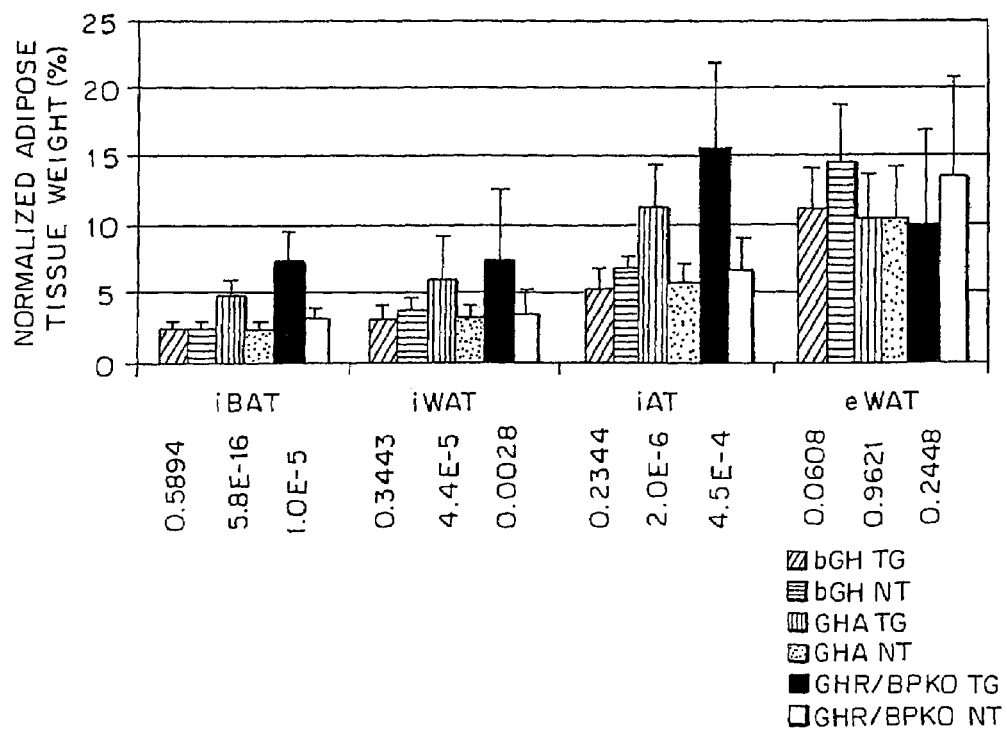

We have found that the BAT mass in the GHA mice (n=17) is significantly greater (p=0.011) than that found in their non-transgenic (NT) littermates (n=24) when normalized for body weight. Hence, we proposed that genes in BAT may be up or down-regulated by GH.

To examine this hypothesis, we employed a PCR-select cDNA subtraction assay (Clontech) and constructed a forward subtraction library by subtracting NT littermate BAT cDNAs from GHA BAT cDNAs and a reverse subtraction library by subtracting GHA BAT cDNAs from NT BAT cDNAs. Positive clones were screened by differential hybridization using probes made from the two subtracted cDNA libraries. Partial cDNAs were isolated, sequenced, and analyzed by BLAST searches. We found genes encoding glucosephosphate isomerase, α-enolase, pyruvate kinase, proteasome, ubiquitin, and heme oxygenase in the forward subtraction library, indicating that these genes are up-regulated in GHA BAT. We found genes encoding mitochondria cytochrome b, mitochondria cytochrome C oxidase subunit I, mitochondria NADH-ubiquinone oxidoreductase chain 4 and/or 6, medium chain acyl-CoA dehydrogenase, adipocyte lipid binding protein, and trans-Golgi network in the reverse subtraction library, indicating that these genes are down-regulated in GHA BAT. These results may partially explain why GHA mice become obese.

The present invention relates to the use of these genes and proteins as diagnostic markers in the analysis of brown adipose tissue structure and function, in particular, its differentiation, theriogenesis and pathologies.

It is now possible to determine the level of the mRNAs or proteins corresponding to these genes, in normal adipose tissue as compared to adipose tissue in a pathological state, and thereby determine reference values of these mRNAs or proteins which are indicative of a particular pathological state.

Known pathologic lesions in adipose tissues include:
  white adipose tissues:
    Aging; insulin resistance; hyperlipidemia; non-insulin dependent diabetes mellitus; obesity; benign and malignant tumor
  Brown adipose tissue and brown adipocyte;
    Aging; insulin resistance; hyperlipidemia; non-insulin dependent diabetes mellitus; obesity; benign and malignant tumor
  Convertible adipose tissues and convertible adipocytes:
    Aging; insulin resistance; hyperlipidermia; non-insulin dependent diabetes mellitus; obesity; benign and malignant tumor.

The preferred screening assay for this purpose is an antisense probe assay.

It additionally may be of advantage to ascertain the level of the mRNAs and proteins in cells of the liver, kidney, muscle, heart, spleen, intestine, brain, lung, testis, and ovary, and correlate the level with a particular pathological condition.

Definitions

Two proteins are cognate if they are produced in different species, but are sufficiently similar in structure and biological activity to be considered the equivalent proteins for those species. If the accepted scientific names for two proteins are the same but for the species identification (e.g., human GH and shark GH), they should be considered cognate. If not, the two proteins may still be considered cognate if they have at least 50% amino acid sequence identity (when globally aligned with a pam250 scoring matrix with a gap penalty of the form $q+r(k-1)$ where k is the length of the gap, $q=-12$ and $r=-4$; percent identity=number of identities as percentage of length of shorter sequence) and at least one biological activity in common.

Two genes are cognate if they are expressed in different species and encode cognate proteins.

Gene expression may be said to be specific to a particular tissue if the average ratio of the specific mRNA to total mRNA for the cells of that tissue is at least 10% higher than the average ratio is for the cells of some second tissue. Absolute specificity is not required. Hence, a gene may be said to be expressed specifically in more than one tissue.

When the term "specific" is used in this specification, absolute specificity is not intended, merely a detectable difference.

Preferably the markers of the present invention are, singly or in combination, more specific to the target tissue than are serum GH or IGF-1 levels, or than GH mRNA or IGF-1 mRNA levels in the target tissue.

If this specifications calls for alignment of DNA sequences, and one of the sequences is intended for the use as a hybridization probe, the sequences are to be aligned using a local alignment program with matches scored +5, mismatches scored −4, the first null of a gap scored −12, and each additional null of the same gap scored −2. Percentage identity is the number of identities expressed as a percentage of the length of the overlap, including internal gaps.

In Vitro Assays

The in vitro assays of the present invention may be applied to any suitable analyte-containing sample, and may be qualitative or quantitative in nature.

For the techniques to practice these assays, see, in general, Ausubel, et al., *Current Protocols in Molecular Biology*, and in particular chapters 2 ("Preparation and Analysis of DNA"), 3 ("Enzymatic Manipulation of DNA and RNA"), 4 ("Preparation and Analysis of RNA"), 5 ("Construction of Recombinant DNA libraries") 6 ("Screening of Recombinant DNA Libraries"), 7 ("DNA Sequencing"), 10 ("Analysis of Proteins"), 11 ("Immunology"), 14 ("In situ hybridization and immune histochemistry"), 15 ("The Polymerase Chain Reaction"), 19 ("Informatics for Molecular Biologists"), and 20 ("Analysis of Protein Interactions"). Also see, in general, Coligan, et al., *Current Protocols in Immunology*, and in particular, chapters 2 ("Induction of immune responses"), 8 ("Isolation and Analysis of Proteins"), 9 ("Peptides"), 10 ("Molecular Biology") and 17 ("Engineering Immune Molecules and Receptors"). Also see Coligan, et al., *Current Protocols in Protein Science*.

The Assay Target (Analyte)

The assay target may be a positive or negative marker. A positive marker is one for which a higher signal is correlated with abnormally high growth hormone activity. A negative marker is one for which a higher signal is correlated with abnormally low growth hormone activity. Positive markers are up-regulated in high GH mammals and down-regulated in low GH mammals. Negative markers are up-regulated in high GH mammals and down-regulated in low GH mammals.

A mammal which expresses a GH antagonist (GHA) is normally considered a low GH level, because it expresses the endogenous GH at presumably normal levels but the overall GH activity is depressed as a result of the co-expression of the GHA.

Hence, genes which are up-regulated in GHA mice are actually negative markers, while genes which are down-regulated in GHA mice are actually positive markers.

In one embodiment, the assay target is a messenger RNA transcribed from a gene which, in brown adipose tissue, has increased transcriptional activity if serum GH levels are increased. This messenger RNA may be a full length transcript of the gene, or merely a partial transcript. In the latter case, it must be sufficiently long so that it is possible to achieve specific binding, e.g., by nucleic acid hybridization. For the purpose of conducting the assay, the messenger RNA is extracted from brown adipose tissue by conventional means. Alternatively, the assay target may be a complementary DNA synthesized in vitro from the messenger RNA as previously described.

For convenience, the term "gene" or "target sequence" will be used to refer to both the messenger RNA or complementary DNA corresponding to the induced gene, and to the coding gene proper.

In another embodiment, the assay target is a protein encoded by said gene and expressed at higher levels in response to elevated GH levels. If the protein is secreted, the assay may be performed on serum. If the protein is not secreted, then cells of brown adipose tissue will be obtained from the subject and lysed to expose the cytoplasmic contents.

In either embodiment, one or more purification steps may be employed prior to the practice of the assay in order to enrich the sample for the assay target.

The proteins of particular interest are as follows:

Negative Markers:
glucosephosphate isomerase
neuroleukin
pyruvate kinase
heme oxygenase
ubiquitin/ribosomal fusion protein
α-enolase
proteasome 0 chain Positive Markers
trans-Golgi network protein
medium chain acyl-CoA dehydrogenase
adipocyte lipid binding protein
cytochrome c oxidase
NADH-ubiquonone oxidoreductase
cytochrome b The genes of particular interest are those encoding the above proteins. These genes were identified, as described in Example 1, on the basis of the identity or similarity of mouse cDNAs obtained by subtractive hybridization methods to known mouse genes or cDNAs. The mouse sequences are set forth in the figures. However, if the assay is of a human subject, the target gene or protein will of course be the cognate human gene or protein. The sequence databank ID numbers for these cognate human genes and proteins are given in Table A.

Certainly newly discovered DNAs are also of interest as positive markers. These are identified below as clones
Ng-G119K2
Ng-G119K15
Ng-G119K36
Ng-G119K62

Ng-G119K42
Ng-G119K58
Ng-G119K65
Ng-G119K66

The proteins encoded by the ORFs embedded in these DNAs are also of interest.

Samples

The sample may be of any biological fluid or tissue which is reasonably expected to contain the messenger RNA transcribed from one of the above genes, or a protein expressed from one of the above genes. The sample may be of brown adipose tissue or interstitial fluid, or of a systemic fluid into which brown adipose tissue proteins are secreted.

A non-invasive sample collection will involve the use of urine samples from human subjects. Blood samples will also be obtained in order to obtained plasma or serum from which secreted proteins can be evaluated. Brown adipose tissue aspirates can also be obtained to detect for the presence of genes and proteins of interest. The most invasive method would involve obtaining brown adipose tissue biopsies.

Analyte Binding Reagents (Molecules, ABM)

When the assay target is a nucleic acid, the preferred binding reagent is a complementary nucleic acid. However, the nucleic acid binding agent may also be a peptide or protein. A peptide phage library may be screened for peptides which bind the nucleic acid assay target. In a similar manner, a DNA binding protein may be randomly mutagenized in the region of its DNA recognition site, and the mutants screened for the ability to specifically bind the target. Or the hypervariable regions of antibodies may be mutagenized and the antibody mutants displayed on phage.

When the assay target is a protein, the preferred binding reagent is an antibody, or a specifically binding fragment of an antibody. The antibody may be monoclonal or polyclonal. It can be obtained by first immunizing a mammal with the protein target, and recovering either polyclonal antiserum, or immunocytes for later fusion to obtain hybridomas, or by constructing an antibody phage library and screening the antibodies for binding to the target. The binding reagent may also be a binding molecule other than an antibody, such as a receptor fragment, an oligopeptide, or a nucleic acid. A suitable oligopeptide or nucleic acid may be identified by screening a suitable random library.

Binding and Reaction Assays

The assay may be a binding assay, in which one step involves the binding of a diagnostic reagent to the analyte, or a reaction assay, which involves the reaction of a reagent with the analyte. The reagents used in a binding assay may be classified as to the nature of their interaction with analyte: (1) analyte analogues, or (2) analyte binding molecules (ABM) They may be labeled or insolubilized.

In a reaction assay, the assay may look for a direct reaction between the analyte and a reagent which is reactive with the analyte, or if the analyte is an enzyme or enzyme inhibitor, for a reaction catalyzed or inhibited by the analyte. The reagent may be a reactant, a catalyst, or an inhibitor for the reaction.

An assay may involve a cascade of steps in which the product of one step acts as the target for the next step. These steps may be binding steps, reaction steps, or a combination thereof.

Signal Producing System (SPS)

In order to detect the presence, or measure the amount, of an analyte, the assay must provide for a signal producing system (SPS) in which there is a detectable difference in the signal produced, depending on whether the analyte is present or absent (or, in a quantitative assay, on the amount of the analyte). The detectable signal may be one which is visually detectable, or one detectable only with instruments. Possible signals include production of colored or luminescent products, alteration of the characteristics (including amplitude or polarization) of absorption or emission of radiation by an assay component or product, and precipitation or agglutination of a component or product. The term "signal" is intended to include the discontinuance of an existing signal, or a change in the rate of change of an observable parameter, rather than a change in its absolute value. The signal may be monitored manually or automatically.

In a reaction assay, the signal is often a product of the reaction. In a binding assay, it is normally provided by a label borne by a labeled reagent.

Labels

The component of the signal producing system which is most intimately associated with the diagnostic reagent is called the "label". A label may be, e.g., a radioisotope, a fluorophore, an enzyme, a co-enzyme, an enzyme substrate, an electron-dense compound, an agglutinable particle.

The radioactive isotope can be detected by such means as the use of a gamma counter or a scintillation counter or by autoradiography. Isotopes which are particularly useful for the purpose of the present invention are $^3$H, $^{32}$P, $^{125}$I, $^{131}$I, $^{35}$S, $^{14}$C, and, preferably, $^{125}$I.

The label may also be a fluorophore. When the fluorescently labeled reagent is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

Alternatively, fluorescence-emitting metals such as $^{125}$Eu, or others of the lanthanide series, may be incorporated into a diagnostic reagent using such metal chelating groups as diethylenetriaminepentaacetic acid (DTPA) of ethylenediamine-tetraacetic acid (EDTA).

The label may also be a chemiluminescent compound. The presence of the chemiluminescently labeled reagent is then determined by detecting the presence of luminescence that arises during the course of a chemical reaction. Examples of particularly useful chemiluminescent labeling compounds are luminol, isolumino, theromatic acridinium ester, imidazole, acridinium salt and oxalate ester.

Likewise, a bioluminescent compound may be used for labeling. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Enzyme labels, such as horseradish peroxidase and alkaline phosphatase, are preferred. When an enzyme label is used, the signal producing system must also include a substrate for the enzyme. If the enzymatic reaction product is not itself detectable, the SPS will include one or more additional reactants so that a detectable product appears.

An enzyme analyte may act as its own label if an enzyme inhibitor is used as a diagnostic reagent.

Conjugation Methods

A label may be conjugated, directly or indirectly (e.g., through a labeled anti-ABM antibody), covalently (e.g., with SPDP) or noncovalently, to the ABM, to produce a diagnostic reagent.

Similarly, the ABM may be conjugated to a solid phase support to form a solid phase ("capture") diagnostic reagent.

Suitable supports include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention.

The support material may have virtually any possible structural configuration so long as the coupled molecule is capable of binding to its target. Thus the support configuration may be spherical, as in a bead, or cylindrical, as in the inside surface of a test tube, or the external surface of a rod. Alternatively, the surface may be flat such as a sheet, test strip, etc.

Binding Assay Formats

Binding assays may be divided into two basic types, heterogeneous and homogeneous. In heterogeneous assays, the interaction between the affinity molecule and the analyte does not affect the label, hence, to determine the amount or presence of analyte, bound label must be separated from free label. In homogeneous assays, the interaction does affect the activity of the label, and therefore analyte levels can be deduced without the need for a separation step.

In one embodiment, the ABM is insolubilized by coupling it to a macromolecular support, and analyte in the sample is allowed to compete with a known quantity of a labeled or specifically labelable analyte analogue. The "analyte analogue" is a molecule capable of competing with analyte for binding to the ABM, and the term is intended to include analyte itself. It may be labeled already, or it may be labeled subsequently by specifically binding the label to a moiety differentiating the analyte analogue from analyte. The solid and liquid phases are separated, and the labeled analyte analogue in one phase is quantified. The higher the level of analyte analogue in the solid phase, i.e., sticking to the ABM, the lower the level of analyte in the sample.

In a "sandwich assay", both an insolubilized ABM, and a labeled ABM are employed. The analyte is captured by the insolubilized ABM and is tagged by the labeled ABM, forming a ternary complex. The reagents may be added to the sample in either order, or simultaneously. The ABMs may be the same or different. The amount of labeled ABM in the ternary complex is directly proportional to the amount of analyte in the sample.

The two embodiments described above are both heterogeneous assays. However, homogeneous assays are conceivable. The key is that the label be affected by whether or not the complex is formed.

Detection of Genes of Interest

For the detection of genes in the sample, PCR can be done using primers specific for the genes of interest. This would amplify the genes of interest. Primers may be designed to anneal to any site within the open reading frames of the genes of interest. Resolution of the fragments by electrophoresis on agarose gel may be used to determine the presence of the genes. PCR product may be quantitated by densitometry in order to estimate the concentration of the genes in the samples.

Detection of genes of interest may also be done by Northern blot analysis on liver biopsies. Tissue sample from patients may be obtained and the total RNA extracted using RNAStat 60. The total RNA sample may then be resolved on denaturing gel by electrophoresis and then transferred onto a nylon membrane. After transfer of RNA onto the membrane, the membrane may then be used in hybridization with a suitable probe, which may be a synthetic probe directed against a gene already known to be a marker, or which may be a cDNA probe prepared directly from subtractive hybridization, wherein the fragment encoding the gene of interest, that is enriched in GH-overproducing subjects, will be labeled, preferably either radioactively with $^{32}$P or non-radioactively with DIG (Digoxigenin). A negative control, such as one composed of RNA sample from brown adipose tissue of normal subjects, may be resolved side by side with the patients' sample, to determine quantitatively whether there is a significant increase in the level of gene expression. Elevation of the messenger RNA transcript from this gene would imply that brown adipose tissue damage might have occurred.

The DNA sequences of the present invention may be used either as hybridization probes per se, or as primers for PCR.

In a hybridization assay, a nucleic acid reagent may be used either as a probe, or as a primer. For probe use, only one reagent is needed, and it may hybridize to all or just a part of the target nucleic acid. Optionally, more than one probe may be used to increase specificity. For the primer-based assay, two primers are needed. These hybridize the non-overlapping, separated segments of the target sequence. One primer hybridizes to the plus strand, and the other to the minus strand. By PCR techniques, the target nucleic acid region starting at one primer binding site and ending at the other primer binding site, along both strands, is amplified, including the intervening segment to which the primers do not hybridize. In a primer-based assay, the primer thus will not correspond to the entire target, but rather each primer will correspond to one end of the target sequence.

In probe-based assays, hybridizations may be carried out on filters or in solutions. Typical filters are nitrocellulose, nylon, and chemically-activated papers. The probe may be double stranded or single stranded, however, the double stranded nucleic acid will be denatured for binding.

To be successful, a hybridization assay, whether primer- or probe-based, must be sufficiently sensitive and specific to be diagnostically useful.

For probe-based assays, sensitivity is affected by the amount and specific activity of the probe, the amount of the target nucleic acid, the detectability of the label, the rate of hybridization, and the duration of the hybridization. The hybridization rate is maximized at a Ti (incubation temperature) of 20–25° C. below Tm for DNA:DNA hybrids and 10–15° C. below Tm for DNA:RNA hybrids. It is also maximized by an ionic strength of about 1.5M Na$^+$. The rate is directly proportional to duplex length and inversely proportional to the degree of mismatching.

For primer-based PCR assays, sensitivity is not usually a major issue because of the extreme amplification of the signal.

For probe-based assays, specificity is a function of the difference in stability between the desired hybrid and "background" hybrids. Hybrid stability is a function of duplex length, base composition, ionic strength, mismatching, and destabilizing agents (if any).

The Tm of a perfect hybrid may be estimated.

for DNA:DNA hybrids, as $T_m$=81.5C+16.6 (log M)+0.41 (%GC)-0.61 (% form)-500/L and for DNA:RNA hybrids, as $T_m = 79.8°C + 18.5 (\log M) + 0.58 (\% GC) - 11.8 (\% GC)^2 - 0.56(\% \text{form}) - 820/L$ where M, molarity of monovalent cations, 0.01–0.4 M NaCl, % GC, percentage of G and C nucleotides in DNA, 30%–75%, % form, percentage formamide in hybridization solution, and L, length hybrid in base pairs.

Tm is reduced by 0.5–1.5° C. for each 1% mismatching.

Tm may also be estimated by the method of Tinoco et al., developed originally for the determination of the stability of a proposed secondary structure of an RNA. Tm may also be determined experimentally.

Filter hybridization is typically carried out at 68° C., and at high ionic strength (e.g., 5–6×SSC), which is nonstringent, and followed by one or more washes of increasing stringency, the last was being of the ultimately desired stringency. The equations for Tm can be used to estimate the appropriate Ti for the final wash, or the Tm of the perfect duplex can be determined experimentally and Ti then adjusted accordingly.

While a mouse cDNA was used to probe a mouse liver cDNA library, and could be used to probe nonmurine liver cDNA libraries, it would be expected that there would be some sequence divergence between cognate mouse and nonmouse DNAs, possibly as much as 25–50%.

Hence, when the human DNA cognate to the original mouse cDNA is known, it is better to use that DNA, or a fragment thereof, to probe a human liver cDNA library. The practitioner may use the complete genomic DNA or cDNA sequence of the human gene as a probe, or, for the sake of greater specificity or synthetic convenience, a partial sequence.

It is also noted that while some of the mouse clones were identical to subsequences of a databank mouse DNA, others diverged slightly (up to 5%). This divergence could be artifactual (sequencing error) or real (allelic variation).

Hybridization conditions should be chosen so as to permit allelic variations, but avoid hybridizing to other genes. In general, stringent conditions are considered to be a Ti of 5° C. below the Tm of a perfect duplex, and a 1% divergence corresponds to a 0.5–1.5° C. reduction in Tm. Typically, the mouse clones were 95–100% identical to database mouse sequences. Hence, use of a Ti of 5–15° C. below, more preferably 5–10° C. below, the Tm of the double stranded form of the probe is recommended.

If the sequences of the major allelic variants are known, one may use a mixed probe, and optionally increase the stringency.

If there is no known human gene cognate to the mouse (or rat) gene homologous to the clone, then the mouse (or rat) gene, or other known nonhuman cognate gene, may be used as a probe. In this case, more moderate stringency hybridization conditions should be used. The nonhuman gene may be modified to obey a more human set of codon preferences.

Alternatively, the mouse (or rat) gene may be used once as a probe to isolate the human gene, and the human gene then used for diagnostic work. If a partial human cDNA is obtained, it may be used to isolate a larger human cDNA, and the process repeated as needed until the complete human cDNA is obtained.

For cross-species hybridization, the Ti should be reduced further, by about 0.5–1.5° C., e.g., 1° C., for each expected 1% divergence in sequence. The degree of divergence may be estimated from the known divergence of the most closely related pairs of known genes from the two species.

If the desired degree of mismatching results in a wash temperature less than 45° C., it is desirable to increase the salt concentration so a higher temperature can be used. Doubling the SSC concentration results in about a 17° C. increase in Tm, so washes at 45° C. in 0.1×SSC and 62° C. in 0.2×SSC are equivalent (1×SSC=0.15 M NaCl, 0.015M trisodium citrate, pH 7.0).

The person skilled in the art can readily determine suitable combinations of temperature and salt concentration to achieve these degrees of stringency.

The hybridization conditions set forth in the examples may be used as a starting point, and then made more or less stringent as the situation merits.

Examples of successful cross-species-hybridization experiments include Braun, et al., EMBO J., 8:701–9 (1989) (mouse v. human), Imamura, et al., Biochemistry, 30:5406–11 (1991) (human v. rat), Oro, et al, Nature, 336:493–6 (1988) (human v. *Drosophila*), Higuti, et al., Biochem. Biophys. Res. Comm., 178:1014–20 (1991) (rat v. human), Jeung, et al., FEBS Lett., 307:224–8 (1992) (rat, bovine v. human), Iwata, et al., Biochem. Biophys. Res. Comm., 182:348–54 (1992) (human v. mouse), Libert, et al., Biochem. Biophys. Res. Comm., 187:919–926 (1992) (dog v. human), Wang, et al., Mamm. Genome, 4:382–7 (1993) (human v. mouse), Jakubiczka, et al., Genomics, 17:732–5 (1993) (human v. bovine), Nahmias, et al., EMBO J., 10:3721–7 (1991) (human v. mouse), Potier, et al., J. DNA Sequencing and Mapping, 2:211–218 (1992) (rat v. human), Chan, et al., Somatic Cell Molec. Genet., 15:555–62 (1989) (human v. mouse), Hsieh, et al., Id., 579–590 (1989) (human, mouse v. bovine), Sumimoto, et al., Biochem. Biophys. Res. Comm., 165:902–6 (1989) (human v. mouse), Boutin, et al., Molec. Endocrinol., 3:1455–61 (1989) (rat v. human), He, et al., Biochem. Biophys. Res. Comm., 171:697–704 (1990) (human, rat v. dog, guinea pig, frog, mouse), Galizzi, et al., Int. Immunol., 2:669–675 (1990) (mouse v. human). See also Gould, et al., Proc. Nat. Acad. Sci. USA, 86:1934–8 (1989).

In general, for cross-species hybridization, Ti=25–35° C. below Tm. Wash temperatures and ionic strengths may be adjusted empirically until background is low enough.

For primer-based PCR assays, the specificity is most dependent on reagent purity.

The final considerations are the length and binding site of the probe. In general, for probe-based assays, the probe is preferably at least 15, more preferably at least 20, still more preferably at least 50, and most preferably at least 100 bases (or base pairs) long. Preferably, if the probe is not complementary to the entire gene, it targets a region low in allelic variation.

In general, for primer-based PCR assays, the primer is preferably at least 18–30 bases in length. Longer primers do no harm, shorter primers may sacrifice specificity. The distance between the primers may be as long as 10 kb, but is preferably less than 3 kb, and of course should taken into account the length of the target sequence (which is likely to be shorter for mRNA or cDNA than for genomic DNA). Preferably, primers have similar GC content, minimal secondary structure, and low complementarily to each other, particularly in the 3' region. Also, their targets are preferably relatively invariant from allete to allete.

For theoretical analysis of probe design considerations, see Lathe, et al., J. Mol. Biol., 183:1–12 (1985).

Detection of Proteins of Interest

ELISA can be done on blood plasma or serum from patients using antibodies specific to the protein of interest. Samples will be incubated with primary antibodies on plates. This primary antibody is specific to the protein of interest.

Another method that can be conducted will involve the use of chemical or enzymatic reactions in which the protein of interest will act as a substrate (or, if the protein is an enzyme, as a catalyst) to cause a reaction that lead to the production of colored solution or emission of fluorescence.

Spectrometric analysis can be done in order to determine the concentration of the proteins in the sample.

Western blot analysis can also be done on the plasma/serum, tissue aspirate, tissue biopsies or urine samples. This would involve resolving the proteins on an electrophoretic gel, such as an SDS PAGE gel, and transferring the resolved proteins onto a nitrocellulose or other suitable membrane. The proteins are incubated with a target binding molecule, such as an antibody.

This binding reagent may be labeled or not. If it is unlabeled, then one would also employ a secondary, labeled molecule which binds to the binding reagent. One approach involves avidinating one molecule and biotinylating the other. Another is for the secondary molecule to be a secondary antibody which binds the original binding reagent.

To improve detection of the specific protein, immunoprecipitation can be conducted. This typically will involve addition of a monoclonal antibody against the protein of interest to samples, then allowing the Ig-protein complex to precipitate after the addition of an affinity bead (ie antihuman Ig sepharose bead). The immunoprecipitates will undergo several washings prior to transfer onto a nitrocellulose membrane. The Western blot analysis can be perform using another antibody against the primary antibody used.

Interpretation of Assay Results

The assay may be used to predict the clinical state of the brown adipose tissue if the level of GH activity remains unchanged.

A scheme for the diagnostic interpretation of the level of the target in question is determined in a conventional manner by monitoring the level of GH, the level of the target, and the brown adipose tissue condition in a suitable number of patients, and correlating the level of the target at an earlier time point with the simultaneous or subsequent brown adipose tissue state.

This correlation is then used to predict the future clinical state of the brown adipose tissue in new patients with high GH levels.

The diagnosis may be based on a single marker, or upon a combination of markers, which may include, besides the markers mentioned above, the level of GH or of IGF-1. A suitable combination may be identified by any suitable technique, such as multiple regression, factor analysis, or a neural network using the scaled levels of the markers as inputs and the current or subsequent brown adipose tissue state as an output.

In Vivo Diagnostic Uses

Radio-labelled ABM which are not rapidly degraded in blood may be administered to the human or animal subject. Administration is typically by injection, e.g., intravenous or arterial or other means of administration in a quantity sufficient to permit subsequent dynamic and/or static imaging using suitable radio-detecting devices. The dosage is the smallest amount capable of providing a diagnostically effective image, and may be determined by means conventional in the art, using known radio-imaging agents as a guide.

Typically, the imaging is carried out on the whole body of the subject, or on that portion of the body or organ relevant to the condition or disease under study. The amount of radio-labelled ABM accumulated at a given point in time in relevant target organs can then be quantified.

A particularly suitable radio-detecting device is a scintillation camera, such as a gamma camera. A scintillation camera is a stationary device that can be used to image distribution of radio-labelled ABM. The detection device in the camera senses the radioactive decay, the distribution of which can be recorded. Data produced by the imaging system can be digitized. The digitized information can be analyzed over time discontinuously or continuously. The digitized data can be processed to produce images, called frames, of the pattern of uptake of the radio-labelled ABM in the target organ at a discrete point in time. In most continuous (dynamic) studies, quantitative data is obtained by observing changes in distributions of radioactive decay in target organs over time. In other words, a time-activity analysis of the data will illustrate uptake through clearance of the radio-labelled binding protein by the target organs with time.

Various factors should be taken into consideration in selecting an appropriate radioisotope. The radioisotope must be selected with a view to obtaining good quality resolution upon imaging, should be safe for diagnostic use in humans and animals, and should preferably have a short physical half-life so as to decrease the amount of radiation received by the body. The radioisotope used should preferably be pharmacologically inert, and, in the quantities administered, should not have any substantial physiological effect.

The ABM may be radio-labelled with different isotopes of iodine, for example $^{123}$I, $^{125}$I, or $^{131}$I (see for example, U.S. Pat. No. 4,609,725). The extent of radio-labeling must, however be monitored, since it will affect the calculations made based on the imaging results (i.e. a diiodinated ABM will result in twice the radiation count of a similar monoiodinated ABM over the same time frame).

In applications to human subjects, it may be desirable to use radioisotopes other than $^{125}$I for labelling in order to decrease the total dosimetry exposure of the human body and to optimize the detectability of the labelled molecule (though this radioisotope can be used if circumstances require). Ready availability for clinical use is also a factor. Accordingly, for human applications, preferred radio-labels are for example, $^{99m}$Tc, $^{67}$Ga, $^{68}$Ga, $^{90}$Y, $^{111}$In, $^{113m}$In, $^{123}$I, $^{186}$Re, $^{188}$Re or $^{211}$At.

The radio-labelled ABM may be prepared by various methods. These include radio-halogenation by the chloramine—T method or the lactoperoxidase method and subsequent purification by HPLC (high pressure liquid chromatography), for example as described by J. Gutkowska et al in "Endocrinology and Metabolism Clinics of America: (1987) 16 (1):183. Other known method of radio-labelling can be used, such as IODOBEADS™.

There are a number of different methods of delivering the radio-labelled ABM to the end-user. It may be administered by any means that enables the active agent to reach the agent's site of action in the body of a mammal. Because proteins are subject to bering digested when administered orally, parenteral administration, i.e., intravenous subcutaneous, intramuscular, would ordinarily be used to optimize absorption of an ABM, such as an antibody, which is a protein.

Other Uses

The markers in question may also be used to determine if the subject is suffering from or prone to develop a disorder associated with insufficient GH activity in the brown adipose tissue.

Presumably, in that event the positive markers will be at abnormally low levels, and the negative markers are abnormally low levels.

EXAMPLES

BLASTN searches were performed with the default parameters match +1, mismatch −3, gap q=−5 r=−2, penalty q+rk for gap length k. For BLASTP, BLOSUM62 matrix with q=−1, r=−1, lambda ratio=0.85.

Example 1

Brown Adipose Tissue (BAT) Total RNA Preparation 70-day old male G119K growth hormone antagonist (GHA) mice and their non-transgenic (NT) littermates were sacrificed by neck dislocation. Their interscapular brown adipose tissues (BAT) were immediately dissected, weighed, placed in 10 volumes of cold RNA STAT-60™ solution (TEL-TEST "B", Friendswood, Tex.), and carefully homogenized on ice. Total RNAs were prepared by following the manufacture's protocol. Total RNA pellets were usually stored in 75% ethanol at 80° C. for not more than 6 months.

SMART™ PCR cDNA Synthesis

Fresh BAT total RNAs from GHA and NT mice were prepared with RNA STAT-60TM kit (TEL-TEST "B", Friendswood, Tex.) and further purified with QIAEX® II Rneasy Mini Kit (Qiagen, Chatsworth, Calif.). Purified total RNAs were quantified by their spectrum ratio of A260/A280 and their band intensity ratio of 18S/28S on 1% formaldehyde-Agarose gel. 1 μg of each purified total RNA (as starting material) was then applied to first-strand cDNA synthesis with SMART™ PCR cDNA Synthesis Kit (CLONTECH, Palo Alto, Calif.). Major components, cDNA synthesis (CDS) primer (AAGCAGTGGTAACAACGCA-GAGTACT$_{(30)}$N$_{-1}$N) (SEQ ID NO:1), SMART II oligonucleotide (AAGCAGTGGTAACAACGCAGAG-TACGCGGG) (SEQ ID NO:2), and MMLV reverse transcriptase (Gibco BRL, Palo Alto, Calif.), were included in these reactions. The second-strand cDNAs were synthesized in the presence of Advantage KlenTaq Polymerase Mix and PCR primer (AAGCAGTGGTAACAACGCA-GAGT) (bases 1-23 of SEQ ID NO:2). The double-stranded (ds) cDNAs were then simultaneously amplified under the Kit-recommended PCR program (95° C. for 1 minute and 15~21 cycles of 95° C. for 15 seconds, 65° C. for 30 seconds, and 68° C. for 6 minutes). 20 for GHA and 18 for NT were determined as optimal number of PCR cycles by electrophoresing 5 μl of each PCR product on a 1.2% Agarose/EtBr gel so that all BAT SMART™ PCR cDNAs were equally synthesized for following subtraction.

PCR-Select™ cDNA Subtraction

BAT SMART™ PCR cDNAs were sized with Column chromatography and cleaved with Rsa I by following the protocol provided with PCR-Select™ cDNA Subtraction Kit (CLONTECH, Palo Alto, Calif.). The digested cDNAs were purified with QIAEX II Agarose Gel Extraction Kit (Qiagen, Chatsworth, Calif.), microfiltrated and precipitated with this Subtraction Kit. Final concentrations of 300 ng/μl were made to both GHA and NT mouse Rsa I-restricted BAT SMART™ PCR cDNAs.

Standard adapter ligations were performed in the presence of either adaptor 1 (CTAATACGACTCACTATAGGGCTC-GAGCGGCCGCCCGGGCAGGT) (SEQ ID NO:3) or adaptor 2R (CTAATACGACTCACTATAGGGCAGCGTG-GTCGCGGCCGAGGT) (SEQ ID NO:4) under the direction of PCR-Select™ cDNA Subtraction Kit so that GHA-adaptor 1, GHA-adaptor 2R, NT-adaptor 1, and NT-adaptor 2R were respectively prepared to serve as experimental tester cDNAs while unligated Rsa I-restricted cDNAs were used as experimental driver cDNAs.

The GHA-adaptor 1 and GHA-adaptor 2R experimental tester cDNAs were first cross-hybridized with Rsa I-restricted NT experimental driver cDNAs respectively; while the NT-adaptor 1 and NT-adaptor 2R tester cDNAs were done with Rsa I-restricted GHA driver cDNAs respectively. After 8-hour air-incubation at 68° C., the second hybridization was followed by simply mixing the first cross-hybridization products and incubating at 68° C. overnight: GHA-adaptor 1 tester/NT driver and GHA-adaptor 2R/NT driver, or NT-adaptor 1 tester/GHA driver and NT-adaptor 2R/GHA driver.

The final hybridized cDNAs were primarily amplified in the presence of PCR primer 1 (CTAATACGACTCACTAT-AGGGC) (bases 1–22 of SEQ ID NO:4) and Advantage KlenTaq Polymerase Mix under the Kit-recommended PCR program (94° C. for 25 seconds and 27–32 cycles of 94° C. for 10 seconds, 66° C. for 30 seconds, and 72° C. for 1.5 minutes); then those PCR cDNA products were secondarily amplified again in the presence of Nested PCR primer 1 (TCGAGCGGCCGCCCGGGCAGGT) (SEQ ID NO:5) and Nested PCR primer 2R (AGCGTGGTCGCGGCCGAGGT) (SEQ ID NO:6) for additional 9–15 cycles (94° C. for 10 seconds, 68° C. for 30 seconds, and 72° C. for 1.5 minutes) followed by 72° C. for 5 minutes. The number of primary PCR cycles were 27 for GHA and 29 for NT; while that of secondary PCR cycles were 9 for both GHA and NT. These optimal number of PCR cycles were determined by electrophoresing 8 μl of each PCR product on a 2% Agarose/EtBr gel to minimize the non-specific BAT SMART™ PCR-Select subtracted cDNA products.

Analyses of double-stranded cDNA synthesis products, Rsa I digestion, adaptor ligation, and subtraction efficiency were performed according to the recommendation of PCR-Select™ cDNA Subtraction Kit. End products from each manipulation were visualized on 1.2–2% Agarose/EtBr gel before proceeding to do the next step.

Subtraction Library Construction

Fresh secondary PCR amplification products after PCR-Select cDNA subtraction were ligated to 3.9 kb PCR™ II vector with a standard method provided by TA Cloning Kit (Invitrogen, Carlsbad, Calif.). After 16-hour incubation at 14° C., these products were used to transform library efficiency DH5 α™ competent cells (Life Technologies, Palo Alto, Calif.) onto LB-ampicillin plates by using a recommended small-scale protocol. α-complementation of the β-galactosidase gene within this vector was employed to produce blue/white screening of colonies on bacterial plates containing X-gal. 160 white colonies were isolated from each subtraction library: forward subtraction library (GHA subtracting NT) and reverse subtraction library (NT subtracting GHA); total 320 colonies were maintained.

PCR-Select Differential Screening

The adaptor sequences of the secondary PCR amplification products after PCR-Select cDNA subtraction were removed by restricting with Rsa I digestion; and digested products were purified with QIAEX II Agarose Gel Extraction Kit (Qiagen, Chatsworth, Calif.) and precipitated with NH₄AC and ethanol at ~20° C. overnight. The down-stream products were then used to random-prime PCR Dig-labeled probes by incubating at 37° C. for 5 hours with DIG High Prime DNA Labeling Kit (Boehringer Mamheim, Indianapolis, Ind.). The concentration of both forward and reverse subtraction library probes were estimated with the series dilution of Dig-labeled marker.

cDNA arrays were at mean time made with the PCR-Select Differential Screening Kit (CLONTECH, Palo Alto, Calif.) under the provided instruction. All PCR inserts were examined with Nested Primer 1 and Nested Primer 2R on 2% Agarose/EtBr gels before the cDNA dot blot duplicate were prepared onto the positively-charged nylon membrane (Boehringer Mamheim, Indianapolis, Ind.) from either the forward or the reverse subtraction library for further library screening.

The cDNA dot blot duplicate from forward subtraction library were pre-hybridized with DIG Easy Hyb solution (Boehringer Mamheim, Indianapolis, Ind.) at 50° C. for 1 hour and hybridized respectively with random-primed Dig-labeled probe prepared from forward subtraction library and reverse subtraction at same temperature for 14 hours. The same protocol was simultaneously applied to the duplicate from reverse subtraction library. Washing procedures and detection of Dig-labeled nucleic acids were standardized under the Genius™ System User's Guide for membrane hybridization (Boehringer Mamheim, Indianapolis, Ind.). By observing the differential signals present in dot blot duplicates, 26 positive clones were screened from forward subtraction library and 14 from reverse subtraction library. Plasmids with positive inserts were prepared with Plasmid Midi Kit (Qiagen, Chatsworth, Calif.). These inserts were sequenced with dGTP mix by using Thermo Sequenase $^{33}$P radiolabeled terminator cycle sequencing Kit (Amersham, Cleveland, Ohio). All sequences were applied to BLAST search (http://www.ncbi.nlm.nih.gov/BLAST) so that they could be determined whether a known sequence was identified at both nucleic acid and amino acid levels by its alignment to the DNA and protein databases.

Among the 26 clones from the forward subtraction library, 25 were homologous to known genes, as follows:

| Gene | Number |
| --- | --- |
| glucosoephosphate isomerase and neuroleukin | 1 |
| pyruvate kinase | 1 |
| heme oxygenase | 1 |
| ubiquitin/ribosomal fusion protein | 1 |
| alpha-enolase | 2 |
| proteasome theta chain | 2 |
| G119K BGH mutant | 17 |

One clone was considered irrelevant.

Among 14 clones from the reverse subtraction library, ten were homologous to known genes, as follows:

| Gene | Number |
| --- | --- |
| trans-Golgi network protein | 1 |
| medium chain acyl-CoA dehydrogenase | 1 |
| adipocyte lipid binding protein | 2 |
| mitochondrial cytochrome c oxidase | 1 |
| NADF1-ubiquonone oxidoreductase | 2 |
| cytochrome b | 3 |

There were also four novel sequences: Ng-G119K2, Ng-G119K15, Ng-G119K36 and Ng-G119K62. Two of these were further studied in Ex. 2.

Example 2

Brown Adipose Tissue (BAT) Total RNA Preparation 70-day old male G119K growth hormone antagonist (GHA) mice and their non-transgenic (NT) littermates were sacrificed by neck dislocation. Their interscapular brown adipose tissues (BAT) were immediately dissected, weighed, placed in 10 volumes of cold RNA STAT-60™ solution (TEL-TEST "B", Friendswood, Tex.), and carefully homogenized on ice. Total RNAs were prepared by following the manufacturers protocol. Total RNA pellets were usually stored in 75% ethanol at −80° C. for not more than 6 months.

SMART™ PCR cDNA Synthesis

Fresh BAT total RNAs from GHA and NT mice were prepared with RNA STAT-60™ kit (TEL-TEST "B", Friendswood, Tex.) and further purified with QIAEX® II Rneasy Mini Kit (Qiagen, Chatsworth, Calif.). Purified total RNAs were quantified by their spectrum ratio of A260/A280 and their band intensity ratio of 18S/28S on 1% formaldehyde-Agarose gel. 1 µg of each purified total RNA (as starting material) was then applied to first-strand cDNA synthesis with SMART™ PCR cDNA Synthesis Kit (CLONTECH, Palo Alto, Calif.). Major components, cDNA synthesis (CDS) primer (AAGCAGTGGTAACAACGCAGAGTACT$(_{30})$N$_{-1}$N) (SEQ ID NO:1), SMART II oligonucleotide (AAGCAGTGGTAACAACGCAGAGTACGCGGG) (SEQ ID NO:2), and MMLV reverse transcriptase (Gibco BRL, Palo Alto, Calif.), were included in these reactions. The second-strand cDNAs were synthesized in the presence of Advantage KlenTaq Polymerase Mix and PCR primer (AAGCAGTGGTAACAACGCAGAGT) (bases 1–23 of SEQ ID NO:2). The double-stranded (ds) cDNAs were then simultaneously amplified under the Kit-recommended PCR program (95° C. for 1 minute and 15–21 cycles of 95° C. for 15 seconds, 65° C. for 30 seconds, and 68° C. for 6 minutes). 20 for GHA and 18 for NT were determined as optimal number of PCR cycles by electrophoresing 5 µl of each PCR product on a 1.2% Agarose/EtBr gel so that all BAT SMART™ PCR cDNAs were equally synthesized for following subtraction.

PCR-Select™ cDNA Subtraction

BAT SMART™ PCR cDNAs were sized with Column chromatography and cleaved with Rsa I by following the protocol provided with PCR-Select™ cDNA Subtraction Kit (CLONTECH, Palo Alto, Calif.). The digested cDNAs were purified with QIAEX II Agarose Gel Extraction Kit (Qiagen, Chatsworth, Calif.), microfiltrated and precipitated with this Subtraction Kit. Final concentrations of 300 ng/µl were made to both GHA and NT mouse Rsa I-restricted BAT SMART™ PCR cDNAs.

Standard adapter ligations were performed in the presence of either adaptor 1 (CTAATACGACTCACTATAGGGCTC-GAGCGGCCGCCCGGGCAGGT) (SEQ ID NO:3) or adaptor 2R (CTAATACGACTCACTATAGGGCAGCGTG-GTCGCGGCCGAGGT) (SEQ ID NO:4) under the direction of PCR-Select™ cDNA Subtraction Kit so that GHA-adaptor 1, GHA-adaptor 2R, NT-adaptor 1, and NT-adaptor 2R were respectively prepared to serve as experimental tester cDNAs while unligated Rsa I-restricted cDNAs were used as experimental driver cDNAs.

The GHA-adaptor 1 and GHA-adaptor 2R experimental tester cDNAs were first cross-hybridized with Rsa I-restricted NT experimental driver cDNAs respectively; while the NT-adaptor 1 and NT-adaptor 2R tester cDNAs were done with Rsa I-restricted GHA driver cDNAs respectively. After 8-hour air-incubation at 68° C., the second hybridization was followed by simply mixing the first cross-hybridization products and incubating at 68° C. overnight: GHA-adaptor 1 tester/NT driver and GHA-adaptor 2R/NT driver, or NT-adaptor 1 tester/GHA driver and NT-adaptor 2R/GHA driver.

The final hybridized cDNAs were primarily amplified in the presence of PCR primer 1 (CTAATACGACTCACTAT-AGGGC) (bases 1–22 of SEQ ID NO:4) and Advantage KlenTaq Polymerase Mix under the Kit-recommended PCR program (94° C. for 25 seconds and 27~32 cycles of 94° C. for 10 seconds, 66° C. for 30 seconds, and 72° C. for 1.5 minutes); then those PCR cDNA products were secondarily amplified again in the presence of Nested PCR primer 1 (TCGAGCGGCCGCCCGGGCAGGT) (SEQ ID NO:5) and Nested PCR primer 2R (AGCGTGGTCGCGGCCGAGGT) (SEQ ID NO:6) for additional 9~15 cycles (94° C. for 10 seconds, 68° C. for 30 seconds, and 72° C. for 1.5 minutes) followed by 72° C. for 5 minutes. The number of primary PCR cycles were 27 for GHA and 29 for NT; while that of secondary PCR cycles were 9 for both GHA and NT. These optimal number of PCR cycles were determined by electrophoresing 8 μl of each PCR product on a 2% Agarose/EtBr gel to minimize the non-specific BAT SMART™ PCR-Select subtracted cDNA products.

Analyses of double-stranded cDNA synthesis products, Rsa I digestion, adaptor ligation, and subtraction efficiency were performed according to the recommendation of PCR-Select™ cDNA Subtraction Kit. End products from each manipulation were visualized on 1.2–2% Agarose/EtBr gel before proceeding to do the next step.

Subtraction Library Construction

Fresh secondary PCR amplification products after PCR-Select cDNA subtraction were ligated to 3.9 kb PCR™ II vector with a standard method provided by TA Cloning Kit (Invitrogen, Carlsbad, Calif.). After 16-hour incubation at 14° C., these products were used to transform library efficiency DH5α™ competent cells (Life Technologies, Palo Alto, Calif.) onto LB-ampicillin plates by using a recommended small-scale protocol. α-complementation of the β-galactosidase gene within this vector was employed to produce blue/white screening of colonies on bacterial plates containing X-gal. 160 white colonies were isolated from each subtraction library: forward subtraction library (GHA subtracting NT) and reverse subtraction library (NT subtracting GHA); total 320 colonies were maintained.

PCR-Select Differential Screening

The adaptor sequences of the secondary PCR amplification products after PCR-Select cDNA subtraction were removed by restricting with Rsa I digestion; and digested products were purified with QIAEX II Agarose Gel Extraction Kit (Qiagen, Chatsworth, Calif.) and precipitated with $NH_4AC$ and ethanol at Ð20° C. overnight. The down-stream products were then used to random-prime PCR Dig-labeled probes by incubating at 37° C. for 5 hours with DIG High Prime DNA Labeling Kit (Boehringer Mamheim, Indianapolis, Ind.). The concentration of both forward and reverse subtraction library probes were estimated with the series dilution of Dig-labeled marker.

cDNA arrays were at mean time made with the PCR-Select Differential Screening Kit (CLONTECH, Palo Alto, Calif.) under the provided instruction. All PCR inserts were examined with Nested Primer 1 and Nested Primer 2R on 2% Agarose/EtBr gels before the cDNA dot blot duplicate were prepared onto the positively-charged nylon membrane (Boehringer Mamheim, Indianapolis, Ind.) from either the forward or the reverse subtraction library for further library screening.

The cDNA dot blot duplicate from forward subtraction library were pre-hybridized with DIG Easy Hyb solution (Boehringer Mamheim, Indianapolis, Ind.) at 50° C. for 1 hour and hybridized respectively with random-primed Dig-labeled probe prepared from forward subtraction library and reverse subtraction at same temperature for 14 hours. The same protocol was simultaneously applied to the duplicate from reverse subtraction library. Washing procedures and detection of Dig-labeled nucleic acids were standardized under the Genius™ System UserÕs Guide for membrane hybridization (Boehringer Mamheim, Indianapolis, Ind.). By observing the differential signals present in dot blot duplicates, 26 positive clones were screened from forward subtraction library and 14 from reverse subtraction library. Plasmids with positive inserts were prepared with Plasmid Midi Kit (Qiagen, Chatsworth, Calif.). These inserts were sequenced with dGTP mix by using Thermo Sequenase $^{33}P$ radiolabeled terminator cycle sequencing Kit (Amersham, Cleveland, Ohio). All sequences were applied to BLAST search (http://www.ncbi.nlm.nih.gov/BLAST) so that they could be determined whether a known sequence was identified at both nucleic acid and amino acid levels by its alignment to the DNA and protein databases. Based on these internet searches, two novel partial cDNA sequences from the reverse subtraction library, Ng-G119K36 and Ng-G119K62, have been chosen for further study.

SMART™ PCR cDNA Library Construction

NT BAT SMART™ PCR cDNAs were synthesized from fresh purified NT BAT total RNAs with CDS primer and SMART II oligonucleotide at PCR cycle 20 by using SMART™ PCR cDNA Library Construction Kit (CLONTECH, Palo Alto, Calif.). The integrity of this SMART cDNA was examined with 5 pairs of primers: 540 bp mouse β-actin, 606 bp mouse uncoupling protein 1 ($UCP_1$), 521 bp mouse GHR, 452 bp mouse glycerol-3-phosphate dehydrogenase (G3PDH), and approximately 250 bp hypoxanthine phosphoribosyltransferase (HPRT). The PCR program was 1 cycle of 94° C. for 2 minutes, 55 cycles of 94° C. for 30 seconds, 60° C. for 30 seconds, and 68~72° C. for 1~2 minutes, 1 cycle of 68~72° C. for 7 minutes, and held at 4° C.

The polished SMART ds cDNA were ligated with 5' overhang EcoR I adaptor (13-mer: 5'-OH-AATTCGGCAC-GAG-3' (SEQ ID NO:7); 9-mer: 3'-GCCGTGCTC-Pi-5') by using the ZAP-cDNA® Gigapack® III Gold Cloning Kit (STRATAGEN, La Jolla, Calif.), purified by organic reagent extraction, precipitated with NaAC and ethanol, and phosphorylated in the presence of T4 polynucleotide kinase and ATP, then size-fractionated with column provided in this ZAP-cDNA® Gigapack® III Gold Cloning Kit. Fractional drops from number 12 through 18 were collected together and further precipitated with cold ethanol at Ð20° C. overnight. 25~100 ng of this SMART cDNA were then ligated to 1 µg of 41 kb λZAPII predigested vector at 12° C. overnight and packaged with Gigapack® III Gold packaging extract at 22° C. for 1.5 hours.

Following the instruction of ZAP-cDNA® Gigapack® III Gold Cloning Kit, 200 µl of 0.5 $OD_{600}$ fresh XL-1 Blue MRF— strain was mixed with 0.1–1 µl of packaged SMART cDNAs in 2–3 ml of NZY top agar at 48~55° C., then immediately inoculated onto a fresh NZY agar plate (100-mm), and incubated at 37° C. for 8 hours. The titer ranged from $1.5–1.8×10^6$ plaque forming unit (pfu) every 1 µg vector arm. 600 µl of 0.5 $OD_{600}$ fresh XL-1 Blue $MRF^-$ strain was mixed with a twentieth aliquot of packaged SMART cDNA in 6.5 ml of NZY top agar at 48~55° C., then immediately inoculated onto a fresh NZY agar plate (150-mm), and incubated at 37° C. for 8 hours. The titer was approximately $4.05×10^5$ pfu per plate (150-mm). The amplified library was made by pooling all samples together with SM dilution buffer and stored in 7% (v/v) dimethylsulfoxide (DMSO) solution at Ð80° C. The titer was similarly determined on the NZY plate (100-mm): $4.30×10^5$ pfu/µl amplified library. A mini-PCR reactions were set up as 3.25 µl $dH_2O$, 0.5 µl 10× PCR buffer, 0.05 µl 10 µM $T_7$ primer and 0.05 µl 10 µM $M_{13}R(-48)$ primer, 0.1 µl 10 mM dNTPs, 0.05 µl 5 unit/ml Taq DNA polymerase (Promega, Madison, Wis.), and 1.0 µl DNA template-containing released particle from every isolated plaque with the parameters: 1 cycle of 95 C. for 2 minutes, 50 cycles of 94° C. for 30 seconds, 55° C. for 30 seconds, and 72° C. for 5 minutes, 1 cycle of 72° C. for 7 minutes, and 4° C. to hold. All total 5 µl reaction volume per reaction was loaded to 1% Agarose/EtBr gel to determine the recombinational rate.

SMART™ PCR cDNA Library Screening

600 µl of 0.5 $OD_{600}$ fresh XL-1 Blue MRF— strain was mixed with approximately 2 µl of amplified library in 6.5 ml of NZY top agar at 48~55° C., then immediately inoculated onto a fresh NZY agar plate (150-mm), and incubated at 37° C. for 8 hours. Duplicates of pre-shrinked (sterilization cycle for 10 minutes) nylon membranes (132 mm φ) (Boehringer Mamheim, Indianapolis, Ind.) were placed to pre-cooled plaques on NZY agar plates for 2 minutes to make the first duplicate and for 4 minutes to make the second duplicate, orientated with insoluble ink by needling at its edge through the NZY agar, then blotted onto the filter papers. These plaque lifts were immobilized when autoclaving at sterilization cycle for 2 minutes.

Two entire inserts of positive clone Ng-G119K36 and Ng-G119K62 from reverse subtraction library were used to prepare the probes in the presence of Nested Primer 1 and Nested Primer 2R with the PCR DIG Probe Synthesis Kit (Boehringer Mamheim, Indianapolis, Ind.). The concentration of both Ng-G119K36 and Ng-G119K62 probes were estimated with the series dilution of Dig-labeled marker.

The plaque lift duplicates were pre-hybridized with DIG Easy Hyb solution (Boehringer Mamheim, Indianapolis, Ind.) at 42° C. for 1 hour and hybridized respectively with PCR Dig-labeled probe prepared from either clone Ng-G119K36 or clone Ng-G119K62 from reverse subtraction library for about 12 hours. Washing procedures and detection of Dig-labeled nucleic acids were standardized under the Genius™ System User's Guide for membrane hybridization (Boehringer Mamheim, Indianapolis, Ind.). Plaques showing signals in plaque lift duplicates were isolated and prepared for further multiple screening on NZY agar plate (100-mm) until plaques were purified.

Following the protocol provided with ZAP-cDNA® Gigapack® III Gold Cloning Kit (STRATAGEN, La Jolla, Calif.), SOLR strain was prepared to excise the pBluescript phagemid out from each purified plaque screened from full-length NT BAT SMART cDNA library. Colonies were isolated from LB-ampicillin plates, prepared with Plasmid Maxi Kit (Qiagen, Chatsworth, Calif.), and maintained for further studies.

Inserts within purified plasmids were sequenced with either dITP mix or dGTP mix by using Thermo Sequenase $^{33}P$ radiolabeled terminator cycle sequencing Kit (Amersham, Cleveland, Ohio). Downstream sequence determined from each reaction was used to design the primer for next run sequencing reaction until all sequences from a single insert can be overlapped together to deduce a completed full-length cDNA sequence. All full-length sequences were applied to BLAST search (http://www.ncbi.nlm.nih.gov/BLAST) so that they could be determined whether a known sequence was called at both nucleic acid and amino acid levels by its alignment to the DNA and protein databases. An automated DNA sequencing approach was also employed in this project as well. Half reactions followed by isopropanol precipitation were chosed by using ABI PRISM® BigDye™ Terminator Cycle Sequencing Ready Reaction Kit (Perkin-Elmer, Foster City, Calif.). All samples were arranged to the ABI PRISM 310 Genetic Analyzer. Sequences done with automated fashion were edited with the ABI PRISM Edit-View 1.0.1.sea software which is downloaded from the website (http://www2.perkin-elmer.com/ab/techsupp/softlib/SeqAnal/installs/mac/EditView 1.0.1.sea.hqx).

In general, two novel cDNAs sequences were identified.

Clone 42 was screened with a Ng-G119K36 PCR Dig-labeled probe.

Clone 42 codes a 2478-bp mRNA with an open reading frame encoding 346-amino acid sequence. Clone 42 has two isoforms, 2.4-kb & 1.2-kb, which seem down-regulated in GHA mice. Clone 42 is widely expressed in most tissues; there are significant levels of both isoforms in BAT, a pronounced level of the long isoform in brain and a striking level of the short isoform in testis. Predicted secondary structure seems a helix-like polypeptide with a 18-amino acid signal peptide and relatively low hydrophobicity value. Predicted tertiary structure contains 7–8 hydrophobic regions through the sequence. The folding model seems similar to bacteriorhodopsin which is a important protein for proton conductance in archaebacterial. A BLAST search (FIG. 2(e)) demonstrates that Clone 42 is highly homologous to Clone 25077 mRNA from human female fetal brain tissue and PTD 010 mRNA from human pituitary tumor at both mRNA level and amino acid level.

Three other clones, Clone 58 (1380 bp), Clone 65 (2437 bp), and Clone 66 (1613 bp) were screened with the same Ng-G119K62 PCR Dig-labeled probe.

Clone 58, 65, & 66 seem like triple alternative splice forms which are 1379-bp, 2436=bp, 1612-bp mRNAs respectively. All these isoforms may encode a possible open reading frame containing 86 amino acids. The predicted open reading frame has a homology of two human genomic DNA sequences from clone 415G2 on chromosome 22 which contains synapsin IIa exon 1, EST and GSS. All these isoforms do not match up with any sequence in public protein database. The expression of long isoform tend to be BAT-specific.

Conclusions

Body weight and subcutaneous adipose tissue seems accumulated with age in GHA mice. An impairment of GH-induced signaling leads to abnormal growth of interscapular adipose tissues. GH-induced signaling has also been observed to down-regulate uncoupling protein-1 at transcriptional level.

In interscapular brown adipose tissue, GH may down-regulate genes coding glycolytic enzymes, ubiquitin/proteasome degradation machinery, and heme oxygenase; GH may up-regulate genes coding adipocyte lipid binding protein, trans-Golgi network protein (TGN38), medium chain acyl-CoA dehydrogenase, and mitochondrial innermembrane proteins for electron respiration chain. These GH-regulatable genes may be used as potential molecular markers to help explain obesity in GHA mice.

Clone 42 codes a 2478-bp mRNA with an open reading frame encoding 346-amino acid sequence. Two isoforms, 1.2-kb & 2.4-kb, are up-regulatable by GH and are widely expressed in most tissues with significant levels in BAT, pronounced level of long isoform in brain, and striking level of the short isoform in testis. It seems a helix-like polypeptide with a 18-amino acid signal peptide and relatively low hydrophobicity value. Clone 42 is highly homologous to Clone 25077 mRNA from human female fetal brain tissue and PTD 010 mRNA from human pituitary tumor at both mRNA level and amino acid level.

Clone 58, 65, & 66 seem like triple alternative splice forms which are 1379-bp, 2436-bp, 1612-bp mRNAs respectively. They may encode a possible open reading frame containing 86 amino acids, with a homology of two human genomic DNA sequences from clone 415G2 on chromosome 22 containing synapsin 111a exon 1, EST and GSS. The expression of clone 65 tend to be BAT-specific.

Example 3

A. Use of Mouse BAT genes in Assay of Human BAT

Brown adipose tissues are obtained from the human subject in a conventional, medically acceptable manner. Total RNA is then extracted using mL RNAStat60 per gram of tissue.

To 15–20 ug of brown adipose tissue RNA isolates, 1× MOPS, formaldehyde, formamide and ethidium bromide will be added, heat denatured at 60° C. then loaded on a formamide containing denaturing 1% agarose gel. The RNA will then be resolved by electrophoresis at 50V for about 2–2½ h. After electrophoresis, the gel will be washed twice briefly with deionized water; then once with 0.05N NaOH, with 0.1M Tris at pH 7.5, and with 10×SSC at washing times of at least 30 min in each case.

The resolved RNA after electrophoresis will be transferred onto a nylon membrane by upward gradient adsorption using 10×SSC as transfer buffer. The RNA on the membrane will be UV crosslinked at 120 mJ, after which the RNA blots will be ready for hybridization.

B. Northern Blot Hybridization Involving Non-radioactive DIG-Labeled Probe

Northern blot hybridization using digoxigenin (DIG)-labeled probe will be conducted to determine whether the genes of interest are present in brown adipose tissue RNA blots. The probes to be used for hybridization will be prepared from pCR2 clones, which contain as inserts the fragments isolated by subtractive hybridization of brown adipose tissue genes from GHA mice versus WT mice.

1. Preparation of DIG-labeled probe

The DIG-labelled probe preparation will require PCR amplification of the inserts in pCR2 clones using Taq polymerase as polymerization enzyme and pCR 2.1A and pCR 2B as primers. The conditions for PCR amplification will be 95° C. for 2 min.; 55 cycles at three temperature conditions of 95° C. for 15 sec., 58° C. for 20 sec., and 72° C. for 45 sec.; then 72° C. for 7 min. The amplified double-stranded cDNA fragment will undergo a second PCR amplification using a single primer, pCR 2.1A, in the presence of DIG labeled dNTPs to produce a single stranded DIG-labeled PCR product which will serve as the probe for RNA blot hybridization. The concentrations of the DIG labeled probe will be determined by comparing the signals produced by the probe to that of control DIG-labeled DNA upon exposure to radiographic film.

2. RNA Blot Hybridization

The concentration of DIG-labeled probe to be used for hybridization will be 50 ng/mL of DIG Easy Hyb solution (Boehringer-Mannheim). Prior to hybridization, the RNA blots will be prehybridized in DIG Easy Hyb solution at 42° C. for 30–60 min. Following prehybridization, the RNA blots will undergo hybridization using the probes prepared form the different pCR 2 clones. Hybridization will be done at 42° C. for at least 8 hours.

Posthybridization washings of the membrane will then be performed at room temperature for 5 min using a solution of 2×SSC and 0.1% SDS; and twice at 60° C. for 15 min. using a solution of 0.5×SSC and 0.1% SDS. The RNA blots will then be incubated with DIG antibody, which is conjugated to alkaline phosphatase. This antibody recognizes the DIG labeled hybrids in the RNA blot. CSPD (Boehringer-Mannheim), which is a chemiluminescent substrate, for alkaline phosphatase, will be use to achieve detection of the RNA of interest in the blot. The presence of bands that is specific to the brown adipose tissue genes of interest could be diagnostic of brown adipose tissue damage.

C. Northern Blot Hybridization involving $^{32}$P-labeled probe

1. Preparation of $^{32}$P-labeled probe

The $^{32}$P-labeled probe will be prepared by first isolating the cDNA fragments that were inserted into the pCR 2 vector by performing EcoRI restriction enzyme digestion. The fragments will be purified though a Qiaex$^R$ agarose gel extraction column (Qiagen). A 25 ng of the purified fragment will serve as a template for the production of single-stranded $^{32}$P-labeled probe using Random Primed DNA Labeling kit (Boehringer-Mannheim). The unincorporated dNTPs will be separated from the radiolabeled fragments using STE Select D G-25 column. The purified radiolabeld probe will then be quantified to determine the activity of the probe per ug of the DNA template. A good labeling of the template would have a specific activity range of $10^8$–$10^9$ cpm/ug of the template DNA.

2. RNA Blot hybridization

Prior to hybridization, prehybridization of the RNA blots will be performed by incubating the membrane in prehybridization solution made up of 50% formamide, 1% SDS, 1M NaCl, and 10% Dextran sulfate for 1 hour at 42° C. Hybridization of the RNA blot with the $^{32}$P-labeled probes prepared will follow after prehybridization. This will be conducted at 42° C. for at least 8 hours. Washing of the blots will be conducted once with 2×SSC at room temp for 5 min. and then with 2×SSC, 0.1% SDS at 56° C. which could last for about 5 minutes to an hour depending on the intensity of the radiactive signal. Radiographic exposure of the blots will determine whether the genes of interest are present.

REFERENCES

Cousin, B, Cinti, S, Morroni, M, Raimbault, S, Ricquier, D, and Penicaud, L. 1992. Occurrence of brown adipocytes in rat white adipose tissue: molecular and morphological characterization. Journal of Cell Science 103, 931–42.

Knapp, J R, Chen, W Y, Turner, N D, Byers, F M, and Kopchick, J J. 1994. Growth patterns and body composition of transgenic mice expressing mutated bovine somatotropin genes. Journal of Animal Science 72, 2812–9.

Viguerie-Bascands, N, Bousquet-Melou, A, Galitzky, J, Larrouy, D, Ricquier, D, Berlan, M, and Casteilla, L. 1996. Journal of Clinical Endocrinology and Metabolism 81, 368–75.

All patents or publications cited anywhere in this specification are hereby incorporated by reference in their entirety.

TABLE A

Human Genes regulated by Growth hormone (GH) and its antagonist in Brown Adipose Tissue

| | Gene | DNA ID | Protein ID | GHA | NT | GH |
|---|---|---|---|---|---|---|
| 1 | neuroleukin | N/A | N/A | + | | ↓ |
| | gucosephosphate isomerase | NM000175 | NP000166 | + | | ↓ |
| 2 | α-enolase | X84907 | NP001419 | + | | ↓ |
| 3 | pyruvate kinase | NM002654 | A33983/ S64635 | + | | ↓ |
| 4 | proteasome 0 chain | NM002795 | NP002786 | + | | ↓ |
| 5 | heme oxygenase | D21243 | NP002125/ P30519 | + | | ↓ |
| 6 | Ubiquitin/ ribosomal fusion protein | NM00333 | NP003324 | + | | ↓ |
| 7 | trans-Golgi network 38 | N/A | N/A | | + | ↑ |
| 8 | adipocyte lipid binding protein | NP001442/ J02874 | NP001433 | | + | ↑ |
| 9 | medium chain acyl-CoA dehydrogenase | U07159 | N/A | | + | ↑ |
| 10 | NADH-ubiquonone oxidoreductase | V00711 | P03905/ CAA24035 | | + | ↑ |
| 11 | cytochrome b | V00711 | AAC28269-88 | | + | ↑ |
| 12 | cytochrome c oxidase | V00711 | BAA07292 | | + | ↑ |
| 13 | Ng-G119K2 (Novel) | | | | + | ↑ |
| 14 | Ng-G119K15 (Novel) | | | | + | ↑ |
| 15 | Ng-G119K36 (Novel) | | | | + | ↑ |
| 16 | Ng-G119K62 (Novel) | | | | + | ↑ |

GHA: present in GH antagonist mouse cDNA substraction library (forward)
NT: present in nontransgenic mouse cDNA substraction library (reverse)
GH: presumed regulatory effect of GH on gene expression

TABLE B

Identification of Homologous Mouse/Rat Genes and Proteins

| Genes | DNA Accession # | Protein Accession # | Clone #s |
|---|---|---|---|
| glucosephosphate isomerase & neuroleukin | U89408 & M14220 | P06745 | 44 |
| a-enolase | X52379 | P17182 | 27, 141 |
| pyruvate kinase | X97047 | CAA65761 | 12 |
| proteasome theta chain | D21800 (rat) | P40112 (rat) | 19, 59 |

TABLE A-continued

Human Genes regulated by Growth hormone (GH) and its antagonist in Brown Adipose Tissue

| Gene | DNA ID | Protein ID | GHA | NT | GH |
|---|---|---|---|---|---|
| heme oxygenase | AF029874 | 2984774 or 3169816 | 128 | | |
| Ubiquitin/ribosomal fusion protein | AF118402 | S11248 | 30 | | |
| trans-Golgi network 38 | D50031, D50032 | | | 68 | |
| adipocyte lipid binding protein | K02109 or M13385 | 1ALB or P04117 | | 99, 23 | |
| medium chain acyl-CoA dehydrogenase | U07159 | | | 128 | |
| NADH-ubiquonone oxidoreductase | V00711 | P03925 | | 19 | |
| cytochrome b | V00711 | CAA24092 or CAB09443 | | 18 | |
| cytochrome c oxidase | V00711 | P00397 | | 45 | |

Underlined genes were more strongly expressed in GHA mice, and hence are down-regulated by GH (negative markers). The remaining genes were more strongly expressed in normal mice than in GHA mice, and hence are up-regulated by GH (positive markers).
DNA and protein #s are for mouse unless otherwise stated.

TABLE C

| Clone | Related Mouse Sequence | Identities |
|---|---|---|
| 44 | neuroleukin | 359/365 (98%) |
| | glucosephosphate isomerase | 265/275 (96%) |
| 27 | alpha-enolase | 520/527 (98%) |
| | | 359/363 (98%) |
| 141 | pyruvate kinase | 291/303 (96%) |
| 19 & 59 | proteasome theta | 255/268 (95%) |
| 128 | heme oxygenase | 311/317 (98%) |
| 30 | ubiquitin | 280/284 (98%) |
| 68 | trans-golgi network protein | 48/49 (97%) |
| | | 308/329 (93%) |
| 99 | adipocyte lipid binding protein | 278/286 (97%) |
| | | 211/224 (94%) |
| | | 63/65 (96%) |
| 123 | same | 355/364 (97%) |
| | | 211/224 (94%) |
| | | 103/105 (98%) |
| 127 | medium chain acyl-CoA dehydrogenase | 540/542 (99%) |
| 19 | NADH-ubiquonone oxidoreductase | 722/726 (99%) |
| 160 | same | 130/131 (99%) |
| 18 | cytochrome b | 596/598 (99%) |
| 45 | cytochrome c | 323/334 (96%) |

Table D Summary of genes regulated by Growth Hormone (GH) and GH antagonist (GHA) in Brown Adipose Tissue (BAT)

TABLE D

Summary of genes regulated by Growth Hormone (GH) and GH antagonist (GHA) in Brown Adipose Tissue (BAT)

| | Message present in PCR-Select mouse cDNA subtraction libraries | | | |
|---|---|---|---|---|
| | GHA (25) | | NT (14) | |
| Identified Gene | $f$ | IVR | $f$ | IVR |
| Bovine Growth Hormone | 14 | 21.2–∞ | | |
| α-enolase/Neuroleukin | 5 | 4.7–257.0 | | |
| Glucosphosphate Isomerase | 1 | 3.9 | | |

TABLE D-continued

Summary of genes regulated by Growth Hormone (GH) and
GH antagonist (GHA) in Brown Adipose Tissue (BAT)

| Identified Gene | Message present in PCR-Select mouse cDNA subtraction libraries | | | |
|---|---|---|---|---|
| | GHA (25) | | NT (14) | |
| | f | IVR | f | IVR |
| Pyruvate Kinase | 1 | 8.4 | | |
| Ubiquitin/ribosomal Fusion Protein | 1 | 11.2 | | |
| Proteasome θ Chain | 2 | 35.4~78.7 | | |
| Heme Oxygenase | 1 | 31.3 | | |
| Trans-Golgi Network Protein (TGN38) | | | 1 | 2.4 |
| Adipocyte Lipid Binding Protein | | | 2 | 3.6–11.5 |
| Medium Chain Scyl-CoA Dehydrogenase | | | 1 | 31.1 |
| NADH-ubiquonone Oxidoreductase | | | 2 | 7.1–12.3 |
| Cytochrome c Oxidase | | | 2 | 1.9–5.2 |
| Cytochrome b | | | 2 | 1.8–2.3 |
| Novel partial cDNAs | | | 4 | 35.2–∞ |

Table D. Summary of genes regulated by Growth Hormone (GH) & GH antagonist (GHA) in Brown Adipose Tissue (BAT) In the table, "f" indicates number of positive clones, whereas "IVR" is abbreviated from Intensity Volume Ratio estimated from library screening Dot Blots. "GHA" represents the forward subtraction library (subtracting NT mouse BAT cDNA from GHA's) 17 out of 26 sequences were found to be bGH G119K EST. 1 out of 26 was found to be a contaminant. "NT" represents the reverse subtraction library (subtracting GHA mouse BAT cDNA from NT's). 4 out of 14 were determined as novel ESTs after applying BLAST searches.

Results: Genes encoding glucosephosphate isomearse, α-enolase, pyruvate kinase, proteasome θ chain, ubiquitin, and heme oxygenase were found in the forward subtraction library, indicating that these genes are up-regulated in GHA mouse BAT. Genes encoding mitochondria cytochrome b, mitochondria cytochrome C oxidase subunit I, mitochondria NADH-ubiquinone oxidoreductase chain 4 and/or 6, medium chain acyl-CoA dehydrogenase, adipocyte lipid binding protein, and trans-Golgi network protein (TGN38) were found in the reverse subtraction library, indicating that these genes are down-regulated in GHA mouse BAT. All these GH-regulated genes may be used as potential molecular markers to help explain obesity in GHA mice.

Table 1 shows certain of the nucleotide sequences identified by subtractive hybridization against the mouse brown adipose tissue library. These are the sequences which appeared to be identical, or nearly identical, to a databank sequence. Presumably, the corresponding human genes are similarly regulated. The sequence names, sequence lengths, and the names of the most closely related databank sequences, are set forth below:

(A) G119K-Ng 44 (361 bp)(glucosephosphate isomerase; neuroleukin)
(B) G119K-Ng27 (550 bp) and G119K-Ng 141 (363 bp) (alpha-enolase)
(C) G119K-Ng12 (300 bp)(pyruvate kinase)
(D) G119K-Ng19 & 59 (299 bp)(proteasome theta chain)
(E) G119K-Ng128 (336 bp)(heme oxygenase)
(F) G119K-Ng30 (303 bp)(ubiquitin)
(G) G119K-Ng68 (345 bp)(trans-Golgi network protein)
(H) G119K-Ng99 (313 bp) and G119K-Ng123 (374 bp) (adipocyte lipid binding protein)
(I) G119K-Ng127 (542 bp)(medium chain acyl-CoA dehydrogenase)
(J) G119K-Ng19 (725 bp) and 160 (131 bp) (NADH-ubiquinone oxireductase)
(K) G119K-Ng45 (343 bp)(cytochrome c oxidase)

For each sequence, the complete clone sequence, and the highest scoring BLAST alignment, are given.

Table 2 (a) shows the sequences of Ng-G119K42, and (as boldfaced subsequence) Ng-G119K36. (B) shows ORF.

The ORF of clone 42 spanning from nucleotide 112 through 1152 is believed to encode a 346 amino acid long polypeptide, which possesses a predicted cleavage site most likely between residue Q18 and P19 based on the output of Signal V1.1 World Wide Web Server (http://www.cbs.dlu.dlk/services/SignalP/).

The clone 42 protein has a theoretical Molecular Weight of 37.2751 Kda, theoretical Isoelectric Point of 9.82, 97.05 in aliphatic index, and 0.382 in grand average of hydropathicity, by ProtParam tool (http://www.expasy.ch/tools/protparam.html).

The secondary structure prediction for clone 42 suggests an all-helices protein which contains 38.44% for α-helix, 22.54% for extended strand, 12.72% for β-turn, and 26.30% for random coil, by the SOPM method (http://pbil.ibcp.fr/egi-bin/npsa_sopm.html) [Geourjon, C. & Deleage, G., SOPM: a self optimised method for protein secondary structure prediction, Protein Engineering (1994) 7, 157–164]. By the SOPMA method (http://pbil.ibcp.fr/cgi-bin/npsa_automat.pl?page=npsa_sopma.html), we get 51.73% for α-helix, 16.18% for extended strand, 5.49% for β-turn, and 26.59% for random coil.

The polypeptide encoded by clone 42 may have 6–8 transmembrane (TM) regions, based on the output from "DAS"-Transmembrane Prediction server (http://www-.biokemi.su.se-server/DAS/). Depended on the criteria applied for prediction, several other free public servers suggest 6 TM, see TMHMM (v. 0.1) program (http://www-w.cbs.dtu.dk/services/TMHMM-1.0/), 7 TM by TopPred 2 program (http://www.biokemi.su.se/-server/toppred2/toppredServer.cgi), or 8 TM, see Tmpred program (http://www.ch.embnet.org/software/TMPRED-form.html).

The Tmpred program makes a prediction of membrane-spanning regions and their orientation. The algorithm is based on the statistical analysis of Tmbase, a database of naturally occurring transmembrane proteins. The prediction is made using a combination of several weight-matrices for scoring.

No suitable target has been found in searching sequences of known 3D structures from the SWISS-MODEL Protein Modelling Server (http:/www.expasy.ch/swissmod/SWISS-MODEL.hlml). However, the protein folding encoded by clone 42 is suggested as being similar to a membrane and cell surface protein and peptide, such as bacteriorhodopsin (0.465 of SAWTED E-value and 0.364 of PSSM E-value) at low significant level, based on the Program 3D-PSSM (http://www.bmm.icnel.uk/-3dpssm/) which has a capacity to recognize protein fold using 1D and 3D sequence profiles coupled with secondary structure information (Foldfil).

Potential type O-glycosylation sites S186, T163, and T269 are predicted from NetOGlyc 2.0 Prediction Server (http://www.cbs.dlu.dk/services/NclOGlycl) which produces neural network predictions of mucin type GalNAc O-glycosylation sites in mammalian proteins. Potential phosphorylations sites at S71, S127, S182, T50, T54, T59, T306, T322, Y46, and Y183 are predicted from the NetPhos www server (http: //www.cbs.dlu.dk/services/NetPhos/) which produces neural network predictions for serine, threomine and tyrosine phosphorylation sites in eukaryotic proteins.

Results: Predicted secondary structure of clone 42 seems a helix-like polypeptide with a 18-amino acid signal peptide and relatively low hydrophobicity value. Predicted tertiary structure of clone 42 is a protein with a 6–8 hydrophobic regions through the sequence, leading to a folding model similar to bacteriorhodopsin, which is a important protein for proton conductance in archaebacteria.

Applying the advanced version of Blast search with a controlled expect value below 0.0001, 12 bits have been found matchable to the sequence of clone 42 in positive sense strand at amino acid level. Among them, three sequences from Genebank database share a protein homogy at a very significant level as listed in this figure: C25077 gene product from female human infant brain with an expect value $1.0 \times 10^{-170}$, PTD010 gene product from human pituitary tumor with an expect value $1.0 \times 10^{-147}$, and CG1287 gene product from drosophila melanogaster with an expect value $4.0 \times 10^{-73}$. The C25077 gene product from female human infant brain possesses a same size of deduced polypeptide as DERP2. Clone 42-encoded polypeptide shares 86% (2980aa out of 346-aa) identities and 90% (313-aa out of 346 -aa) positives to C25077 gene product, 74% (256-aa out of 346-aa) identities and 77% (268-aa out of 346-aa) positives to PTD010 gene product, and 40% (139-aa out of 346-aa) identities and 54% (188-aa out of 346-aa) positives to CG1287 gene product.

Results: Since the PTD010 is missing the C-terminal portion of sequence which remains intact in C25077 and Clone 42, it suggests that the C-terminal region may be important for normal biological function.

At the nucleic acid level, applying the advanced version of BLAST search with a controlled expect value below 0.0001, many genes have been found matchable beyond the nucleotide position 1794 in positive sense stand of clone 42. They span approximately 100-bp. However, a few of matched sequences exhibited similarity from 5' end through most part of clone 42 with a zero expect value, such as C25077 gene (345-aa) of female human infant brain, PTD010 gene product from human pituitary tumor, and human dermal papilla derived protein 2 gene (DERP2). DERP2 is identical to C25077. Along with their matched portion, clone 42 shares 90% homology with both sequences, 946-bp out of 1049-bp for C25077 or 945-bp out of 1049-bp for PTD010.

Table 3 shows the sequences of (a) Ng-G119K58, (b) Ng-G119K65, (c) Ng-G119K66, and the alignment of EST NG-G119K62 with each of (a)–(c). 3(d) shows the triple alignment of (a), (b) and (c). 3(e) shows ORF of greatest interest.

Clones 58, 65, and 66 are 1379-bp, 2437-bp, and 1613-bp long mRNA respectively and have 3 ORFs, 7 ORFs, and 3 ORFs respectively. 5 out of total 9 OFRs are derived from positive strand of cDNAs: 1 specific to clone 65, 2 specific to clone 65 and 66, and 2 specific to clone 58, 65 and 66. The sequence of Reverse 62 completely matches all these three clones at 3' end which is upstream of the multiple polyadenylational tail signals (AAUAAA). Additional polyadenylational signal sequence is unusually seen in 5' end of clone 65, but whole context suggests it may not functional.

Clone 58, 65, and 66 seem like triple alternative splice forms which are 1379-bp, 2436-bp, 1612-bp mRNAs respectively, which support the prediction by sequence analyses of these clones. Because multiple bands were observed under prolonged exposure, other unknown spliced forms may exist in this gene family. Messages from ORF region encoded multiple sequences and clone 65 itself seem negatively regulated by GH at transcriptional level in mouse BAT.

Applying the advanced version of Blast search with a controlled expect value below 0.000.1, many genes have been found matchable beyond the nucleotide position 1203 for clone 58, 1856 for clone 65, and 1437 for clone 66 in antisense strand for these cDNAs. However, in positive sense strand, only human DNA sequence from clone 415G2 on chromosome has been matched to clone 58 with an expect value $3.0 \times 10^{-50}$, to clone 65 with an expect value $6.0 \times 10^{-50}$, and to clone 66 with an expect value $4.0 \times 10^{-50}$ as indicated in A and B. These alignment searches suggest that all these three isoforms share a common open reading frame which encodes 86 amino acids.

Table 4 Shows the Sequences of (a) Ng-G119K2, First Strand and Second Strand and (b) Ng-G119K15 First Strand and Second Strand.

Applying the advanced version of BLAST search with a controlled expect value below 0.0001, the polypeptide sequence of clone 58 shares 49% (42-aa out of 86-aa) identities, 77% (66-aa out of 86-aa) positives with CG6115 gene product of Drosophila melanogaster with an expect value $1.0 \times 10^{-16}$ for clone 58 and $2.0 \times 10^{-16}$ for both clone 65 and 66, though there is no similarity at nucleic acid sequence level. This output further supports the prediction of ORF. Additionally, DNA sequence homology only occurs between human and mice, not between mice and fruit fly, suggesting a evolutionary role within these species.

Table 5 Shows the Sequence of Ng62D'4-2-1-4 cDNA.

TABLE 1 mouse glucosephosphate isomerase & neuroleukin
partial (+) strand cDNA Open Reading Frame
G119K-Ng 44 sequence (361 bp) (SEQ ID NO:8):
CTCTTTATAATCGCCTCCAAGACCTTCACCACCCAGGAGACCATCACCAATGCAGAGACA

GCAAAGGATGGTTTCTCGAAGCGGCCAAGATCCATCTGCAGTTGCAAAGCACTTTGTCGC

CCTGTCTACGAACACGGCCAAAGTGAAAGAGTTTGGAATTGACCCTCAAAACATGTTCGA

GTTCTGGGATTGGGTAGGTGGCCTATTCGCTGTGGTCAGCCATTGGACTTTCCATTGCTC

TGTATGTAGGTTTTGACCACTTCGAGCAGCTGCTGTCCGGGGCTCACTGGATGGACCTGC

TABLE 1-continued

```
ACTTCCTCAAGACGCCCCTGGAGAAGAATGCCCCCGTCCTGCTGGCTCTACTGGGCATCT

G

Sequence 1 1c11G119k-Ng 44        Length 361 from: 1 to = 361
Sequence 2 gi 200064              Mouse neuroleukin mRNA, complete cds.
                                  Length 1985 from: 1 to +1985
NOTE: The statistics (bitscore and expect value) is calculated based on
the size of nr database
Score = 639 bits (332), Expect = 0.0
Identities = 359/365 (98%), Positives = 359/365 (98%), Gaps = 4/365 (1%)
Aligned query 1-361 to subject 665-1029.
Sequence 1 G119K-Ng 44            Length 361 from: 1 to = 361
Sequence 2 gi 3642648             Mus musculus strain BALB/c glucosc-6-phosphate
                                  isomerase mRNA, partial cds.
                                  Length 477 from: 1 to = 477
Score = 462 bits (240), Expect = e-128
Identities = 265/275 (96%), Positives = 265/275 (96%), Gaps = 2/275 (0%)
Aligned query 89-361 to subject 1-275.

2. mouse α-enolase
partial (+) strand cDNA Open Reading Frame
G119K-Ng 27 sequence (550 bp) (SEQ ID NO:9):
ACGCGGAAGCAGTGGTAACAACGCAGAGTACACCGCAAAAGGTCTCTTCCG

AGCTGCGGTGCCCAGCGGTGCGTCCACTGGCATCTACGAGGCCTAGAACTC

CGAGACAATGATAAGACCCGCTTCATGGGGGAAGGGTGTCTCACAGGCTGTT

GAGCACATCAATAAAACTATTGCGCCTGCTCTGGTTAGCAAGAAAGTGAATG

TTGTGGAGCAAGAGAAGATTGACAAGCTGATGATCGAGATGGACGGCACAGA

GAATAAATCTAAATTTGGTGCAAATGCCATCCTGGGAGTGTCCCTGGCTGTC

TGCAAAGCTGGTGCCGTGGAAAAGGGGTGCCCCTTTACCGCCACATTGCTGA

CTTGGCCGGCAACCCTGAAGTCATCCTGCCTGTCCCGGCTTTCAATGTGATC

AACGGTGGTTCTCATGCTGGCAACAAAGCTGGCCATGCAAAGAGTTCATGAT

CCTGCCTGTGGGGCATCCAGCTCCGGGAAGCCATGCGCATTGGAGCAGAGGT

TTACCACAACCTGAAGAACGTGATCAAGGAGA

Sequence 1 G119K-Ng 27            Length 550 from: 1 to = 550
Sequence 2 gi 55490               Mouse mRNA for alpha-enolase (2-phospho-D-
                                  glycerate hydrolase) (EC 4.2.1.11)
                                  Length 1720 from: 1 to = 1720
Score = 906 bits (471), Expect = 0.0
Identities = 520/527 (98%), Positives = 520/527 (98%), Gaps = 7/527 (1%)
Aligned query 28-550 to subject 167-690.
G119K-Ng 141 sequence (363 bp) (SEQ ID NO:10):
ACAAGTCCTTCGTCCAGAACTACCCAGTGGTGTCCATCGAAGATCCCTTTGA

CCAGGACGACTGGGGCGCCTGGCAGAAGTTCACGGCTAGTGCGGGCATCCAG

GTGGTGGGCGATGACCTCACAGTGACCAACCCTAAGCGGATTGCCAAGGCTG

CGAGCGAGAAGTCCTGCAACTGCCTCTTGCTCAAAGTGAACCAGATCGGCTC

TGTGACCGAATCCCTGCAGGCGTGTAAGCTGGCCCAATCCAATGGCTGGGGT

GTCATGGTGTCCCACCGATCTGGGGAAACTGAGGACACTTTCATCGCAGACC

TGGTGGTGGGGCTCTGCACTGGGCAGATCAAGACTGGTGCCCCTTGCCGAT

Sequence 1 G1119K-Ng 141          Length 363 from: 1 to = 363
Sequence 2 gi 55490               Mouse mRNA for alpha-enolase (2-phospho-D-
                                  glycerate hydrolase) (EC 4.2.1.11)
                                  Length 1720 from: 1 to = 1720
Score = 675 bits (351), Expect = 0.0
Identities = 359/363 (98%), Positives = 359/363 (98%)
Aligned query 1-360 to subject 934-1293.
```

TABLE 1-continued 3. mouse pyruvate kinase
partial (+) strand cDNA Open Reading Frame
G119K-Ng 12 sequence (300 bp) (SEQ ID NO:11):
CATGCAGAGACCATCAAGAATGTCCGTGAAGCCACAGAAAGCTTTGCATCTG

ATCCCATTCTCTACCGTCCTGTTGTGGTGGCTCTGGATACAAAGGGACCTGA

GATCCGGACTGGACTCATCAAGGGCAGCGGCACCGCTGAGGTGGAGCTGAAG

AAGGGAGCCACTCTGAAGATCACCCTGGACAAGCTTACATGGAGAAGTGTGA

CGAGAACATCCTGTGGCTGGACTACAGACATCTGCAAGGTGTGAGTGGCAGC

AAGATCTACGTGGACGATGGCTCATCTCACTGCAGTGAAG

Sequence 1 G119K-Ng 12           Length 300 from: 1 to 300
Sequence 2 gi 1405932      M.musculus mRNA from M2-type pyruvate kinase
                           Length 2134 from: 1 to = 2134
Score = 465 (242), Expect = e–129
Identities = 291/303 (96%), Positives = 291/303 (96%), Gaps = 8/303 (2%)
Aligned query 1–295 to subject 256–558.

4. mouse proteasome θ chain
partial (+) strand cDNA Open Reading Frame
G119K-Ng 19 & 59 sequence (299 bp) (SEQ ID NO:12):
GCGGGGACTCCAGCGCAATCATGTCTATTATGTCCTATAATGGAGGGGCCGT

CATGGCATGAAGGGAAAGAACTGTGTGGCCATCGCTGCAGACAGACGTTTCG

GGATCCAGGCCCAGATGGTGACCACGGACTTCCAGAAGATCTTTCCCATGGG

TGACAGGCTCTACATAGGCCTGGCCGCCTGGCCACTGACGTCCAGACAGTTG

CCCAGCGTCTCAAGTTCCGACTGAACTTGTATGAGCTGAAGAAGGTCGACAG

ATCAGCCTTACACCTACTGAGACTGGTGGCACTCTGTAT

Sequence 1 G119K-Ng 19 & 59     Length 299 from: 1 to = 299
Sequence 2 gi 458730        Rat mRNA for proteasome subunit RC10-II, com-
                            plete
                            cds.
                            Length 828 from: 1 to 828
Score = 402 bits (209), Expect = e–110
Identities 255/268 (95%), Positives = 255/268 (95%), Gaps = 4/268 (1%)
Aligned query 11–274 to subject 68–335.

5. mouse heme oxygenase
partial (+) strand cDNA Open Reading Frame
G119K-Ng 128 sequence (336 bp) (SEQ ID NO:13):
TCCAGTTGTCAAGACTTCTTGAAGGAAACATTAAGAAGGAGCTATTTAAGAT

GGCACCACTGCACTTTACTTCACATACTCAGCCCTTGAGAGGAATGGACCGC

AACAAGGACACCCAGCCTTCGCCCCCTTATATTTCCCCACGGAGCTACACCG

GAAGGCAGCACTGATCAAGGACATGAAGTATTTCTTTGGTGAAAACTGGGAG

GAGCAGGTGAAGTGCTCTGAGGCTGCCCAGAAGTATGTGGATCGGATTCACT

ATGTAGGGCAAAATGAGCCAGAGCTGCTGGTGGCCCATGCTTATACTCGTTA

CATGGGGGACTTTCAGGGGGTTAG

Sequence 1 G119K-Ng 128         Length 336 from: 1 to = 336
Sequence 2 gi 2984773           Length 1255 from: 1 to = 1255
Score = 527 bits (274), Expect = e–148
Identities = 311/317 (98%), Positives = 311/317 (98%), Gaps = 5/317 (1%)
Aligned query 22–303 to subject 1–284.

6. mouse ubiquitin
partial (+) strand cDNA Open Reading Frame
G119K-Ng 30 sequence (303 bp) (SEQ ID NO:14):
GGGCTTTCTCTTCAACGAGGCGGCCGAGCGGCAGACGCCAACATGCAGATCT

TCGTGAAGACCCTGACGGGCAAGACCATCACTCTTGAGGTCGAGCCCAGTGAC

ACCATCGAGAATGTCAAGGCCAAGATCCAAGACAAGGAAGGCATCCCACCTG

TABLE 1-continued

ACCAGCAGAGGCTGATATTCGCGGGCAAACAGCTGGAGGATGGCCGCACCCT

GTCCGACTACAACATCCAGAAAGAGTCCACCTTCGACCTGGTGCTGCGTCTG

CGCGGTGGCATCATTGAGCCATCCTTCGTCAGCTTGCCCAGAA

```
Sequence 1 G119K-Ng 30       Length 303 from: 1 to = 303
Sequence 2 gi 4262554        Length 500 from: 1 to = 500
Score = 504 bits (262), Expect = e-141
Identities = 280/284 (98%), Positives = 280/284 (98%), Gaps = 2/284 (0%)
Aligned query 22-303 to subject 1-284.
```

7. mouse Trans-Golgi Network protein (TF_GN38)
partial (+) strand cDNA
Ng-G119K 68 sequence (345 bp) (SEQ ID NO:15):
TAGCATAAAAGGGACTCGAGGTTTCTGAAAGTAAAATCACTGTTTGATGGGA

TTTTTTAAAAAAATGATCATTGAACAAGTGTGTTCTTGCATACATTCACCCC

AATAAGGGCTTCCTGGAAAGGGACAGGTTCATGCTTTGTGGAAGAAAACACA

TAGGAGGGATTTAGTATGCAGGAAAGAGGTTTTCTACAAATTGAGTTTTGCT

TTTATTGCCCGCAGTAGATAGATATTTAGAAACTAACTGCATTCTTCACACT

CCTCCTTGCTGTTTAAGATGTGCAGGATAGGAAATCTTCCTATCCTGTCATA

TCTGGTCATGAACTGTAGAACTAATAGTCCTGA

```
Sequence 1 Ng-G119K 68       Length 345 from: 1 to = 345
Sequence 2 gi 949828         Mouse mRNA for TGN38A, complete cds.
                             Length 1673 from: 1 to = 1673
Score = 89.1 bits (46), Expect = 3e-16
Identities = 48/49 (97%), Positives = 48/49 (97%)
Aligned query 1-49 to subject 1625-1673.
Sequence 1 Ng-G119K 68       Length 345 from: 1 to = 345
Sequence 2 gi 949830         Mouse mRNA for TGN38B, complete cds.
                             Length 2265 from: 1 to = 2265
Score = 487 bits (253), Expect = e-136
Identities = 308/329 (93%), Positives = 308/329 (93%), Gaps = 6/329 (1%)
Aligned query 1-324 to subject 1656-1983.
```

8. mouse adipocyte lipid binding protein
partial (+) strand cDNA Open Reading Frames
Ng-G119K 99 sequence (313 bp) (SEQ ID NO:16):
GCAGAAGTGGGATGGAAAGTCGACCACAATAAAGAGAAAACGAGATGGTGAC

AAGCTGGTGGTGGAATGTGTTATGAAAGGCGTGACTTCCACAAGAGTTTATG

AAAGGGCATGAGCCAAAGGAAGAGGCCTGGATGGAAATTTGCATCAAACACT

ACAATAGTCAGTCGGATTTATTGTTTTTTTTAAAGATATGATTTTCCACTAA

TAAGCAAGCAATTAATTTTTTCTGAAGATGCATTTTATTGGATATGGTTATG

TTGATTAAATAAAACCTTTTTAGACTCAAAAAAAAAAAAAAAAAAAAAAGG

T

```
Sequence 1 Ng-G119K 99       Length 313 from: 1 to = 313
Sequence 2 gi 198716         Mouse 3T3-L1 lipid binding protein mRNA, com-
                             plete
                             cds.
                             Length 614 from: 1 to = 614
Score = 519 bits (270), Expect = e-146
Identities = 278/286 (97%), Positives = 278/286 (97%)
Aligned query 1-286 to subject 328-613.
Sequence 1 G119K-Ng 99       Length 313 from: 1 to = 313
Sequence 2 gi 198718         Mouse adipocyte lipid binding protein gene,
                             complete cds.
                             Length 5212 from: 1 to = 5212
Score = 333 bits (173), Expect = 9e-90
Identities = 211/224 (94%), Positives = 211/224 (94%), Gaps = 4/224 (1%)
Aligned query 64-286 to subject 4490-4710.
Score = 114 bits (59), Expect = 8e-24
Identities = 63/65 (96%), Positives = 63/65 (96%)
Aligned query 1-65 to subject 3760-3824.
```

TABLE 1-continued

Ng-G119K 123 sequence (374 bp) (SEQ ID NO:17):
GAATTCGATGAAATCACCGCAGACGACAGGAAGGTGAAGAGCATCATAACCC

TAGATGGCGGGGCCCTGGTGCAGGTGCAGAAGTGGGATGGAAAGTCGACCAC

AATAAAGAGAAAACGAGATGGTGACAAGCTGGTGGTGGAATGTGTTATGAAA

GGCGTGACTTCCACAAGAGTTTATGAAAGGGCATGAGCCAAAGGAAGAGGCC

TGGATGGAAATTTGCATCAAACACTACAATAGTCAGTCGGATTTATTGTTTT

TTTTTAAAGATATGATTTTCCACTAATAAGCAAGCAATTAATTTTTTCTGAA

GATGCATTTTATTGGATATGGTTATGTTGATTAAATAAAACCTTTTTAGACT

CAAAAAAAAA

Sequence 1 Ng-G119K 123          Length 374 from: 1 to = 374
Sequence 2 gi 198716       Mouse 3T3-L1 lipid binding protein mRNA, com-
                           plete
                           cds.
                           Length 614 from: 1 to = 614
Score = 654 bits (340), Expect = 0.0
Identities = 355/364 (97%), Positives = 355/364 (97%), Gaps = 1/364 (0%)
Aligned query 1–364 to subject 251–613.
Sequence 1 Ng-G119K 123          Length 374 from: 1 to = 374
Sequence 2 gi 198718       Mouse adipocytc lipid protein gene, complete
                           cds.
                           Length 5212 from: 1 to = 5212
Score = 344 bits (179), Expect = 4e–93
Identities = 211/224 (94%), Positives = 211/224 (94%), Gaps = 3/224 (1%)
Aligned query 141–364 to subject 4490–4710.
Score = 191 bits (99), Expect = 7e–47
Identities = 103/105 (98%), Positives = 103/105 (98%)
Aligned query 38–142 to subject 3720–3824.
Score = 75.7 bits (39), Expect = 4e–12
Identities = 39/39 (100%), Positives = 39/39 (100%)
Aligned query 1–39 to subject 3097–3135.

9. mouse medium chain acyl-CoA dehydrogenase
partial (+) strand cDNA
Ng-G119K 127 sequence (542 bp) (SEQ ID NO:18):
GAGGCTGATCATAGCTCGTGAGCACATTGAAAAGTATAAAAATTAACAGGA

ATTACTATTGAACGATGCATCACCCTCGTGTAACTAAGCTCCAAGCACTGT

TGCTGCTTCAGGGGAAAAGGGCTTTACTGTCTTCCCAAGGAAATGAGATCAA

AGACGAGTTTGGATCTGTGCAGCGGATTCCCATGGCGGAGGAACCTGTCTTC

AGCTCTATGGTGACCCTTTCTAGATAGGTTTGGCTTTTGGACAATGATTGGT

CCTTAGCCCCGAATTGTGTTAGTTTGCTCTTTGATCACTTAAAATGGAAAAA

CACCCTGGACTTTTAATGTTCATTCAAGTGACAGGAAAGGCGGCTTGTCAAG

GAAGAACTCATGATTCTAACATAAACACTGAAAATTTGTGGTAGATTGGACA

CGTCAGACTGTGACATAGCAGCATTTCTGTGCTGAACTGTTAATTTTATAAT

TTTGATTATATTTGCTTTGTTTTGCACAAAAGAGTAAAAAGTTTATATTCAC

ATTCTCCCATTATAAAACTAAAAC

Sequence 1 Ng-G119K 127          Length 542 from: 1 to = 542
Sequence 2 gi 463908       *Mus musculus* medium-chain acyl-CoA dehydrogenase
                           mRNA, complete cds.
                           Length 1846 from: 1 to = 1846
Score = 1021 bits (531), Expect = 0.0
Identities = 540/542 (99%), Positives = 540/542 (99%), Gaps = 1/542 (0%)
Aligned query 1–542 to subject 1228–1768.

10. mouse NADH-ubiquonone oxidoreductase
partial (+) strand cDNA Open Reading Frame from
mitochondria genome
Ng-G119K 19 sequence (725 bp) (SEQ ID NO:19): chain 4
GATCCGTTCGTAGTTGGAGTTTGCTAGGCAGAATAGGAGTGATGATGTGAG

GCCATGTGCGATTATTAGTATTGTTGCTCCTATGAAGCTTCATGGAGTTTG

TABLE 1-continued

```
GATTATGATTGATGCAATAACAAGTGCTATGTGGCTAACTGAGGAGTAGGC

GATTAGTGATTTTAAATCTGTTTGGCGTACAGAGATTGAGCTAGTTATAAT

TATTCCTCATAGGGAGAGAAGGATGAAGGGGTATGCTATATATTTTGTTAG

TGGGTCTAGAATAATGGAGATGCGAATTATTCCGTAACTACCTAATTTTAG

AAGAATAGCTGCTAGAATTATTGACCCAGCAATTGGAGCTTCAACATGGGCT

TTTGGTAGTCATAGGTGAACTCCATATAATGGTATTTTAATAAGAAATGCTA

TTATGCATGCCAACCATAGTAAGTTGTTAGATCATGAAGCGTCTAAGGTGTG

TGTTGTGAATGATAAAATTATGAGGTTTAGGGTTCCTACATGGTTTTGGATT

AAGATGAGGGCAATTAGCAGTGGAATAGAACCGATTAGGGTATAAAATAGGA

AATAAATCCCTGCGTTTAGGCGTTCAGTTTGGTTCCTCATCGGGTAATAATA

ATAAGTGTTGGGATTAAGGTTGCTTCAAATAAAATATAAAATATAATTAGTT

CAGTTGCTGAAAAGGTTATGATTAGGAGAATTTGTAAGCTGATTAGTATTGA

GAT

Sequence 1 Ng-G119K 19      Length 725 from: 1 to = 725
Sequence 2 gi 13838         Mus musculus mitochondrial genome
                            Length 16295 from: 1 to = 16295
Score = 1363 bits (709), Expect = 0.0
Identities = 722/726 (99%), Positives = 722/726 (99%), Gaps = 1/726 (0%)
Aligned query 1–725 to subject 11171–10446.
Ng-G119K 160 sequence (131 bp)(SEQ ID NO:20): chain 6
ATACTCAATTAATCTCGAGTAATCTCGATAATAATAAAAGATACCCGCAAAC

AAAGATCACCCAGCTACTACCATCATTCAAGTAGCACAACTATATATTGCCG

CTACCCCAATCCCTCCTTCCAACATAA

Sequence 1 Ng-G119K 160     Length 131 from: 1 to = 131
Sequence 2 gi 13838         Mus musculus mitochondrial genome.
                            Length 16295 from: 1 to = 16295
Score = 237 bits (123), Expect = 3e–61
Identities = 130/131 (99%), Positives = 130/131 (99%), Gaps = 1/131 (0%)
Aligned query 1–131 to subject 13538–13667.

11. mouse cytochrome b
partial (+) strand cDNA Open Reading Frame from
mitochondria genome
Ng-G119K 18 sequence (599 bp) (SEQ ID NO:21):
GAGTCATAGCCACAGCATTTATAGGCTACGTCCTTCCATGAGGACAAATAT

CATTCTGAGGTGCCACAGTTATTACAAACCTCCTATCAGCCATCCCATATA

TTGGAACAACCCTAGTCGAATGAATTTCAGGGGGCTTCTCAGTAGACAAAG

CCACCTTGACCCGATTCTTCGCTTTCCACTTCATCTTACCATTTATTATCGC

GGCCCTAGCAATCGTTCACCTCCTCTTCCTCCACGAAACAGGATCAAACAAC

CCAACAGGATTAAACTCAGATGCAGATAAAATTCCATTTCACCCCTACTATA

CAATCAAAGATATCCTAGGTATCCTAATCATATTCTTAATTCTCATAACCCT

AGTATTATTTTTCCCAGACATACTAGGAGACCCAGACAACTACATACCAGCT

AATCCACTAAACACCCCACCCCATATTAAACCCGAATGATATTTCCTATTTG

CATACGCCATTCTACGCTCAATCCCCAATAAACTAGGAGGTGTCCTAGCCTT

AATCTTATCTATCCTAATTTTAGTCCTAATACCTTTCCTTCATACCTCAAAG

CAACGAAGCCTAATATTCCGCCCAATCACA

Sequence 1 Ng-G119K 18      Length 599 from: 1 to = 599
Sequence 2 gi 13838         Mus musculus mitochondrial genome.
                            Length 16295 from: 1 to = 16295
Score = 1138 bits (592), Expect = 0.0
```

TABLE 1-continued

Identities = 596/598 (99%), Positives = 596/598 (99%)
Aligned query 2-599 to subject 14504-15101.

12. mouse cytochrome c oxidase
partial (+) strand cDNA Open Reading Frame from
mitochondria genome
Ng-G119K 45 sequence (343 bp) (SEQ ID NO:22):
TCCAGCTATACTATGAGCCTTAGGCTTATTTCTATTACAGTTGGTGGTCTAA

CCGGAATGTTTATCCAACTCATCCCTTGACATCGTGCTTCACGATAACATAC

TATGTAGTAGCCCATTTCCACTATGTTCTATCAATGGGAGCAGTGTTTGCTA

TCATAGCAGGATTTGTTCACTGATTCCCATTATTTTCAGGCTTCACCCTAGA

TGACACATGAGCAAAAGCCCACTTCGCCATCATATTCGTAGGAGTAAACATA

ACATTCTTCCCTCAACATTTCCTGGGCTTTCAGGAATACCACGACGCTACTC

AGACTACCCAGATGCAAAAAAAAAAAAAAAA

Sequence 1 1c11seq_1          Length 343 from: 1 to = 343
Sequence 2 gi 13838           *Mus musculus* mitochondrial genome.
                              Length 16295 from: 1 to = 16295
Score = 531 bits (276), Expect = e-149
Identities = 323/334 (96%), Positives = 323/334 (96%), Gaps = 8/334 (2%)
Aligned query 1-327 to subject 6332-6664.

TABLE 2A mouse Brown Adipose Tissue Reverse (NT-GHA) 36 cDNA
(EST); 463 BP. (in bold)
mouse Brown Adipose Tissue Clone 42 cDNA (full-length);
2475 BP (SEQ ID NO:23).
Start Codon: 112 (underlined)
Stop Codon: 1152
Open Reading Frame: 346-aa

| | | | | |
|---|---|---|---|---|
| GAGAGGGAGG | TCGCACACTC | TGAGTTTCGG | TGACCCGGAA | GGAGCCCCGT |
| GGTAGAGGTG | ACCGGAGCTG | AGCATTTCAG | ATCTGCTTAG | TAAACCGGTG |
| TATCGCCCAC | C<u>ATG</u>TTGGCT | GCAAGGCTTG | TGTGTCTCCG | GACACTACCT |
| TCCAGGGTTT | TCCAGCCCAC | TTTCATCACC | AAGGCCTCTC | CACTTGTGAA |
| GAATTCCATC | ACAAAGAACC | AATGGCTCGT | AACACCCAGC | AGGGAATATG |
| CTACCAAGAC | AAGAATTAGG | ACTCACCGTG | GGAAAACTGG | ACAAGAACTG |
| AAAGAGGCAG | CCAAGGAACC | ATCAATGGAA | AAAATCTTTA | AAATCGATCA |
| AATGGGAAGG | TGGTTTGTTG | CTGGAGGAGC | AGCTGTTGGT | CTTGGAGCGC |
| TCTGCTACTA | TGGCTTGGGA | ATGTCTAATG | AGATTGGAGC | TATCGAAAAG |
| GCTGTAATTT | GGCCTCAGTA | TGTAAAGGAT | AGAATTCATT | CTACTTACAT |
| GTACTTAGCA | GGAAGTATTG | GTTTAACAGC | TTTGTCTGCC | TTGGCAGTAG |
| CCAGAACACC | TGCTCTCATG | AACTTCATGA | TGACAGGCTC | TTGGGTGACA |
| ATTGGTGCGA | CCTTTGCAGC | CATGATTGGA | GCTGGAATGC | TTGTACACTC |
| AATATCATAT | GAGCAGAGCC | CAGGCCCAAA | GCATCTGGCT | TGGATGCTGC |
| ATTCTGGTGT | GATGGGTGCA | GTTGTGGCTC | CTCTGACGAT | CTTAGGGGGG |
| CCTCTTCTCC | TGAGAGCCGC | ATGGTACACC | GCTGGTATTG | TGGGAGGCCT |
| CTCTACTGTG | GCCATGTGTG | CGCCTAGTGA | GAAGTTTCTG | AACATGGGAG |
| CACCCCTGGG | AGTGGGCCTG | GGTCTTGTCT | TTGCGTCTTC | TCTGGGTCT |
| ATGTTTCTTC | CCCCTACCTC | TGTGGCTGGT | GCCACTCTGT | ACTCAGTGGC |

TABLE 2A-continued mouse Brown Adipose Tissue Reverse (NT-GHA) 36 cDNA
(EST); 463 BP. (in bold)
mouse Brown Adipose Tissue Clone 42 cDNA (full-length);
2475 BP (SEQ ID NO:23).
Start Codon: 112 (underlined)
Stop Codon: 1152
Open Reading Frame: 346-aa

AATGTATGGT GGATTAGTTC TTTTCAGCAT GTTCCTTCTG TATGATACTC

AGAAAGTAAT CAAACGTGCA GAAATAACAC CCATGTATGG AGCTCAAAAG

TATGATCCCA TCAATTCGAT GTTGACAATC TACATGGATA CATTAAATAT

ATTTATGCGA GTTGCAACTA TGCTAGCAAC TGGAAGCAAC AGAAAGAAAT

GAAGTAACCG CTTGTGATGT CTCCGCTCAC TGATGTCTTG CTTGTTTAAT

AGGAGCAGAT AGTCATTACA GTTTGCATCA GCAGAATTCC TTGAGGTTTA

GAAGATAGCC TGTCACCATG TTTAAAATGT GCAGTAATGC GACCCTTCAG

GCATGCCTTT TCTTTTAGAA AATAAATGCA ATAGATGTCT TCCAAATATA

TTTTCATCTC TTATGCTTTC ATACTTTAAA ACTGCTTTGA TGAATGTGTG

AACAAATATA TTTTAGAAGA TTTCAAGTAT TGTTTTATGT ATTGGATAAG

TAAAATTTAG CAAATTTGCG TGTCTTCATA TTGTGGAAGC CTGCAGAATA

TTTCAGTGGC ATCATGAGTG ACAAGTTTTT TGTATAGAGG TCAGAGAGAT

AAAAGGCACC TGCAGTCAGT TTGAATGCCC AGGACAACAC TGATTGTGGT

GAGCCAGTGA AAGACATCAG AGATGTGGAA CAAGGGACCA CCAAATGTGG

GGTTAACAAA GACACGGATG TTTCTTCTGT GCTCTTAATG TCCTTGAGGT

TGACTGCTCA TTGTCAGGAC AGTCCAGAGT GTTAACCATA CAGAGAATCT

CTGCTGGAAT TATGTCTGTG TTTTACTATG AAGTCTTTAG AACAAGCAGG

TTGGTGGTGG CGCACACCTT TAGTCCCATC ATCTGGGAGG CAGAGGCAAG

CAGATCTCTA AATTCAAGGC CAGCCAGGTC TACAAAGTGA GTTCCAAGCC

AGACAAGGAC CTGTCTCTAA TACAAGCAAA CAAACAACAA CAAACACTAC

CGCTATGCTC GGTATGATGT ACTACTCCAA AGCTCAAGAC TCCTTTGCTG

TCAGATGTGT GGTGTATATG CAGTTGGACA GGATTTAGGT TTTGGTTTTT

GGTTTTGTTT TATTTTGATA TTTTTCTCAG TGTCTAATTG AAAGCATGCT

TGCTTTCTCA TCACAGCTTT GACAGCTGTC AGAAAAGCCT CTTTGTGGCT

TATGCTAAGA TTAGGATTGG TTTTTCTTCT AAAACTGTTG GCTTCCTCCG

TTCCCTCTCA GCTTAAGCAT GAACAAAGCA AATTTAGTTG ACCTTGGGAA

GTATTTGAAT GAAAACTGGA ATGGGGAGGT GCTCAGCTTC CTTGTGACAT

AAGATTTTAA TACAGATCAC TTGTTTGTGG TGAGGGGTTC TTCATTGAAG

TCTGTATGTA TTTGCAAAAT AACTATTTTT GAGAAGTATT TATTACAGTA

ATCCATAAGT AATTCTTTTA ATCACTTTAA AGTACACTGA ATGCTAATTT

CTGAAATAAA AGTTTCAGCT AAGTG

TABLE 2B

Open Reading Frame Sequence (346-aa) of Clone 42 (SEQ ID NO:24):

Codes (<u>Helix</u>, *Strand*, no prediction)

ML<u>AARLV</u>CLRTLPSRVFQPT*FITKASPL<u>V</u>KNSITKNQWLV*TPSREYATKT*RIRT*H

RGKTGQ<u>ELKEAAALEP</u>S*MEKIFKIDQ*MGR*WF<u>V</u>*AGGA<u>A</u>VGLGA*LCYY*GLGMSNE<u>IGA</u>

<u>IEKAV</u>IWPQYVKDRIHST*YMYLAGS*I*GLTALSALAV*ARTP*ALMNFM*MTG*SWVTIG*

*ATFAAM*IGAG*MLVH*SISYEQSPGPK<u>HLAWMLH</u>SGVMGA*VVAPL*TILGGP<u>LLLRAA</u>

<u>WY*T*A</u>G*IV*GGLS*TVAM*CAPSE<u>KFL</u>NMGAPLGV*GLGLVFA*SSLGSMFLPPTSVAGA*T*

*LYSVA*<u>MY</u>GGL*VLF*<u>S</u>M*FLLY*DT<u>QKVI</u>KRAEITP*M*YGAQKYDPINS*MLTIY*MD<u>TLNI</u>

<u>FMRVATMLA</u>TGSNRKK
//

TABLE 3A mouse Brown Adipose Tissue Reverse (NT-GHA) 62
cDNA (EST); 735 BP. (in bold)
mouse Brown Adipose Tissue Clone 58 cDNA
 (full-length); 1379 BP (SEQ ID NO:25).
Start Codon: 151 (underlined)
Stop Codon: 411 (underlined)
Open Reading Frame: 86-aa

GACTTCCGGC AGACGGTCGG AGCATTTACG GCCGTGGTGC CGCAAAGGCC

TGGAGTGAGG CGGTCTGAGC AAGCTGTCGT CTGGACCCCA GACCTGCTGG

TGGTGAAGTA TATCATGTAT AAAAGTGGAT CAATTCCATG TTAAGTGAAA

<u>ATG</u>GCCAATT CGTTACGAGG AGAAGTACTG ACTCTTTATA AAAATCTGCT

GTATCTTGGA CGGGACTATC CAAAAGGAGC AGACTATTTT AAAAGGCGTT

TGAAGAACGT TTTCCTTAAA ACAAGGATG TGGAGGACCC AGAGAAGATC

AAAGAACTTA TCGCACGAGG AGAATTTGTA ATGAAGGAGC TAGAGGCCTT

GTACTTCCTT AGGAAATACA GAGCTATGAA GCAACGTTAC TATTCAGATA

CCAAAGTC<u>TG</u> <u>A</u>CCAATCATT GCACCAGTCG AGCTGACAAC CAGTGCTGGC

TGTTTGCCTG TACCAACTAT TAAAAAATAA TTCAGTTTAA AAGGGTGAGA

TACATGGTTT TTAAAAAAAT GAGTTGCCCT ACTGTACTGA AATAGGTTTC

AACCTTATTG ATACTGAGAG CTTTGCCCAT AATCCTTTTA TTACTGAAAT

AGTAACTTTA GTACCTTTCA TGATAATATA ATTTTGAAAG AAAATACACT

TAATTTTTAA ACATGTTATA GCCAATTTTC TTAAGTCTAT TTCTTCATTT

ACTGATGAGA TTGTCACTAT CGAATGGTGT CTGACAGGCT TGCCCTTTAG

CTTCTAGAGT GTCTTTGTCC TTGTTTTTTG TTGTTTTGTT AGCCCATCTA

GTATACTAAA GTGCATATTC AAGGCTCTCT ACAGACACCT CAAAATGATT

TAAATGCAGT TATCAAAATA AGACATGTGA AGGTGACCTC TATCTTGAGA

AGCTCAGTGG GTGACTAGCA TTGTGTAGCT ATTATTCCCA TTATTCTTTG

TGCTGCTGGC CTGCCTTAAG TTCTGAACCA CTTCAAGTAG CTTTCATGAG

GAGTTGTAAT GTTCCTCTAT TTCTGCCATT AAAGCTGGTA TATTTTCTGT

CGACCTGTAA CCGAGTCCAT GTGGCAGTGG ACCTAACCCA GGCAGGACTG

TAAGTTTAAG CAAAAATGTT TATGTAATGT TTTTAGCAAC GTTATAAATA

ACATTTCTAA CTTAAAAGCT GCAAATAGTG TTGCTTATAG GATTCTGTAT

TABLE 3A-continued

CAGGCTGGAG AGATGGCTCA GTGGTTAAGA GCACTGACTG CTCTTCCAGA

GGTCCTGAAT TTAATTCCCA GCAACCATAT GGTGGCTTAC AACCATCTGT

AATGGGATCT GATGTCCACT TCTGGTGTGT CTGAACACAG ACAGTGTACT

CATAGAATAA ATAAATAAAC GAATAAATC //

TABLE 3B mouse Brown Adipose Tissue Clone 65 cDNA
full-length); 2436 BP (SEQ ID NO:26).
    Start Codon: 804 (underlined)
    Stop Codon: 1064 (underlined)
    Open Reading Frame: 86-aa

GAGACGGTCG GAGCATTTAC GGCCGTGGTG CCGCAAAGCG CTGGAGTGAG

GCGGTCTGAG CAAGCTGTCG TCTGGACCCC AGACCTGCTG GTGGTGAACT

AAAGCACCGA GTCAAAAGCA TGGTCAGCAG CATGGATGCT GTCTGCTCTG

CCTCCCGTGG AACCTTTCCA AGTGCTCCCT TGCCCGCTG CCTCTTACTC

TGCATTCTCC TTAAGGACCA ACCTTCTTGA TCTTGATCGA ACAACCCAAT

TTATCTTAGT TTTAAAATTT CCTCCAAGAA TACTCTTCTA GATTTGGGCT

CTTAGTTTCT TCCAAATAAT CAAGCCAAGC CTTGAGAGCA GGGCAGACAG

CTTTACTTTT GGTAAGGAAA GCAGGCTTAG AAAAGTGGTG TTACCCAGTG

CCTCAATAAA ACAGCTCAGT ACAAATAACC ATTTGGGGGG ATAAGAAGTC

TTAATGGCAA AGCACTTGCA CAAACAAGAG GGTCCTGTAG ACCTGCAAGT

TTGTAATCCC AGTGTACATA CAGGGGGGTG AGAGGTAGGA GAATCCCTAA

ATGAAGGAAG GGCCAGCTGT TTGCAGCAAC AACTAAGACC CGTGGAAAGG

ACTGACAGCT GAGGTCATCA GCTCCAAATG CACACTGGCA AGTACAAGTC

TGTACACAAG AATGAAAAGC CAGCTCACCA GCTCCATGGG AAGATCTCTG

GTTCTTTAAG ATTTACAATG CAGTTATTTG CAAAAAAAAG AAAATCTTCC

TTTTCTTTAG GTATATCATG TATAAAAGTG GATCAATTCC ATGTTAAGTG

AAA<u>AT</u>GGCCA ATTCGTTACG AGGAGAAGTA CTGACTCTTT ATAAAAATCT

GCTGTATCTT GGACGGGACT ATCCAAAAGG AGCAGACTAT TTTAAAAGGC

GTTTGAAGAA CGTTTTCCTT AAAAACAAGG ATGTGGAGGA CCCAGAGAAG

ATCAAAGAAC TTATCGCACG AGGAGAATTT GTAATGAAGG AGCTAGAGGC

CTTGTACTTC CTTAGGAAAT ACAGAGCTAT GAAGCAACGT TACTATTCAG

ATACCAAAGT C<u>TGA</u>CCAATC ATTGCACCAG TCGAGCTGAC AACCAGTGCT

GGCTGTTTGC CTGTACCAAC TATTAAAAAA TAATTCAGTT TAAAAGGGTG

AGATACATGG TTTTTAAAAA AATGAGTTGC CCTACTGTAC TGAAATAGGT

TTCAACCTTA TTGATACTGA GAGCTTTGCC CATAATCCTT TTATTACTGA

AATAGTAACT TTAGTACCTT TCATGATAAT ATAATTTTGA AGAAAATAC

ACTTAATTTT TAAACATGTT ATAGCCAATT TTCTTAAGTC TATTTCTTCA

TTTACTGATG AGATTGTCAC TATCGAATGG TGTCTGACAG GCTTGCCCTT

TAGCTTCTAG AGTGTCTTTG TCCTTGTTTT TTGTTGTTTT GTTAGCCCAT

CTAGTATACT AAAGTGCATA TTCAAGGCTC TCTACAGACA CCTCAAAATG

TABLE 3B-continued

```
ATTTAAATGC AGTTATCAAA ATAAGACATG TGAAGGTGAC CTCTATCTTG

AGAAGCTCAG TGGGTGACTA GCATTGTGTA GCTATTATTC CCATTATTCT

TTGTGCTGCT GGCCTGCCTT AAGTTCTGAA CCACTTCAAG TAGCTTTCAT

GAGGAGTTGT AATGTTCCTC TATTTCTGCC ATTAAAGCTG GTATATTTTC

TGTCGACCTG TAACCGAGTC CATGTGGCAG TGGACCTAAC CCAGGCAGGA

CTGTAAGTTT AAGCAAAAAT GTTTATGTAA TGTTTTTAGC AACGTTATAA

ATAACATTTC TAACTTAAAA GCTGCAAATA GTGTTGCTTA TAGGATTCTG

TATCAGGCTG GAGAGATGGC TCAGTGGTTA AGAGCACTGA CTGCTCTTCC

AGAGGTCCTG AATTTAATTC CCAGCAACCA TATGGTGGCT ACAACCATC

TGTAATGGGA TCTGATGTCC ACTTCTGGTG TGTCTGAACA CAGACAGTGT

ACTCATAGAA TAAATAAATA AACGAATAAA TCTTAAAGTC TTAAAGGAGT

CTTTATCAAC TACCAAGCAG ACATTTCCAC CAAGAAATAC CTATAGCCAG

GATGGGATG AGGCTCAGTG TTAAGTACTT GCCTAAGGAA CACGTGAGGC

TCCAAAATTG AGCCTTAACC ACAATTAAAA CTACATAATT ACACACTTCA

TAGTCACCAT AACTATTTTT ATTACATTAC AATGATTAGG AGCAGTACGG

TTCATGACAA AAATATTACA AATTTCAGAT CACTTCACAG CACGTACTCC

TATAAACATT TAAAAGTTAA TTTTAATTAA GAGTGGTCAC TTTTAAATTT

AATGTTTGAT ATGACCAACA TTCCCTAGGT CAGCGCAACC AAAGGATGGA

AAACAACTGG ATCACACTGC ATATGTCCCA TAACAA//
```

TABLE 3C

```
mouse Brown Adipose Tissue Clone 66 cDNA
    (full-length); 1612 BP (SEQ ID NO:27).
    Start Codon: 385 (underlined)
    Stop Codon: 645 (underlined)
    Open Reading Frame: 86-aa

GGCCGTGGTG CCGCAAAGCG CTGGAGTGAG GCGGTCTGAG CAAGCTGTCG

TCTGGACCCC AGACCTGCTG GTGGTGAACT AAAGCACCGA GTCAAAAGCA

TGGTCAGCAG CATGGATGCT GTCTGCTCTG CCTCCCGTGG AACCTTTCCA

AGTGCTCCCT TTGCCCGCTG CCTCTTACTC TGCATTCTCC TTAAGGACCA

ACCTTCTTGA TCTTGATCGA ACAACCCAAT TTATCTTAGT TTTAAAATTT

CCTCCAAGAA TACTCTTCTA GATTTGGACT CTTAGTTTCT TCCAAATAAT

CAAGCCAAGC CTTGAGAGCA GGGCAGACAG CTTTACTTTT GGTATATCAT

GTATAAAAGT GGATCAATTC CATGTTAAGT GAAAATGGCC AATTCGTTAC

GAGGAGAAGT ACTGACTCTT TATAAAAATC TGCTGTATCT TGGACGGGAC

TATCCAAAAG GAGCAGACTA TTTTAAAAGG CGTTTGAAGA ACGTTTTCCT

TAAAAACAAG GATGTGGAGG ACCCAGAGAA GATCAAAGAA CTTATCGCAC

GAGGAGAATT TGTAATGAAG GAGCTAGAGG CCTTGTACTT CCTTAGGAAA

TACAGAGCTA TGAAGCAACG TTACTATTCA GATACCAAAG TCTGACCAAT

CATTGCACCA GTCGAGCTGA CAACCAGTGC TGGCTGTTTG CCTGTACCAA

CTATTAAAAA ATAATTCAGT TTAAAAGGGT GAGATACATG GTTTTTAAAA
```

TABLE 3C-continued

```
AAATGAGTTG CCCTACTGTA CTGAAATAGG TTTCAACCTT ATTGATACTG

AGAGCTTTGC CCATAATCCT TTTATTACTG AAATAGTAAC TTTAGTACCT

TTCATGATAA TATAATTTTG AAAGAAAATA CACTTAATTT TTAAACATGT

TATAGCCAAT TTTCTTAAGT CTATTTCTTC ATTTACTGAT GAGATTGTCA

CTATCGAATG GTGTCTGACA GGCTTGCCCT TTAGCTTCTA GAGTGTCTTT

GTCCTTGTTT TTTGTTGTTT TGTTAGCCCA TCTAGTATAC TAAAGTGCAT

ATTCAAGGCT CTCTACAGAC ACCTCAAAAT GATTTAAATG CAGTTATCAA

AATAAGACAT GTGAAGGTGA CCTCTATCTT GAGAAGCTCA GTGGGTGACT

AGCATTGTGT AGCTATTATT CCCATTATTC TTTGTGCTGC TGGCCTGCCT

TAAGTTCTGA ACCACTTCAA GTAGCTTTCA TGAGGAGTTG TAATGTTCCT

CTATTTCTGC CATTAAAGCT GGTATATTTT CTGTCGACCT GTAACCGAGT

CCATGTGGCA GTGGACCTAA CCCAGGCAGG ACTGTAAGTT TAAGCAAAAA

TGTTTATGTA ATGTTTTTAG CAACGTTATA AATAACATTT CTAACTTAAA

AGCTGCAAAT AGTGTTGCTT ATAGGATTCT GTATCAGGCT GGAGAGATGG

CTCAGTGGTT AAGAGCACTG ACTGCTCTTC CAGAGGTCCT GAATTTAATT

CCCAGCAACC ATATGGTGGC TTACAACCAT CTGTAATGGG ATCTGATGTC

CACTTCTGGT GTGTCTGAAC ACAGACAGTG TACTCATAGA ATAAATAAAT

AAACGAATAA AT//
```

TABLE 3D

Alignment of Clones 66 (SEQ ID NO:27), 58 (SEQ ID NO:25) and 65 (SEQ ID NO:26)

```
C66 ---------- ---------- ---------- ---------- ----------

C58 ---------- ---------- ---------- ---------- ----------

C65 GAGACGGTCG GAGCATTTAC GGCCGTGGTG CCGCAAAGCG CTGGAGTGAG    50

C66 ---------- ---------- ---------- ---------- ----------

C58 ---------- ---------- ---------- ---------- ----------

C65 GCGGTCTGAG CAAGCTGTCG TCTGGACCCC AGACCTGCTG GTGGTGAACT   100

C66 ---------- ---------- ---------- ---------- ----------

C58 ---------- ---------- ---------- ---------- ----------

C65 AAAGCACCGA GTCAAAAGCA TGGTCAGCAG CATGGATGCT GTCTGCTCTG   150

C66 ---------- ---------- ---------- ---------- ----------

C58 ---------- ---------- ---------- ---------- ----------

C65 CCTCCCGTGG AACCTTTCCA AGTGCTCCCT TTGCCCGCTG CCTCTTACTC   200

C66 ---------- ---------- ---------- ---------- ----------

C58 ---------- ---------- ---------- ---------- ----------

C65 TGCATTCTCC TTAAGGACCA ACCTTCTTGA TCTTGATCGA ACAACCCAAT   250

C66 ---------- ---------- ---------- ---------- ----------

C58 ---------- ---------- ---------- ---------- ----------
```

TABLE 3D-continued

```
C65  TTATCTTAGT TTTAAAATTT CCTCCAAGAA TACTCTTCTA GATTTGGGCT   300

C66  ---------- ---------- ---------- ---------- ----------

C58  ---------- ---------- ---------- ---------- ----------

C65  CTTAGTTTCT TCCAAATAAT CAAGCCAAGC CTTGAGAGCA GGGCAGACAG   350

C66  ---------- ---------- ---------- ---------- ----------

C58  ---------- ---------- ---------- ---------- ----------

C65  CTTTACTTTT GGTAAGGAAA GCAGGCTTAG AAAAGTGGTG TTACCCAGTG   400

C66  ---------- ---------- ---------- ---------- ----------

C58  ---------- ---------- ---------- ---------- ----------

C65  CCTCAATAAA ACAGCTCAGT ACAAATAACC ATTTGGGGGG ATAAGAAGTC   450

C66  -----GGCCG TGGTGCCGCA -AAGCGCTGG AGTGAGGCGG TCTGAGCAAG    44

C58  ---------- ---------- ---------- ---------- ----------

C65  TTAATGGCAA AGCACTTGCA CAAACAAGAG GGTCCTGTAG ACC-TGCAAG   499

C66  -CTGTCGT-C TGGACCCCAG ACCTGCTGGT G-G-TGAACT AAAGCACCGA    90

C58  ---------- ---------- ---------- ---------- ----------

C65  TTTGTAATCC CAGTGTACAT ACAGGGGGT GAGAGGTAGG AGAATCCCTA    549

C66  GTCAAAAGCA TGGTCAGCAG CATGGATGCT GTCTGCTCTG CCTCCCGTGG   140

C58  ---------- ---------- ---------- ---------- ----------

C65  AATGAAGGAA GGGCCAGCTG TTTGCA-GC- AACAACTAAG --ACCCGTGG   595

C66  AACCTTTCCA AGTGCTCCCT TTGCCCGCTG CCTCTTACTC TGCATTCTCC   190

C58  ---------- ---------- ---------- ---------- ----------

C65  AA-AGGACTG ACAGCTGAGG TCATCAGCT- CC----A-AA TGCACACT-G   637

C66  TTAAGGACCA ACCTTCTTGA TCTTGATCGA ACAACCCAAT TTATC-TTAG   239

C58  ---------- ---------- ---------- -------GA CTTCCGGCAG    12

C65  GCAAGTA-CA AGTCTGTACA -CAAGAATGA A-AAGCCAGC TCACCAGC--   682

C66  TT--TT--AA AATTTCCTCC AAGAATACTC TTCTAGATTT GGACTCTTAG   285

C58  ACGGTCGGAG CATTTACGGC -CGTGGTGCC GCAAAGGCCT GGAGT-GAGG    60

C65  TCCATGGGAA GATCT----- -C-TGGT-TC TTTAAGATTT ACAAT-GCAG   723

C66  TTTCTTCCAA ATAATCAAGC CAAGCCTTGA GAGCAGGGCA GA-CAGCTTT   334

C58  CG--GTC--- -TGAGCAAG- CTGTCGTCTG GACC---CCA GACCTGCTGG   100

C65  TT--ATT--- -T--GCAAA- AAAAAG--AA AATC---TT- --CCT-TT--   753

C66  ACTTTTGGTA TATCATGTAT AAAAGTGGAT CAATTCCATG TTAAGTGAAA   384

C58  TGGTGAAGTA TATCATGTAT AAAAGTGGAT CAATTCCATG TTAAGTGAAA   150

C65  TCTTTAGGTA TATCATGTAT AAAAGTGGAT CAATTCCATG TTAAGTGAAA   803

C66  ATGGCCAATT CGTTACGAGG AGAAGTACTG ACTCTTTATA AAAATCTGCT   434

C58  ATGGCCAATT CGTTACGAGG AGAAGTACTG ACTCTTTATA AAAATCTGCT   200

C65  ATGGCCAATT CGTTACGAGG AGAAGTACTG ACTCTTTATA AAAATCTGCT   853

C66  GTATCTTGGA CGGGACTATC CAAAAGGAGC AGACTATTTT AAAAGGCGTT   484

C58  GTATCTTGGA CGGGACTATC CAAAAGGAGC AGACTATTTT AAAAGGCGTT   250

C65  GTATCTTGGA CGGGACTATC CAAAAGGAGC AGACTATTTT AAAAGGCGTT   903
```

TABLE 3D-continued

```
C66  TGAAGAACGT TTTCCTTAAA AACAAGGATG TGGAGGACCC AGAGAAGATC    534
C58  TGAAGAACGT TTTCCTTAAA AACAAGGATG TGGAGGACCC AGAGAAGATC    300
C65  TGAAGAACGT TTTCCTTAAA AACAAGGATG TGGAGGACCC AGAGAAGATC    953

C66  AAAGAACTTA TCGCACGAGG AGAATTTGTA ATGAAGGAGC TAGAGGCCTT    584
C58  AAAGAACTTA TCGCACGAGG AGAATTTGTA ATGAAGGAGC TAGAGGCCTT    350
C65  AAAGAACTTA TCGCACGAGG AGAATTTGTA ATGAAGGAGC TAGAGGCCTT   1003

C66  GTACTTCCTT AGGAAATACA GAGCTATGAA GCAACGTTAC TATTCAGATA    634
C58  GTACTTCCTT AGGAAATACA GAGCTATGAA GCAACGTTAC TATTCAGATA    400
C65  GTACTTCCTT AGGAAATACA GAGCTATGAA GCAACGTTAC TATTCAGATA   1053

C66  CCAAAGTCTG ACCAATCATT GCACCAGTCG AGCTGACAAC CAGTGCTGGC    684
C58  CCAAAGTCTG ACCAATCATT GCACCAGTCG AGCTGACAAC CAGTGCTGGC    450
C65  CCAAAGTCTG ACCAATCATT GCACCAGTCG AGCTGACAAC CAGTGCTGGC   1103

C66  TGTTTGCCTG TACCAACTAT TAAAAAATAA TTCAGTTTAA AAGGGTGAGA    734
C58  TGTTTGCCTG TACCAACTAT TAAAAAATAA TTCAGTTTAA AAGGGTGAGA    500
C65  TGTTTGCCTG TACCAACTAT TAAAAAATAA TTCAGTTTAA AAGGGTGAGA   1153

C66  TACATGGTTT TTAAAAAAAT GAGTTGCCCT ACTGTACTGA AATAGGTTTC    784
C58  TACATGGTTT TTAAAAAAAT GAGTTGCCCT ACTGTACTGA AATAGGTTTC    550
C65  TACATGGTTT TTAAAAAAAT GAGTTGCCCT ACTGTACTGA AATAGGTTTC   1203

C66  AACCTTATTG ATACTGAGAG CTTTGCCCAT AATCCTTTTA TTACTGAAAT    834
C58  AACCTTATTG ATACTGAGAG CTTTGCCCAT AATCCTTTTA TTACTGAAAT    600
C65  AACCTTATTG ATACTGAGAG CTTTGCCCAT AATCCTTTTA TTACTGAAAT   1253

C66  AGTAACTTTA_GTACCTTTCA TGATAATATA ATTTTGAAAG AAAATACACT    884
C58  AGTAACTTTA_GTACCTTTCA TGATAATATA ATTTTGAAAG AAAATACACT    650
C65  AGTAACTTTA_GTACCTTTCA TGATAATATA ATTTTGAAAG AAAATACACT   1303

C66  TAATTTTTAA ACATGTTATA GCCAATTTTC TTAAGTCTAT TTCTTCATTT    934
C58  TAATTTTTAA ACATGTTATA GCCAATTTTC TTAAGTCTAT TTCTTCATTT    700
C65  TAATTTTTAA ACATGTTATA GCCAATTTTC TTAAGTCTAT TTCTTCATTT   1353

C66  ACTGATGAGA TTGTCACTAT CGAATGGTGT CTGACAGGCT TGCCCTTTAG    984
C58  ACTGATGAGA TTGTCACTAT CGAATGGTGT CTGACAGGCT TGCCCTTTAG    750
C65  ACTGATGAGA TTGTCACTAT CGAATGGTGT CTGACAGGCT TGCCCTTTAG   1403

C66  CTTCTAGAGT GTCTTTGTCC TTGTTTTTTG TTGTTTTGTT AGCCCATCTA   1034
C58  CTTCTAGAGT GTCTTTGTCC TTGTTTTTTG TTGTTTTGTT AGCCCATCTA    800
C65  CTTCTAGAGT GTCTTTGTCC TTGTTTTTTG TTGTTTTGTT AGCCCATCTA   1453

C66  GTATACTAAA GTGCATATTC AAGGCTCTCT ACAGACACCT CAAAATGATT   1084
C58  GTATACTAAA GTGCATATTC AAGGCTCTCT ACAGACACCT CAAAATGATT    850
C65  GTATACTAAA GTGCATATTC AAGGCTCTCT ACAGACACCT CAAAATGATT   1503

C66  TAAATGCAGT TATCAAAATA AGACATGTGA AGGTGACCTC TATCTTGAGA   1134
C58  TAAATGCAGT TATCAAAATA AGACATGTGA AGGTGACCTC TATCTTGAGA    900
C65  TAAATGCAGT TATCAAAATA AGACATGTGA AGGTGACCTC TATCTTGAGA   1553
```

TABLE 3D-continued

```
C66  AGCTCAGTGG GTGACTAGCA TTGTGTAGCT ATTATTCCCA TTATTCTTTG   1184
C58  AGCTCAGTGG GTGACTAGCA TTGTGTAGCT ATTATTCCCA TTATTCTTTG    950
C65  AGCTCAGTGG GTGACTAGCA TTGTGTAGCT ATTATTCCCA TTATTCTTTG   1603

C66  TGCTGCTGGC CTGCCTTAAG TTCTGAACCA CTTCAAGTAG CTTTCATGAG   1234
C58  TGCTGCTGGC CTGCCTTAAG TTCTGAACCA CTTCAAGTAG CTTTCATGAG   1000
C65  TGCTGCTGGC CTGCCTTAAG TTCTGAACCA CTTCAAGTAG CTTTCATGAG   1653

C66  GAGTTGTAAT GTTCCTCTAT TTCTGCCATT AAAGCTGGTA TATTTTCTGT   1284
C58  GAGTTGTAAT GTTCCTCTAT TTCTGCCATT AAAGCTGGTA TATTTTCTGT   1050
C65  GAGTTGTAAT GTTCCTCTAT TTCTGCCATT AAAGCTGGTA TATTTTCTGT   1703

C66  CGACCTGTAA CCGAGTCCAT GTGGCAGTGG ACCTAACCCA GGCAGGACTG   1334
C58  CGACCTGTAA CCGAGTCCAT GTGGCAGTGG ACCTAACCCA GGCAGGACTG   1100
C65  CGACCTGTAA CCGAGTCCAT GTGGCAGTGG ACCTAACCCA GGCAGGACTG   1753

C66  TAAGTTTAAG CAAAAATGTT TATGTAATGT TTTTAGCAAC GTTATAAATA   1384
C58  TAAGTTTAAG CAAAAATGTT TATGTAATGT TTTTAGCAAC GTTATAAATA   1150
C65  TAAGTTTAAG CAAAAATGTT TATGTAATGT TTTTAGCAAC GTTATAAATA   1803

C66  ACATTTCTAA CTTAAAAGCT GCAAATAGTG TTGCTTATAG GATTCTGTAT   1434
C58  ACATTTCTAA CTTAAAAGCT GCAAATAGTG TTGCTTATAG GATTCTGTAT   1200
C65  ACATTTCTAA CTTAAAAGCT GCAAATAGTG TTGCTTATAG GATTCTGTAT   1853

C66  CAGGCTGGAG AGATGGCTCA GTGGTTAAGA GCACTGACTG CTCTTCCAGA   1484
C58  CAGGCTGGAG AGATGGCTCA GTGGTTAAGA GCACTGACTG CTCTTCCAGA   1250
C65  CAGGCTGGAG AGATGGCTCA GTGGTTAAGA GCACTGACTG CTCTTCCAGA   1903

C66  GGTCCTGAAT TTAATTCCCA GCAACCATAT GGTGGCTTAC AACCATCTGT   1534
C58  GGTCCTGAAT TTAATTCCCA GCAACCATAT GGTGGCTTAC AACCATCTGT   1300
C65  GGTCCTGAAT TTAATTCCCA GCAACCATAT GGTGGCTTAC AACCATCTGT   1953

C66  AATGGGATCT GATGTCCACT TCTGGTGTGT CTGAACACAG ACAGTGTACT   1584
C58  AATGGGATCT GATGTCCACT TCTGGTGTGT CTGAACACAG ACAGTGTACT   1350
C65  AATGGGATCT GATGTCCACT TCTGGTGTGT CTGAACACAG ACAGTGTACT   2003

C66  CATAGAATAA ATAAATAAAC GAATAAAT-- ---------- ----------   1612
C58  CATAGAATAA ATAAATAAAC GAATAAATC- ---------- ----------   1379
C65  CATAGAATAA ATAAATAAAC GAATAAATCT TAAAGTCTTA AAGGAGTCTT   2053

C66  ---------- ---------- ---------- ---------- ----------   1612
C58  ---------- ---------- ---------- ---------- ----------   1379
C65  TATCAACTAC CAAGCAGACA TTTCCACCAA GAAATACCTA TAGCCAGGAT   2103

C66  ---------- ---------- ---------- ---------- ----------   1612
C58  ---------- ---------- ---------- ---------- ----------   1379
C65  GGGGATGAGG CTCAGTGTTA AGTACTTGCC TAAGGAACAC GTGAGGCTCC   2153

C66  ---------- ---------- ---------- ---------- ----------   1612
C58  ---------- ---------- ---------- ---------- ----------   1379
C65  AAAATTGAGC CTTAACCACA ATTAAAACTA CATAATTACA CACTTCATAG   2203

C66  ---------- ---------- ---------- ---------- ----------   1612
```

TABLE 3D-continued

| | | | | | | |
|---|---|---|---|---|---|---|
| C58 | ---------- | ---------- | ---------- | ---------- | ---------- | 1379 |
| C65 | TCACCATAAC | TATTTTTATT | ACATTACAAT | GATTAGGAGC | AGTACGGTTC | 2253 |
| C66 | ---------- | ---------- | ---------- | ---------- | ---------- | 1612 |
| C58 | ---------- | ---------- | ---------- | ---------- | ---------- | 1379 |
| C65 | ATGACAAAAA | TATTACAAAT | TTCAGATCAC | TTCACAGCAC | GTACTCCTAT | 2303 |
| C66 | ---------- | ---------- | ---------- | ---------- | ---------- | 1612 |
| C58 | ---------- | ---------- | ---------- | ---------- | ---------- | 1379 |
| C65 | AAACATTTAA | AAGTTAATTT | TAATTAAGAG | TGGTCACTTT | TAAATTTAAT | 2353 |
| C66 | ---------- | ---------- | ---------- | ---------- | ---------- | 1612 |
| C58 | ---------- | ---------- | ---------- | ---------- | ---------- | 1379 |
| C65 | GTTTGATATG | ACCAACATTC | CCTAGGTCAG | CGCAACCAAA | GGATGGAAAA | 2403 |
| C66 | ---------- | ---------- | ---------- | --- | | 1612 |
| C58 | ---------- | ---------- | ---------- | --- | | 1379 |
| C65 | CAACTGGATC | ACACTGCATA | TGTCCCATAA | CAA | | 2436 |

Position of probe 62 shown by underlining.

TABLE 3E

Open Reading Frame Sequence (86-aa) for clones 66, 58, 65:

MANSLRGEVLTLYKNLLYLGRDYPKGADYFKRRLKNVFLKNKDVEDPEKIKELIARGEFVMK (SEQ ID NO:28)

ELEALYFLRKYRAMKQRYYSDTKV

TABLE 3F

Polypeptide Sequence Alignments:
Sequence 1 (SEQ ID NO:28): ORF of Clone 58, 65, & 66
Sequence 2 (SEQ ID NO:29): CG6115 gene encoding a 85-aa
polypeptide in Drosophila melanogaster (GI: 7298358)
intermediate marking indicates the identities (letter) and similarities (+)

MANSLRGEVLTLYKNLLYLGRDYP--KGAD

M + LR +V++LYK+L YLGR+YPG

M-SQLRSKVISLYKHLQYLGREYPGLNGPQ

YFKRRLKNVFLKNKDVEDPEKIKELIARGE

F++++ + F+ +KD +DP+KI L+A+G

KFRKQIHDAFMNHKDEQDPKKIVALLAQGR

FVMKELEALYFLRKYRAMKQRY-YSDTKV  (SEQ ID NO:28)

++ KE+EALY L+KYR++KQRY Y+D

YLAKEVEALYSLKKYRSVKQRYSYND  (SEQ ID NO:29)

Table 4. Unknown Estimated Sequence Tags (EST) Identified in Reverse Subtraction Library (NT-GHA)

TABLE 4a mouse Brown Adipose Tissue Reverse (NT-GHA) 2 cDNA (EST); 556 BP.

1st strand (SEQ ID NO: 30):

ACATTTCAAG AGATGGAGAA ACATTTAGGT CCAGTAAATT TCTTGGTAAA

TGCAGCCGGT ATCAACAGAG ACAGTCTTCT AGTAAGAACA AAGACTGAAG

TABLE 4a-continued

```
ACATGATCTC TCAGCTGCAC ACTAACCTCC TGGGCTCCAT GCTGACCTGT

AAAGCTGCCA TGGAGACAAT GATTCAGCAG GGAGGGTCTA TTGTTAATGT

GGGAAGTATT ATTGGTTTGA AAGGCAACGT TGGCCAGTCT GCATACAGTG

CCACCAAAGG AGGACTCGTT GGGTTTTCAC GCTCGCTTGC TAAAGAGGTT

GCACGGAAGA AAAATCAGAG TGAATGTGGT GGCACCAGGA TTTATTCGCA

CGGATATGAC AAGACACTTG AAGAAGAAC ACTTCAAGAA AAACATTCCT

CTTGGGAGGT TTGGAGAAAC TCCTTGAGGT AGCACATGCC GTTGTGTTTC

TTTTAGAGTC ACCATACATC ACAGGCCATG TTCTTACCGT GGATGGAGGA

TTGCAGCTCA CCGTCTAATT AGAGATGATG TTACTGTGAT GCGCTTTGGG

TCAAGT
//
```

2<sup>nd</sup> strand (SEQ ID NO: 31):

```
ACTTGACCCA AAGCGCATCA CAGTAACATC ATCTCTAATT AGACGGTGAG

CTGCAATCCT CCATCCACGG TAAGAACATG GCCTGTGATG TATGGTGACT

CTAAAAGAAA CACAACGGCA TGTGCTACCT CAAGGAGTTT CTCCAAACCT

CCCAAGAGGA ATGTTTTTCT TGAAGTGTTC TTCTTTCAAG TGTCTTGTCA

TATCCGTGCG AATAAATCCT GGTGCCACCA CATTCACTCT GATTTTTCTT

CCGTGCAACC TCTTTAGCAA GCGAGCGTGA AAACCCAACG AGTCCTCCTT

TGGTGGCACT GTATGCAGAC TGGCCAACGT TGCCTTTCAA ACCAATAATA

CTTCCCACAT TAACAATAGA CCCTCCCTGC TGAATCATTG TCTCCATGGC

AGCTTTACAG GTCAGCATGG AGCCCAGGAG GTTAGTGTGC AGCTGAGAGA

TCATGTCTTC AGTCTTTGTT CTTACTAGAA GACTGTCTCT GTTGATACCG

GCTGCATTTA CCAAGAAATT TACTGGACCT AAATGTTTCT CCATCTCTTG

AAATGT
```

TABLE 4B mouse Brown Adipose Tissue Reverse (NT-GHA) 15
cDNA (EST); 681 BP.

1st strand (SEQ ID NO:32):

```
ACCCATTAGC CAAACAGAAC TCCTGAATAT ATCTTGAAAG CCTTTCTTGT

ATTGTTTCTT CATCTGTAGG TTTGAACACA GCAGGAGATT TTATCATGGC

CTCCACCTGA TCCACCTCTA TTTCCCAGTC CCTAGCTAAT CTCTGCAAAG

ATGTTTCATC CACTCCAAAC ACAGTGCGGT AGAATTTCAT GCTTTTCTTC

AGAGTCTCCA AATCACTGTC CAAGAGAAAG GTCAGAGAAG GGATGATATT

CACTAGGTCA GCAGCAAATC CTTCCAGCCA AATCCTCTGC TTCAGAAATT

GCCGCTTCTT TTCAATGACT GAATCTGTGA TATTGGGTAA GGAGACCATA

AAATTGTGTC TCTTGTAGAT AGGGAGGTCA CTTATCAGCT TGTCCATCAG

GACGGGAAG TCATAGTGAC AAACATTTTT GTTAGAGAGC AGGAAGATTG

GTGGCTCAGC AATGCCATTC TCCCTAAAGG TGTTCACACA GTTAAGGCGG
```

TABLE 4B-continued

| | | | | |
|---|---|---|---|---|
| ATGTCCTGCA | GGACCTTTTC | TTTGTCAAAG | GTTTGAGGTT | TGCCATCTGC |
| TTCATTTGTT | ATGTCAGAGT | CCACCTTGGT | TCTCACGAAG | TAGAATTCCT |
| TCTTCATCAT | GCTGATTGCT | TTGGCAATGT | CTATATCATT | TTTCTTGAAG |
| CGTGTGGCCG | AAATAATAAT | GAAGAAATCG T | | // |

2<sup>nd</sup> strand(SEQ ID NO:33):

| | | | | |
|---|---|---|---|---|
| ACGATTTCTT | CATTATTATT | TCGGCCACAC | GCTTCAAGAA | AAATGATATA |
| GACATTGCCA | AAGCAATCAG | CATGATGAAG | AAGGAATTCT | ACTTCGTGAG |
| AACCAAGGTG | GACTCTGACA | TAACAAATGA | AGCAGATGGC | AAACCTCAAA |
| CCTTTGACAA | AGAAAAGGTC | CTGCAGGACA | TCCGCCTTAA | CTGTGTGAAC |
| ACCTTTAGGG | AGAATGGCAT | TGCTGAGCCA | CCAATCTTCC | TGCTCTCTAA |
| CAAAAATGTT | TGTCACTATG | ACTTCCCCGT | CCTGATGGAC | AAGCTGATAA |
| GTGACCTCCC | TATCTACAAG | AGACACAATT | TTATGGTCTC | CTTACCCAAT |
| ATCACAGATT | CAGTCATTGA | AAAGAAGCGG | CAATTTCTGA | AGCAGAGGAT |
| TTGGCTGGAA | GGATTTGCTG | CTGACCTAGT | GAATATCATC | CCTTCTCTGA |
| CCTTTCTCTT | GGACAGTGAT | TTGGAGACTC | TGAAGAAAAG | CATGAAATTC |
| TACCGCACTG | TGTTTGGAGT | GGATGAAACA | TCTTTGCAGA | GATTAGCTAG |
| GGACTGGGAA | ATAGAGGTGG | ATCAGGTGGA | GGCCATGATA | AAATCTCCTG |
| CTGTGTTCAA | ACCTACAGAT | GAAGAAACAA | TACAAGAAAG | GCTTTCAAGA |
| TATATTCAGG | AGTTCTGTTT | GGCTAATGGG T// | | |

TABLE 5

Unknown Full Length cDNA Sequence Identified in
Brown Adipose Tissue Full Length cDNA Library.
mouse Brown Adipose Tissue NG62D'4-2-1-4 cDNA
(Full-Length); 2280 BP (SEQ ID NO:34).
Start Codon: 163
Stop Codon: 2241
Open Reading Frame: 692-aa

| | | | | |
|---|---|---|---|---|
| GACAGTGGGA | GAGGCAAAAT | GGCCGCGGGA | GTGGCGGCGA | GTGGATCGCT |
| TCCCACAGCG | GGCATTATAA | TTGATTAGGT | TTCTGATATC | AAGATATCTT |
| CCTAAGAAGT | AAATTAACAA | GCCTCACGTT | TCTGTGCAAA | CACTGAGGAG |
| CCAGTTGGCA | CCATGAAGGT | CTTCTGTGGC | CGTGCCAATC | CTACCACGGG |
| ATCCCTGGAG | TGGCTGGAGG | AGGATGAACA | CTATGATTAC | CACCAGGAGA |
| TTGCCAGGTC | ATCCTATGCC | GACATGCTAC | ATGACAAAGA | CAGAAATATA |
| AAATACTACC | AGGGTATCCG | GGCAGCTGTG | AGCAGGGTGA | AAGACAGAGG |
| ACAGAAGGCC | TTGGTTCTTG | ACATTGGCAC | TGGCACAGGC | CTCTTGTCAA |
| TGATGGCAGT | TACTGCAGGG | GCTGACTTCT | GCTATGCTAT | CGAGGTTTTT |
| AAGCCTATGG | CTGAGGCTGC | TGTGAAGATT | GTGGAGAGGA | ATGGCTTCAG |
| TGATAAGATT | AAAGTCATTA | ACAAGCACTC | CACTGAGGTG | ACAGTCGGAC |
| CAGATGGTGA | CTTGCCGTGT | CGTGCTAACA | TTCTGATCAC | GGAGCTGTTT |
| GACACAGAGC | TGATTGGGGA | GGGAGCGCTG | CCCTCTTATG | AGCATGCACA |
| CAAGCATCTT | GTCCAGGAAG | ACTGCGAGGC | AGTGCCACAC | AGGGCAACTG |

TABLE 5-continued

```
TCTATGCCCA  GCTGGTGGAG  TCCCGAAGGA  TGTGGTCCTG  GAACAAGCTG

TTTCCCGTCC  GTGTCCGGAC  GAGTCTAGGC  GAGCAGGTCA  TCGTCCCCCC

CTCAGAATTG  GAGAGGTGTC  CTGGTGCGCC  TTCAGTCTGT  GACATTCAGC

TGAACCAGGT  GTCGCCTGCT  GACTTCACTG  TCCTCAGTGA  TGTGCTGCCA

ATGTTCAGCG  TGGACTTCAG  CAAGCAAGTC  AGCAGCTCGG  CAGCGTGCCA

TAGCAGGCAG  TTTGTACCTT  TGGCGTCTGG  CCAAGCACAG  GTGGTTCTGT

CCTGGTGGGA  CATTGAAATG  GACCCTGAGG  GCAAGATCAA  GTGCACCATG

GCACCCTTTT  GGGCACAGAC  AGATCCGCAG  GAGCTTCAGT  GGCGGGACCA

CTGGATGCAG  TGTGTGTACT  TCCTGCCGCA  GGAGGAGCCT  GTTGTGCAGG

GCTCACCCCG  GTGCCTGGTA  GCCCACCATG  ATGACTACTG  TGTGTGGTAC

AGCCTTCAGA  GAACCAGCCC  TGATGAGAAC  GACAGCGCCT  ACCAAGTGCG

ACCTGTGTGT  GACTGTCAGG  CTCACTTGCT  CTGGAACCGG  CCTCGGTTTG

GAGAAATCAA  TGATCAGGAC  AGAACTGATC  ACTATGCCCA  GGCCCTGAGG

ACTGTGCTGC  TGCCAGGTAG  CGTCTGCCTT  TGTGTGAGTG  ATGGCAGTCT

CCTCTCCATG  CTGGCCCATC  ACCTCGGAGC  GGAGCAGGTG  TTTACAGTTG

AGAGTTCAGT  AGCTTCCTAT  AGACTGATGA  AAAGGATCTT  CAAGGTTAAC

CACTTGGAAG  ATAAAATCAG  TGTCATCAAT  AAACGGCCTG  AGTTGCTGAC

AGCTGCAGAC  CTGGAGGGCA  AGAAGGTCTC  CCTCCTCCTG  GGTGAACCCT

TTTTCACCAC  CAGCCTGCTG  CCATGGCACA  ACCTGTACTT  CTGGTATGTC

CGTACCTCTG  TGGACCAGCA  CCTAGCACCT  GGAGCTGTGG  TGATGCCTCA

GGCTGCCTCA  CTGCATGCCG  TGATTGTGGA  GTTCAGGGAC  CTGTGGCGGA

TCCGGAGTCC  TTGCGGTGAC  TGCGAAGGTT  TTGATGTGCA  CATCATGGAT

GATATGATCA  AGCACTCCCT  GGATTTCCGA  GAGAGCAGAG  AGGCAGAGCC

ACACCCACTG  TGGGAATACC  CCTGCAGAAG  CCTCTCCAAG  CCTCAAGAGA

TCCTGACTTT  TGATTTCCAG  CAGCCCATCC  CCCAACAGCC  TATGCAATCC

AAGGGCACAA  TGGAGCTGAC  AAGACCCGGG  AAGAGCCATG  GGGCTGTCCT

GTGGATGGAG  TATCAGCTCA  CTCCAGACAG  CACGATCAGC  ACTGGCCTCA

TAAACCCTGC  AGAAGACAAG  GGGGACTGCT  GCTGGAACCC  CCACTGCAAG

CAAGCTGTGT  ACTTCCTCAG  CACCACGCTG  GATCTCAGAG  TGCCTCTGAA

TGGCCCTCGG  TCAGTCAGCT  ATGTTGTGGA  GTTTCACCCC  CTCACTGGAG

ACATCACCAT  GGAGTTTAGG  CTTGCAGACA  CCTTGAGCTG  ATCTCTTATT

GAGAAATAAA  ATGGCCAGCA  GGCTGCAGAC
```

//

ORF Sequence (SEQ ID NO:35):

MKVFCGRANPTTGSLEWLEEDEHYDYHQEIARSSYADMLHDKDRNIKYYQGIRAAVSRVK

DRGQKALVLDIGTGTGLLSMMAVTAGADFCYAIEVFKPMAEAAVKIVERNGFSDKIKVIN

KHSTEVTVGPDGDLPCRANILITELFDTELIGEGALPSYEHAHKHLVQEDCEAVPHRATV

YAQLVESRRMWSWNKLFPVRVRTSLGEQVIVPPSELERCPGAPSVCDIQLNQVSPADFTV

LSDVLPMFSVDFSKQVSSSAACHSRQFVPLASGQAQVVLSWWDIEMDPEGKIKCTMAPFW

TABLE 5-continued

AQTDPQELQWRDHWMQCVYFLPQEEPVVQGSPRCLVAHHDDYCVWYSLQRTSPDENDSAY

QVRPVCDCQAHLLWNRPRFGEINDQDRTDHYAQALRTVLLPGSVCLCVSDGSLLSMLAHH

LGAEQVFTVESSVASYRLMKRIFKVNHLEDKISVINKRPELLTAADLEGKKVSLLLGEPF

FTTSLLPWHNLYFWYVRTSVDQHLAPGAVVMPQAASLHAVIVEFRDLWRIRSPCGDCEGF

DVHIMDDMIKHSLDFRESREAEPHPLWEYPCRSLSKPQEILTFDFQQPIPQQPMQSKGTM

ELTRPGKSHGAVLWMEYQLTPDSTISTGLINPAEDKGDCCWNPHCKQAVYFLSTTLDLRV

PLNGPRSVSYVVEFHPLTGDITMEFRLADTLS

---

The invention claimed is:

1. A method of diagnosing abnormal levels of growth hormone (GH) activity in brown adipose tissue, or of predicting a change in the condition of the brown adipose tissue in response to abnormal levels of GH activity therein, which comprises
   (A) obtaining a sample of brown adipose tissue,
   (B) assaying messenger RNA of said sample, or complementary DNA reverse transcribed from said messenger RNA, to determine the level of transcriptional activity of
   a gene encoding:
adipocyte lipid binding protein (NP001433)
   (C) correlating that level of activity with the level of GH activity in brown adipose tissue or the expected change in the condition of the brown adipose tissue as a result of such GH activity.

2. A method of diagnosing abnormal levels of growth hormone (GH) activity in the brown adipose tissue, or of predicting a change in the condition of the brown adipose tissue in response to abnormal levels of GH activity therein, which comprises
   (A) obtaining a sample from said patient, where said sample is expected to contain protein produced by the brown adipose tissue, (B) assaying the protein in said sample to determine the level of expression of
adipocyte lipid binding protein (NP001433)
   (C) correlating that level of expression with the level of GH activity in the brown adipose tissue or the expected change in the condition of the brown adipose tissue as a result of such GH activity.

3. The method of claim 1, which further comprises determining the level of transcriptional activity or level of expression of glucosephosphate isomerase (NP000166).

4. The method of claim 1 which further comprises determining the level of transcriptional activity or level of expression of neuroleukin.

5. The method of claim 1 which further comprises determining the level of transcriptional activity or level of expression of pyruvate kinase (A33983 or S64635).

6. The method of claim 1 which further comprises determining the level of transcriptional activity or level of expression of heme oxygenase (NP002125 or P30519).

7. The method of claim 1 which further comprises determining the level of transcriptional activity or level of expression of ubiquitin/ribosomal fusion protein (NP003324).

8. The method of claim 1 which further comprises determining the level of transcriptional activity or level of expression of α-enolase (NP001419).

9. The method of claim 1 which further comprises determining the level of transcriptional activity or level of expression of proteasome 6 chain (NP002786).

10. The method of claim 1 which further comprises determining the level of transcriptional activity or level of expression of trans-Golgi network protein.

11. The method of claim 1 which further comprises determining the level of transcriptional activity or level of expression of medium chain acyl-CoA dehydrogenase (protein encoded by U07159).

12. The method of claim 1 which further comprises determining the level of transcriptional activity or level of expression of mitochondrial cytochrome c oxidase (BAA07292).

13. The method of claim 1 which further comprises determining the level of transcriptional activity or level of expression of mitochondrial NADH-ubiquonone oxidoreductase (P03905 or CAA24035).

14. The method of claim 1 which further comprises determining the level of transcriptional activity or level of expression of mitochondrial cytochrome b (AAC28269-88).

15. The method of claim 1 in which the change in the condition of the brown adipose tissue is a change in the tissue weight relative to the body weight.

16. The method of claim 2 in which the change in the condition of the brown adipose tissue is a change in the tissue weight relative to the body weight.

* * * * *

SEQUENCE LISTING

<160> NUMBER OF SEQ ID NOS: 35

<210> SEQ ID NO 1
<211> LENGTH: 57
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<223> OTHER INFORMATION: n at position 57 is a, c, g or t

<400> SEQUENCE: 1
aagcagtggt aacaacgcag agtactttt tttttttttt tttttttttt tttttvn       57

<210> SEQ ID NO 2
<211> LENGTH: 30
<212> TYPE: DNA
<213> ORGANISM: Artificial Sequence
<220> FEATURE:
<223> OTHER INFORMATION: SMART III oligonucleotide

<400> SEQUENCE: 2
aagcagtggt aacaacgcag agtacgcggg                                   30

<210> SEQ ID NO 3
<211> LENGTH: 44
<212> TYPE: DNA
<213> ORGANISM: Artificial Sequence
<220> FEATURE:
<223> OTHER INFORMATION: adaptor 1

<400> SEQUENCE: 3
ctaatacgac tcactatagg gctcgagcgg ccgcccgggc aggt                   44

<210> SEQ ID NO 4
<211> LENGTH: 42
<212> TYPE: DNA
<213> ORGANISM: Artificial Sequence
<220> FEATURE:
<223> OTHER INFORMATION: adaptor 2R

<400> SEQUENCE: 4
ctaatacgac tcactatagg gcagcgtggt cgcggccgag gt                     42

<210> SEQ ID NO 5
<211> LENGTH: 22
<212> TYPE: DNA

-continued

<210> SEQ ID NO 5
<211> LENGTH: 22
<212> TYPE: DNA
<213> ORGANISM: Artificial Sequence
<220> FEATURE:
<223> OTHER INFORMATION: nested PCR primer 1

<400> SEQUENCE: 5
tcgagcggcc gcccgggcag gt                                              22

<210> SEQ ID NO 6
<211> LENGTH: 20
<212> TYPE: DNA
<213> ORGANISM: Artificial Sequence
<220> FEATURE:
<223> OTHER INFORMATION: nested PCR primer 2R

<400> SEQUENCE: 6
agcgtggtcg cggccgaggt                                                 20

<210> SEQ ID NO 7
<211> LENGTH: 13
<212> TYPE: DNA
<213> ORGANISM: Artificial Sequence
<220> FEATURE:
<223> OTHER INFORMATION: 5' overhang EcoRI adaptor

<400> SEQUENCE: 7
aattcggcac gag                                                        13

<210> SEQ ID NO 8
<211> LENGTH: 361
<212> TYPE: DNA
<213> ORGANISM: Mus sp.

<400> SEQUENCE: 8
ctctttataa tcgcctccaa gaccttcacc acccaggaga ccatcaccaa tgcagagaca      60
gcaaaggatg gtttctcgaa gcggccaaga tccatctgca gttgcaaagc actttgtcgc     120
cctgtctacg aacacggcca agtgaaagag gtttggaatt gaccctcaaa acatgttcga     180
gttctgggat tgggtaggtg gcctattcgc tgtggtcagc cattggactt tccattgctc     240
tgtatgtagg ttttgaccac ttcgagcagc tgctgtccgg ggctcactgg atggacctgc     300
acttcctcaa gacgcccctg agaagaatgc ccccgtcct gctggctcta ctgggcatct     360
g                                                                    361

<210> SEQ ID NO 9
<211> LENGTH: 550
<212> TYPE: DNA
<213> ORGANISM: Mus sp.

<400> SEQUENCE: 9
acgcggaagc agtggtaaca acgcagagta caccgcaaaa ggtctcttcc gagctgcggt      60
gcccagcggt gcgtccactg gcatctacga ggcctagaac tccgagacaa tgataagacc     120
cgcttcatgg gggaagggtg tctcacaggc tgttgagcac atcaataaaa ctattgcgcc     180
tgctctggtt agcaagaaag tgaatgttgt ggagcaagag aagattgaca agctgatgat     240
cgagatggac ggcacagaga ataaatctaa atttggtgca aatgccatcc tgggagtgtc     300
cctggctgtc tgcaaagctg gtgccgtgga aagggggtgc ccctttaccg ccacattgct     360
gacttggccg gcaaccctga agtcatcctg cctgtcccgg ctttcaatgt gatcaacggt     420
ggttctcatg ctggcaacaa agctggccat gcaaagagtt catgatcctg cctgtggggc     480
atccagctcc gggaagccat gcgcattgga gcagaggttt accacaacct gaagaacgtg     540
atcaaggaga 550

<210> SEQ ID NO 10
<211> LENGTH: 363
<212> TYPE: DNA
<213> ORGANISM: Mus sp.

<400> SEQUENCE: 10

| | | |
|---|---|---|
| acaagtcctt cgtccagaac tacccagtgg tgtccatcga agatcccttt gaccaggacg | 60 |
| actggggcgc ctggcagaag ttcacggcta gtgcgggcat ccaggtggtg ggcgatgacc | 120 |
| tcacagtgac caaccctaag cggattgcca aggctgcgag cgagaagtcc tgcaactgcc | 180 |
| tcttgctcaa agtgaaccag atcggctctg tgaccgaatc cctgcaggcg tgtaagctgg | 240 |
| cccaatccaa tggctggggt gtcatggtgt cccaccgatc tggggaaact gaggacactt | 300 |
| tcatcgcaga cctggtggtg gggctctgca ctgggcagat caagactggt gccccttgcc | 360 |
| gat | 363 |

<210> SEQ ID NO 11
<211> LENGTH: 300
<212> TYPE: DNA
<213> ORGANISM: Mus sp.

<400> SEQUENCE: 11

| | | |
|---|---|---|
| catgcagaga ccatcaagaa tgtccgtgaa gccacagaaa gctttgcatc tgatcccatt | 60 |
| ctctaccgtc ctgttgtggt ggctctggat acaaagggac ctgagatccg gactggactc | 120 |
| atcaagggca gcggcaccgc tgaggtggag ctgaagaagg gagccactct gaagatcacc | 180 |
| ctggacaagc ttcatggag aagtgtgacg agaacatcct gtggctggac tacagacatc | 240 |
| tgcaaggtgt gagtggcagc aagatctacg tggacgatgg ctcatctcac tgcagtgaag | 300 |

<210> SEQ ID NO 12
<211> LENGTH: 299
<212> TYPE: DNA
<213> ORGANISM: Mus sp.

<400> SEQUENCE: 12

| | | |
|---|---|---|
| gcggggactc cagcgcaatc atgtctatta tgtcctataa tggagggggcc gtcatggcat | 60 |
| gaagggaaag aactgtgtgg ccatcgctgc agacagacgt ttcgggatcc aggcccagat | 120 |
| ggtgaccacg gacttccaga agatctttcc catgggtgac aggctctaca taggcctggc | 180 |
| cgcctggcca ctgacgtcca gacagttgcc cagcgtctca agttccgact gaacttgtat | 240 |
| gagctgaaga aggtcgacag atcagcctta cacctactga gactggtggc actctgtat | 299 |

<210> SEQ ID NO 13
<211> LENGTH: 336
<212> TYPE: DNA
<213> ORGANISM: Mus sp.

<400> SEQUENCE: 13

| | | |
|---|---|---|
| tccagttgtc aagacttctt gaaggaaaca ttaagaagga gctatttaag atggcaccac | 60 |
| tgcactttac ttcacatact cagcccttga gaggaatgga ccgcaacaag gacacccagc | 120 |
| cttcgccccc ttatatttcc ccacggagct acaccggaag gcagcactga tcaaggacat | 180 |
| gaagtatttc tttggtgaaa actgggagga gcaggtgaag tgctctgagg ctgcccagaa | 240 |
| gtatgtggat cggattcact atgtaggca aaatgagcca gagctgctgg tggcccatgc | 300 |

```
ttatactcgt tacatggggg actttcaggg ggttag                               336

<210> SEQ ID NO 14
<211> LENGTH: 303
<212> TYPE: DNA
<213> ORGANISM: Mus sp.

<400> SEQUENCE: 14
gggctttctc ttcaacgagg cggccgagcg gcagacgcca acatgcagat cttcgtgaag     60
acctgacggg caagaccatc actcttgagg tcgagcccag tgacaccatc gagaatgtca    120
aggccaagat ccaagacaag gaaggcatcc cacctgacca gcagaggctg atattcgcgg    180
gcaaacagct ggaggatggc cgcaccctgt ccgactacaa catccagaaa gagtccacct    240
tcgacctggt gctgcgtctg cgcggtggca tcattgagcc atccttcgtc agcttgccca    300
gaa                                                                  303

<210> SEQ ID NO 15
<211> LENGTH: 345
<212> TYPE: DNA
<213> ORGANISM: Mus sp.

<400> SEQUENCE: 15
tagcataaaa gggactcgag gtttctgaaa gtaaaatcac tgtttgatgg gattttttaa     60
aaaaatgatc attgaacaag tgtgttcttg catacattca ccccaataag ggcttcctgg    120
aaagggacag gttcatgctt tgtggaagaa aacacatagg agggatttag tatgcaggaa    180
agaggttttc tacaaattga gttttgcttt tattgcccgc agtagataga tatttagaaa    240
ctaactgcat tcttcacact cctccttgct gtttaagatg tgcaggatag gaaatcttcc    300
tatcctgtca tatctggtca tgaactgtag aactaatagt cctga                    345

<210> SEQ ID NO 16
<211> LENGTH: 313
<212> TYPE: DNA
<213> ORGANISM: Mus sp.

<400> SEQUENCE: 16
gcagaagtgg gatggaaagt cgaccacaat aaagagaaaa cgagatggtg acaagctggt     60
ggtggaatgt gttatgaaag gcgtgacttc cacaagagtt tatgaaaggg catgagccaa    120
aggaagaggc ctggatggaa atttgcatca aacactacaa tagtcagtcg gatttattgt    180 ttttttaaa gatatgattt tccactaata agcaagcaat taatttttc tgaagatgca     240 ttttattgga tatggttatg ttgattaaat aaaacctttt tagactcaaa aaaaaaaaa    300 aaaaaaaaa ggt                                                        313

<210> SEQ ID NO 17
<211> LENGTH: 374
<212> TYPE: DNA
<213> ORGANISM: Mus sp.

<400> SEQUENCE: 17
gaattcgatg aaatcaccgc agacgacagg aaggtgaaga gcatcataac cctagatggc     60
ggggccctgg tgcaggtgca gagtgggat ggaaagtcga ccacaataaa gagaaaacga    120
gatggtgaca agctggtggt ggaatgtgtt atgaaaggcg tgacttccac aagagtttat    180
gaaagggcat gagccaaagg aagaggcctg gatggaaatt tgcatcaaac actacaaatag   240 tcagtcggat ttattgtttt tttttaaaga tatgattttc cactaataag caagcaatta    300
```

```
attttttctg aagatgcatt ttattggata tggttatgtt gattaaataa aaccttttta    360
gactcaaaaa aaaa                                                      374
```

<210> SEQ ID NO 18
<211> LENGTH: 542
<212> TYPE: DNA
<213> ORGANISM: Mus sp.

<400> SEQUENCE: 18

```
gaggctgatc atagctcgtg agcacattga aaagtataaa aattaacagg aattactatt     60
gaacgatgca tcaccctcgt gtaactaagc tccaagcact gttgctgctt caggggaaaa    120
gggctttact gtcttcccaa ggaaatgaga tcaaagacga gtttggatct gtgcagcgga    180
ttcccatggc ggaggaacct gtcttcagct ctatggtgac cctttctaga taggtttggc    240
ttttggacaa tgattggtcc ttagccccga attgtgttag tttgctcttt gatcacttaa    300
aatggaaaaa caccctggac ttttaatgtt cattcaagtg acaggaaagg cggcttgtca    360
aggaagaact catgattcta acataaacac tgaaatttg tggtagattg acacgtcag     420 actgtgacat agcagcattt ctgtgctgaa ctgttaattt tataattttg attatatttg    480
ctttgttttg cacaaaagag taaaagttt atattcacat tctcccatta taaaactaaa     540
ac                                                                   542
```

<210> SEQ ID NO 19
<211> LENGTH: 725
<212> TYPE: DNA
<213> ORGANISM: Mus sp.

<400> SEQUENCE: 19

```
gatccgttcg tagttggagt ttgctaggca gaataggagt gatgatgtga ggccatgtgc     60
gattattagt attgttgctc ctatgaagct tcatggagtt tggattatga ttgatgcaat    120
aacaagtgct atgtggctaa ctgaggagta ggcgattagt gatttttaaat ctgtttggcg   180 tacagagatt gagctagtta taattattcc tcataggag agaaggatga aggggtatgc     240
tatatatttt gttagtgggt ctagaataat ggagatgcga attattccgt aactacctaa    300
ttttagaaga atagctgcta gaattattga cccagcaatt ggagcttcaa catgggcttt    360
tggtagtcat aggtgaactc catataatgg tattttaata agaaatgcta ttatgcatgc    420
caaccatagt aagttgttag atcatgaagc gtctaaggtg tgtgttgtga atgataaaat    480
tatgaggttt agggttccta catggttttg gattaagatg agggcaatta gcagtggaat    540
agaaccgatt agggtataaa ataggaaata aatccctgcg tttaggcgtt cagtttggtt    600
cctcatcggg taataataat aagtgttggg attaaggttg cttcaaataa aatataaaat    660
ataattagtt cagttgctga aaaggttatg attaggagaa tttgtaagct gattagtatt    720
gagat                                                                725
```

<210> SEQ ID NO 20
<211> LENGTH: 131
<212> TYPE: DNA
<213> ORGANISM: Mus sp.

<400> SEQUENCE: 20

```
atactcaatt aatctcgagt aatctcgata ataataaaag ataccgcaa acaaagatca      60 cccagctact accatcattc aagtagcaca actatatatt gccgctaccc caatccctcc    120
```
ttccaacata a                                                   131

<210> SEQ ID NO 21
<211> LENGTH: 599
<212> TYPE: DNA
<213> ORGANISM: Mus sp.

<400> SEQUENCE: 21
gagtcatagc cacagcattt ataggctacg tccttccatg aggacaaata tcattctgag      60
gtgccacagt tattacaaac ctcctatcag ccatcccata tattggaaca accctagtcg     120
aatgaatttc aggggcttc tcagtagaca agccaccttt gacccgattc ttcgctttcc     180
acttcatctt accatttatt atcgcggccc tagcaatcgt tcacctcctc ttcctccacg     240
aaacaggatc aaacaaccca acaggattaa actcagatgc agataaaatt ccatttcacc     300
cctactatac aatcaaagat atcctaggta tcctaatcat attcttaatt ctcataaccc     360
tagtattatt tttcccagac atactaggag acccagacaa ctacatacca gctaatccac     420
taaacacccc accccatatt aaacccgaat gatatttcct atttgcatac gccattctac     480
gctcaatccc caataaacta ggaggtgtcc tagccttaat cttatctatc ctaatttag     540
tcctaatacc tttccttcat acctcaaagc aacgaagcct aatattccgc ccaatcaca     599

<210> SEQ ID NO 22
<211> LENGTH: 343
<212> TYPE: DNA
<213> ORGANISM: Mus sp.

<400> SEQUENCE: 22
tccagctata ctatgagcct taggcttatt tctattacag ttggtggtct aaccggaatg      60
tttatccaac tcatcccttg acatcgtgct tcacgataac atactatgta gtagcccatt     120
tccactatgt tctatcaatg ggagcagtgt ttgctatcat agcaggattt gttcactgat     180
tcccattatt ttcaggcttc accctagatg acacatgagc aaaagcccac ttcgccatca     240
tattcgtagg agtaaacata acattcttcc ctcaacattt cctgggcttt caggaatacc     300
acgacgctac tcagactacc cagatgcaaa aaaaaaaaa aaa                       343

<210> SEQ ID NO 23
<211> LENGTH: 2475
<212> TYPE: DNA
<213> ORGANISM: Mus sp.

<400> SEQUENCE: 23
gagagggagg tcgcacactc tgagtttcgg tgacccggaa ggagccccgt ggtagaggtg      60
accggagctg agcatttcag atctgcttag taaaccggtg tatcgcccac catgttggct     120
gcaaggcttg tgtgtctccg gacactacct tccagggttt tccagcccac tttcatcacc     180
aaggcctctc cacttgtgaa gaattccatc acaaagaacc aatggctcgt aacacccagc     240
agggaatatg ctaccaagac aagaattagg actcaccgtg ggaaaactgg acaagaactg     300
aaagaggcag ccaaggaacc atcaatggaa aaatctttta aaatcgatca atgggaaggg     360
tggtttgttg ctggaggagc agctgttggt cttggagcgc tctgctacta tggcttggga     420
atgtctaatg agattggagc tatcgaaaag gctgtaattt ggcctcagta tgtaaaggat     480
agaattcatt ctacttacat gtacttagca ggaagtattg gtttaacagc tttgtctgcc     540
ttggcagtag ccagaacacc tgctctcatg aacttcatga tgcacaggctc ttgggtgaca     600
attggtgcga cctttgcagc catgattgga gctggaatgc ttgtacactc aatatcatat     660

```
gagcagagcc caggcccaaa gcatctggct tggatgctgc attctggtgt gatgggtgca    720
gttgtggctc ctctgacgat cttaggggg cctcttctcc tgagaccgc atggtacacc     780
gctggtattg tgggaggcct ctctactgtg ccatgtgtg cgcctagtga aagtttctg     840
aacatgggag caccctggg agtgggcctg gtcttgtct ttgcgtcttc tctggggtct    900
atgtttcttc ccctacctc tgtggctggt gccactctgt actcagtggc aatgtatggt    960
ggattagttc ttttcagcat gttccttctg tatgatactc agaaagtaat caaacgtgca   1020
gaaataacac ccatgtatgg agctcaaaag tatgatccca tcaattcgat gttgacaatc   1080
tacatggata cattaaatat atttatgcga gttgcaacta tgctagcaac tggaagcaac   1140
agaaagaaat gaagtaaccg cttgtgatgt ctccgctcac tgatgtcttg cttgtttaat   1200
aggagcagat agtcattaca gtttgcatca gcagaattcc ttgaggttta aagatagcc    1260
tgtcaccatg tttaaaatgt gcagtaatgc gacccttcag gcatgccttt tcttttagaa   1320
aataaatgca atagatgtct tccaaatata ttttcatctc ttatgctttc atactttaaa   1380
actgctttga tgaatgtgtg aacaaatata ttttagaaga tttcaagtat tgttttatgt   1440
attggataag taaaatttag caaatttgcg tgtcttcata ttgtggaagc ctgcagaata   1500
tttcagtggc atcatgagtg acaagttttt tgtatagagg tcagagagat aaaaggcacc   1560
tgcagtcagt ttgaatgccc aggacaacac tgattgtggt gagccagtga aagacatcag   1620
agatgtggaa caaggaccca ccaaatgtgg ggttaacaaa gacacggatg tttcttctgt   1680
gctcttaatg tccttgaggt tgactgctca ttgtcaggac agtccagagt gttaaccata   1740
cagagaatct ctgctggaat tatgtctgtg ttttactatg aagtctttag aacaagcagg   1800
ttggtggtgg cgcacacctt tagtcccatc atctgggagg cagaggcaag cagatctcta   1860
aattcaaggc cagccaggtc tacaaagtga gttccaagcc agacaaggac ctgtctctaa   1920
tacaagcaaa caaacaacaa caaacactac cgctatgctc ggtatgatgt actactccaa   1980
agctcaagac tcctttgctg tcagatgtgt ggtgtatatg cagttggaca ggatttaggt   2040
tttggttttt ggttttgttt tattttgata tttttctcag tgtctaattg aaagcatgct   2100
tgctttctca tcacagcttt gacagctgtc agaaaagcct ctttgtggct tatgctaaga   2160
ttaggattgg ttttcttct aaaactgttg gcttcctccg ttccctctca gcttaagcat    2220
gaacaaagca aatttagttg accttgggaa gtatttgaat gaaaactgga atgggaggt    2280
gctcagcttc cttgtgacat aagatttaaa tacagatcac ttgtttgtgg tgaggggttc   2340
ttcattgaag tctgtatgta tttgcaaaat aactattttt gagaagtatt tattacagta   2400
atccataagt aattcttta atcactttaa agtacactga atgctaattt ctgaaataaa    2460
agtttcagct aagtg                                                    2475
```

<210> SEQ ID NO 24
<211> LENGTH: 346
<212> TYPE: PRT
<213> ORGANISM: Mus sp.

<400> SEQUENCE: 24

Met Leu Ala Ala Arg Leu Val Cys Leu Arg Thr Leu Pro Ser Arg Val
1               5                   10                  15

Phe Gln Pro Thr Phe Ile Thr Lys Ala Ser Pro Leu Val Lys Asn Ser
                20                  25                  30

Ile Thr Lys Asn Gln Trp Leu Val Thr Pro Ser Arg Glu Tyr Ala Thr
            35                  40                  45

```
Lys Thr Arg Ile Arg Thr His Arg Gly Lys Thr Gly Gln Glu Leu Lys
 50                  55                  60

Glu Ala Ala Leu Glu Pro Ser Met Glu Lys Ile Phe Lys Ile Asp Gln
 65                  70                  75                  80

Met Gly Arg Trp Phe Val Ala Gly Ala Val Gly Leu Gly Ala
                 85                  90                  95

Leu Cys Tyr Tyr Gly Leu Gly Met Ser Asn Glu Ile Gly Ala Ile Glu
             100                 105                 110

Lys Ala Val Ile Trp Pro Gln Tyr Val Lys Asp Arg Ile His Ser Thr
             115                 120                 125

Tyr Met Tyr Leu Ala Gly Ser Ile Gly Leu Thr Ala Leu Ser Ala Leu
             130                 135                 140

Ala Val Ala Arg Thr Pro Ala Leu Met Asn Phe Met Thr Gly Ser
145                 150                 155                 160

Trp Val Thr Ile Gly Ala Thr Phe Ala Ala Met Ile Gly Ala Gly Met
                165                 170                 175

Leu Val His Ser Ile Ser Tyr Glu Gln Ser Pro Gly Pro Lys His Leu
             180                 185                 190

Ala Trp Met Leu His Ser Gly Val Met Gly Ala Val Ala Pro Leu
         195                 200                 205

Thr Ile Leu Gly Gly Pro Leu Leu Leu Arg Ala Ala Trp Tyr Thr Ala
         210                 215                 220

Gly Ile Val Gly Gly Leu Ser Thr Val Ala Met Cys Ala Pro Ser Glu
225                 230                 235                 240

Lys Phe Leu Asn Met Gly Ala Pro Leu Gly Val Gly Leu Gly Leu Val
                245                 250                 255

Phe Ala Ser Ser Leu Gly Ser Met Phe Leu Pro Pro Thr Ser Val Ala
             260                 265                 270

Gly Ala Thr Leu Tyr Ser Val Ala Met Tyr Gly Gly Leu Val Leu Phe
         275                 280                 285

Ser Met Phe Leu Leu Tyr Asp Thr Gln Lys Val Ile Lys Arg Ala Glu
290                 295                 300

Ile Thr Pro Met Tyr Gly Ala Gln Lys Tyr Asp Pro Ile Asn Ser Met
305                 310                 315                 320

Leu Thr Ile Tyr Met Asp Thr Leu Asn Ile Phe Met Arg Val Ala Thr
             325                 330                 335

Met Leu Ala Thr Gly Ser Asn Arg Lys Lys
             340                 345

<210> SEQ ID NO 25
<211> LENGTH: 1379
<212> TYPE: DNA
<213> ORGANISM: Mus sp.

<400> SEQUENCE: 25
gacttccggc agacggtcgg agcatttacg gccgtggtgc cgcaaaggcc tggagtgagg      60
cggtctgagc aagctgtcgt ctggacccca gacctgctgg tggtgaagta tatcatgtat     120
aaaagtggat caattccatg ttaagtgaaa atggccaatt cgttacgagg agaagtactg     180
actctttata aaaatctgct gtatcttgga cgggactatc aaaaggagc agactatttt      240 aaaaggcgtt tgaagaacgt ttccttaaa aacaaggatg tggaggaccc agagaagatc      300
aaagaactta tcgcacgagg agaatttgta atgaaggagc tagaggcctt gtacttcctt     360
aggaaataca gagctatgaa gcaacgttac tattcagata ccaaagtctg accaatcatt     420
```

-continued

```
gcaccagtcg agctgacaac cagtgctggc tgtttgcctg taccaactat taaaaaataa    480
ttcagtttaa aagggtgaga tacatggttt ttaaaaaaat gagttgccct actgtactga    540
aataggtttc aaccttattg atactgagag ctttgcccat aatccttta ttactgaaat    600 agtaacttta gtacctttca tgataatata attttgaaag aaaatacact taattttaa    660 acatgttata gccaattttc ttaagtctat ttcttcattt actgatgaga ttgtcactat    720
cgaatggtgt ctgacaggct tgcccttag cttctagagt gtctttgtcc ttgttttttg    780
ttgttttgtt agcccatcta gtatactaaa gtgcatattc aaggctctct acagacacct    840
caaaatgatt taaatgcagt tatcaaaata agacatgtga aggtgacctc tatcttgaga    900
agctcagtgg gtgactagca ttgtgtagct attattccca ttattctttg tgctgctggc    960
ctgccttaag ttctgaacca cttcaagtag ctttcatgag gagttgtaat gttcctctat   1020
ttctgccatt aaagctggta tatttctgt cgacctgtaa ccgagtccat gtggcagtgg   1080
acctaaccca ggcaggactg taagtttaag caaaaatgtt tatgtaatgt ttttagcaac   1140
gttataaata acatttctaa cttaaaagct gcaaatagtg ttgcttatag gattctgtat   1200
caggctggag agatggctca gtggttaaga gcactgactg ctcttccaga ggtcctgaat   1260
ttaattccca gcaaccatat ggtggcttac aaccatctgt aatgggatct gatgtccact   1320
tctggtgtgt ctgaacacag acagtgtact catagaataa ataaataaac gaataaaatc   1379
```

<210> SEQ ID NO 26
<211> LENGTH: 2436
<212> TYPE: DNA
<213> ORGANISM: Mus sp.

<400> SEQUENCE: 26

```
gagacggtcg gagcatttac ggccgtggtg ccgcaaagcg ctggagtgag gcggtctgag     60
caagctgtcg tctggacccc agacctgctg gtggtgaact aaagcaccga gtcaaaagca    120
tggtcagcag catggatgct gtctgctctg cctcccgtgg aacctttcca agtgctccct    180
ttgcccgctg cctcttactc tgcattctcc ttaaggacca accttcttga tcttgatcga    240
acaacccaat ttatcttagt tttaaaattt cctccaagaa tactcttcta gatttgggct    300 cttagttct tccaaataat caagccaagc cttgagagca gggcagacag ctttactttt    360
ggtaaggaaa gcaggcttag aaaagtggtg ttacccagtg cctcaataaa acagctcagt    420
acaaataacc atttgggggg ataagaagtc ttaatggcaa agcacttgca caacaagag    480 ggtcctgtag acctgcaagt ttgtaatccc agtgtacata caggggggtg agaggtagga    540
gaatccctaa atgaaggaag ggccagctgt ttgcagcaac aactaagacc cgtgaaaggg    600
actgacagct gaggtcatca gctccaaatg cacactggca agtacaagtc tgtacacaag    660
aatgaaaagc cagctcacca gctccatggg aagatctctg ttctttaag atttacaatg    720 cagttatttg caaaaaaag aaaatcttcc ttttctttag gtatatcatg tataaaagtg    780
gatcaattcc atgttaagtg aaaatggcca attcgttacg aggagaagta ctgactcttt    840
ataaaaatct gctgtatctt ggacgggact atccaaaagg agcagactat tttaaaaggc    900
gtttgaagaa cgttttcctt aaaaacaagg atgtggagga cccagagaag atcaaagaac    960
ttatcgcacg aggagaattt gtaatgaagg agctagaggc cttgtacttc cttaggaaat   1020
acagagctat gaagcaacgt tactattcag ataccaaagt ctgaccaatc attgcaccag   1080
tcgagctgac aaccagtgct ggctgtttgc ctgtaccaac tattaaaaaa taattcagtt   1140
```

-continued

```
taaaagggtg agatacatgg tttttaaaaa aatgagttgc cctactgtac tgaaataggt      1200
ttcaacctta ttgatactga gagctttgcc cataatcctt ttattactga aatagtaact      1260
ttagtacctt tcatgataat ataattttga agaaaatac acttaattt taaacatgtt        1320
atagccaatt ttcttaagtc tatttcttca tttactgatg agattgtcac tatcgaatgg      1380
tgtctgacag gcttgccctt tagcttctag agtgtctttg tccttgtttt ttgttgtttt     1440
gttagcccat ctagtatact aaagtgcata ttcaaggctc tctacagaca cctcaaaatg      1500
atttaaatgc agttatcaaa ataagacatg tgaaggtgac ctctatcttg agaagctcag      1560
tgggtgacta gcattgtgta gctattattc ccattattct ttgtgctgct ggcctgcctt      1620
aagttctgaa ccacttcaag tagctttcat gaggagttgt aatgttcctc tatttctgcc      1680
attaaagctg gtatattttc tgtcgacctg taaccgagtc catgtggcag tggacctaac      1740
ccaggcagga ctgtaagttt aagcaaaaat gtttatgtaa tgtttttagc aacgttataa      1800
ataacatttc taacttaaaa gctgcaaata gtgttgctta taggattctg tatcaggctg      1860
gagagatggc tcagtggtta agagcactga ctgctcttcc agaggtcctg aatttaattc      1920
ccagcaacca tatggtggct acaaccatc tgtaatggga tctgatgtcc acttctggtg       1980
tgtctgaaca cagacagtgt actcatagaa taaataaata aacgaataaa tcttaaagtc      2040
ttaaaggagt ctttatcaac taccaagcag acatttccac caagaaatac ctatagccag      2100
gatgggatg aggctcagtg ttaagtactt gcctaaggaa cacgtgaggc tccaaaattg       2160
agccttaacc acaattaaaa ctacataatt acacacttca tagtcaccat aactattttt      2220
attacattac aatgattagg agcagtacgg ttcatgacaa aaatattaca aatttcagat      2280
cacttcacag cacgtactcc tataaacatt taaaagttaa ttttaattaa gagtggtcac      2340
ttttaaattt aatgtttgat atgaccaaca ttccctaggt cagcgcaacc aaaggatgga      2400
aaacaactgg atcacactgc atatgtccca taacaa                                2436
```

<210> SEQ ID NO 27
<211> LENGTH: 1612
<212> TYPE: DNA
<213> ORGANISM: Mus sp.

<400> SEQUENCE: 27

```
ggccgtggtg ccgcaaagcg ctggagtgag gcggtctgag caagctgtcg tctggacccc       60
agacctgctg gtggtgaact aaagcaccga gtcaaaagca tggtcagcag catggatgct      120
gtctgctctg cctcccgtgg aacctttcca agtgctccct ttgcccgctg cctcttactc      180
tgcattctcc ttaaggacca accttcttga tcttgatcga acaacccaat ttatcttagt      240
tttaaaattt cctccaagaa tactcttcta gatttggact cttagtttct tccaaataat      300
caagccaagc cttgagagca gggcagacag ctttactttt ggtatatcat gtataaaagt      360
ggatcaattc catgttaagt gaaaatggcc aattcgttac gaggagaagt actgactctt      420
tataaaaatc tgctgtatct tggacgggac tatccaaaag gagcagacta ttttaaaagg      480
cgtttgaaga acgttttcct taaaacaag gatgtggagg acccagagaa gatcaaagaa        540
cttatcgcac gaggagaatt tgtaatgaag gagctagagg ccttgtactt ccttaggaaa      600
tacagagcta tgaagcaacg ttactattca gataccaaag tctgaccaat cattgccaca      660
gtcgagctga caaccagtgc tggctgtttg cctgtaccaa ctattaaaaa ataattcagt      720
ttaaaagggt gagatacatg gttttttaaaa aatgagttg ccctactgta ctgaaatagg      780
tttcaacctt attgatactg agagctttgc ccataatcct tttattactg aaatagtaac      840
```

-continued

```
tttagtacct tcatgataa tataattttg aaagaaaata cacttaattt ttaaacatgt      900
tatagccaat tttcttaagt ctatttcttc atttactgat gagattgtca ctatcgaatg      960
gtgtctgaca ggcttgccct ttagcttcta gagtgtcttt gtccttgttt tttgttgttt     1020
tgttagccca tctagtatac taaagtgcat attcaaggct ctctacagac acctcaaaat     1080
gatttaaatg cagttatcaa aataagacat gtgaaggtga cctctatctt gagaagctca     1140
gtgggtgact agcattgtgt agctattatt cccattattc tttgtgctgc tggcctgcct     1200
taagttctga accacttcaa gtagctttca tgaggagttg taatgttcct ctatttctgc     1260
cattaaagct ggtatatttt ctgtcgacct gtaaccgagt ccatgtggca gtggacctaa     1320
cccaggcagg actgtaagtt taagcaaaaa tgtttatgta atgtttttag caacgttata     1380
aataacattt ctaacttaaa agctgcaaat agtgttgctt ataggattct gtatcaggct     1440
ggagagatgg ctcagtggtt aagagcactg actgctcttc cagaggtcct gaatttaatt     1500
cccagcaacc atatggtggc ttacaaccat ctgtaatggg atctgatgtc cacttctggt     1560
gtgtctgaac acagacagtg tactcataga ataaataaat aaacgaataa at            1612
```

<210> SEQ ID NO 28
<211> LENGTH: 86
<212> TYPE: PRT
<213> ORGANISM: Mus sp.

<400> SEQUENCE: 28

```
Met Ala Asn Ser Leu Arg Gly Glu Val Leu Thr Leu Tyr Lys Asn Leu
1               5                   10                  15

Leu Tyr Leu Gly Arg Asp Tyr Pro Lys Gly Ala Asp Tyr Phe Lys Arg
            20                  25                  30

Arg Leu Lys Asn Val Phe Leu Lys Asn Lys Asp Val Glu Asp Pro Glu
        35                  40                  45

Lys Ile Lys Glu Leu Ile Ala Arg Gly Glu Phe Val Met Lys Glu Leu
    50                  55                  60

Glu Ala Leu Tyr Phe Leu Arg Lys Tyr Arg Ala Met Lys Gln Arg Tyr
65                  70                  75                  80

Tyr Ser Asp Thr Lys Val
                85
```

<210> SEQ ID NO 29
<211> LENGTH: 85
<212> TYPE: PRT
<213> ORGANISM: Drosophila melanogaster

<400> SEQUENCE: 29

```
Met Ser Gln Leu Arg Ser Lys Val Ile Ser Leu Tyr Lys His Leu Gln
1               5                   10                  15

Tyr Leu Gly Arg Glu Tyr Pro Gly Leu Asn Gly Pro Gln Lys Phe Arg
            20                  25                  30

Lys Gln Ile His Asp Ala Phe Met Asn His Lys Asp Glu Gln Asp Pro
        35                  40                  45

Lys Lys Ile Val Ala Leu Leu Ala Gln Gly Arg Tyr Leu Ala Lys Glu
    50                  55                  60

Val Glu Ala Leu Tyr Ser Leu Lys Lys Tyr Ser Val Lys Gln Arg
65                  70                  75                  80

Tyr Ser Tyr Asn Asp
                85
```

<210> SEQ ID NO 30
<211> LENGTH: 556
<212> TYPE: DNA
<213> ORGANISM: Mus sp.

<400> SEQUENCE: 30

| | | | | | |
|---|---|---|---|---|---|
| acatttcaag | agatggagaa | acatttaggt | ccagtaaatt | tcttggtaaa | tgcagccggt | 60 |
| atcaacagag | acagtcttct | agtaagaaca | aagactgaag | acatgatctc | tcagctgcac | 120 |
| actaacctcc | tgggctccat | gctgacctgt | aaagctgcca | tggagacaat | gattcagcag | 180 |
| ggagggtcta | ttgttaatgt | gggaagtatt | attggtttga | aggcaacgt | tggccagtct | 240 |
| gcatacagtg | ccaccaaagg | aggactcgtt | gggttttcac | gctcgcttgc | taaagaggtt | 300 |
| gcacggaaga | aaaatcagag | tgaatgtggt | ggcaccagga | tttattcgca | cggatatgac | 360 |
| aagacacttg | aaagaagaac | acttcaagaa | aaacattcct | cttgggaggt | ttggagaaac | 420 |
| tccttgaggt | agcacatgcc | gttgtgtttc | ttttagagtc | accatacatc | acaggccatg | 480 |
| ttcttaccgt | ggatggagga | ttgcagctca | ccgtctaatt | agagatgatg | ttactgtgat | 540 |
| gcgctttggg | tcaagt | | | | | 556 |

<210> SEQ ID NO 31
<211> LENGTH: 556
<212> TYPE: DNA
<213> ORGANISM: Mus sp.

<400> SEQUENCE: 31

| | | | | | |
|---|---|---|---|---|---|
| acttgaccca | aagcgcatca | cagtaacatc | atctctaatt | agacggtgag | ctgcaatcct | 60 |
| ccatccacgg | taagaacatg | gcctgtgatg | tatggtgact | ctaaaagaaa | cacaacggca | 120 |
| tgtgctacct | caaggagttt | ctccaaacct | cccaagagga | atgttttcct | tgaagtgttc | 180 |
| ttctttcaag | tgtcttgtca | tatccgtgcg | aataaatcct | ggtgccacca | cattcactct | 240 |
| gattttcctt | ccgtgcaacc | tctttagcaa | gcgagcgtga | aaacccaacg | agtcctcctt | 300 |
| tggtggcact | gtatgcagac | tggccaacgt | tgcctttcaa | accaataata | cttcccacat | 360 |
| taacaataga | ccctccctgc | tgaatcattg | tctccatggc | agctttacag | gtcagcatgg | 420 |
| agcccaggag | ttagtgtgc | agctgagaga | tcatgtcttc | agtctttgtt | cttactagaa | 480 |
| gactgtctct | gttgataccg | gctgcattta | ccaagaaatt | tactggacct | aaatgtttct | 540 |
| ccatctcttg | aaatgt | | | | | 556 |

<210> SEQ ID NO 32
<211> LENGTH: 681
<212> TYPE: DNA
<213> ORGANISM: Mus sp.

<400> SEQUENCE: 32

| | | | | | |
|---|---|---|---|---|---|
| acccattagc | caaacagaac | tcctgaatat | atcttgaaag | cctttcttgt | attgtttctt | 60 |
| catctgtagg | tttgaacaca | gcaggagatt | ttatcatggc | ctccacctga | tccacctcta | 120 |
| tttcccagtc | cctagctaat | ctctgcaaag | atgtttcatc | cactccaaac | acagtgcggt | 180 |
| agaatttcat | gcttttcttc | agagtctcca | atcactgtc | caagagaaag | gtcagagaag | 240 |
| ggatgatatt | cactaggtca | gcagcaaatc | cttccagcca | atcctctgc | ttcagaaatt | 300 |
| gccgcttctt | ttcaatgact | gaatctgtga | tattgggtaa | ggagaccata | aaattgtgtc | 360 |
| tcttgtagat | agggaggtca | cttatcagct | tgtccatcag | gacggggaag | tcatagtgac | 420 |
| aaacattttt | gttagagagc | aggaagattg | gtggctcagc | aatgccattc | tccctaaagg | 480 |

| | |
|---|---:|
| tgttcacaca gttaaggcgg atgtcctgca ggacctttc tttgtcaaag gtttgaggtt | 540 |
| tgccatctgc ttcatttgtt atgtcagagt ccaccttggt tctcacgaag tagaattcct | 600 |
| tcttcatcat gctgattgct ttggcaatgt ctatatcatt tttcttgaag cgtgtggccg | 660 |
| aaataataat gaagaaatcg t | 681 |

<210> SEQ ID NO 33
<211> LENGTH: 681
<212> TYPE: DNA
<213> ORGANISM: Mus sp.

<400> SEQUENCE: 33

| | |
|---|---:|
| acgatttctt cattattatt tcggccacac gcttcaagaa aaatgatata gacattgcca | 60 |
| aagcaatcag catgatgaag aaggaattct acttcgtgag aaccaaggtg gactctgaca | 120 |
| taacaaatga agcagatggc aaacctcaaa cctttgacaa agaaaaggtc ctgcaggaca | 180 |
| tccgccttaa ctgtgtgaac accttaggg agaatggcat tgctgagcca ccaatcttcc | 240 |
| tgctctctaa caaaaatgtt tgtcactatg acttccccgt cctgatggac aagctgataa | 300 |
| gtgacctccc tatctacaag agacacaatt ttatggtctc cttacccaat atcacagatt | 360 |
| cagtcattga aagaagcgg caatttctga agcagaggat ttggctggaa ggatttgctg | 420 |
| ctgacctagt gaatatcatc ccttctctga cctttctctt ggacagtgat ttggagactc | 480 |
| tgaagaaaag catgaaattc taccgcactg tgtttggagt ggatgaaaca tctttgcaga | 540 |
| gattagctag ggactgggaa atagaggtgg atcaggtgga ggccatgata aaatctcctg | 600 |
| ctgtgttcaa acctacagat gaagaaacaa tacaagaaag gctttcaaga tatattcagg | 660 |
| agttctgttt ggctaatggg t | 681 |

<210> SEQ ID NO 34
<211> LENGTH: 2280
<212> TYPE: DNA
<213> ORGANISM: Mus sp.

<400> SEQUENCE: 34

| | |
|---|---:|
| gacagtggga gaggcaaaat ggccgcggga gtggcggcga gtggatcgct tcccacagcg | 60 |
| ggcattataa ttgattaggt ttctgatatc aagatatctt cctaagaagt aaattaacaa | 120 |
| gcctcacgtt tctgtgcaaa cactgaggag ccagttggca ccatgaaggt cttctgtggc | 180 |
| cgtgccaatc ctaccacggg atccctggag tggctgagg aggatgaaca ctatgattac | 240 |
| caccaggaga ttgccaggtc atcctatgcc gacatgctac atgacaaaga cagaaatata | 300 |
| aaatactacc agggtatccg ggcagctgtg agcagggtga agacagagg acagaaggcc | 360 |
| ttggttcttg acattggcac tggcacaggc ctcttgtcaa tgatggcagt tactgcaggg | 420 |
| gctgacttct gctatgctat cgaggttttt aagcctatgg ctgaggctgc tgtgaagatt | 480 |
| gtggagagga atggcttcag tgataagatt aaagtcatta caagcactc cactgaggtg | 540 |
| acagtcggac cagatggtga cttgccgtgt cgtgctaaca ttctgatcac ggagctgttt | 600 |
| gacacagagc tgattgggga gggagcgctg ccctcttatg agcatgcaca caagcatctt | 660 |
| gtccaggaag actgcgaggc agtgccacac agggcaactg tctatgccca gctggtggag | 720 |
| tcccgaagga tgtggtcctg gaacaagctg tttcccgtcc gtgtccggac gagtctaggc | 780 |
| gagcaggtca tcgtcccccc ctcagaattg gagaggtgtc ctggtgcgcc ttcagtctgt | 840 |
| gacattcagc tgaaccaggt gtcgcctgct gacttcactg tcctcagtga tgtgctgcca | 900 |

```
atgttcagcg tggacttcag caagcaagtc agcagctcgg cagcgtgcca tagcaggcag    960
tttgtacctt tggcgtctgg ccaagcacag gtggttctgt cctggtggga cattgaaatg   1020
gaccctgagg gcaagatcaa gtgcaccatg gcacccttttt gggcacagac agatccgcag   1080
gagcttcagt ggcgggacca ctggatgcag tgtgtgtact tcctgccgca ggaggagcct   1140
gttgtgcagg gctcaccccg gtgcctggta gcccaccatg atgactactg tgtgtggtac   1200
agccttcaga gaaccagccc tgatgagaac gacagcgcct accaagtgcg acctgtgtgt   1260
gactgtcagg ctcacttgct ctggaaccgg cctcggtttg agaaatcaa tgatcaggac   1320
agaactgatc actatgccca ggccctgagg actgtgctgc tgccaggtag cgtctgcctt   1380
tgtgtgagtg atggcagtct cctctccatg ctggcccatc acctcggagc ggagcaggtg   1440
tttacagttg agagttcagt agcttcctat agactgatga aaaggatctt caagttaac   1500
cacttggaag ataaaatcag tgtcatcaat aaacggcctg agttgctgac agctgcagac   1560
ctggagggca agaaggtctc cctcctcctg ggtgaaccct ttttcaccac cagcctgctg   1620
ccatggcaca acctgtactt ctggtatgtc cgtacctctg tggaccagca cctagcacct   1680
ggagctgtgg tgatgcctca ggctgcctca ctgcatgccg tgattgtgga gttcagggac   1740
ctgtggcgga tccggagtcc ttgcggtgac tgcgaaggtt ttgatgtgca catcatggat   1800
gatatgatca gcactccct ggatttccga gagagcagag aggcagagcc acccactg    1860
tgggaatacc cctgcagaag cctctccaag cctcaagaga tcctgacttt tgatttccag   1920
cagcccatcc cccaacagcc tatgcaatcc aagggcacaa tggagctgac aagacccggg   1980
aagagccatg gggctgtcct gtggatggag tatcagctca ctccagacag cacgatcagc   2040
actggcctca taaaccctgc agaagacaag ggggactgct gctggaaccc ccactgcaag   2100
caagctgtgt acttcctcag caccacgctg gatctcagag tgcctctgaa tggccctcgg   2160
tcagtcagct atgttgtgga gtttcaccc ctcactggag acatcaccat ggagtttagg   2220
cttgcagaca ccttgagctg atctcttatt gagaaataaa atggccagca ggctgcagac   2280
```

<210> SEQ ID NO 35
<211> LENGTH: 692
<212> TYPE: PRT
<213> ORGANISM: Mus sp.

<400> SEQUENCE: 35

```
Met Lys Val Phe Cys Gly Arg Ala Asn Pro Thr Thr Gly Ser Leu Glu
1               5                   10                  15

Trp Leu Glu Glu Asp Glu His Tyr Asp Tyr His Gln Glu Ile Ala Arg
            20                  25                  30

Ser Ser Tyr Ala Asp Met Leu His Asp Lys Asp Arg Asn Ile Lys Tyr
        35                  40                  45

Tyr Gln Gly Ile Arg Ala Ala Val Ser Arg Val Lys Asp Arg Gly Gln
    50                  55                  60

Lys Ala Leu Val Leu Asp Ile Gly Thr Gly Thr Gly Leu Leu Ser Met
65                  70                  75                  80

Met Ala Val Thr Ala Gly Ala Asp Phe Cys Tyr Ala Ile Glu Val Phe
                85                  90                  95

Lys Pro Met Ala Glu Ala Ala Val Lys Ile Val Glu Arg Asn Gly Phe
            100                 105                 110

Ser Asp Lys Ile Lys Val Ile Asn Lys His Ser Thr Glu Val Thr Val
        115                 120                 125

Gly Pro Asp Gly Asp Leu Pro Cys Arg Ala Asn Ile Leu Ile Thr Glu
```

```
                130                 135                 140
Leu Phe Asp Thr Glu Leu Ile Gly Glu Gly Ala Leu Pro Ser Tyr Glu
145                 150                 155                 160

His Ala His Lys His Leu Val Gln Glu Asp Cys Glu Ala Val Pro His
                165                 170                 175

Arg Ala Thr Val Tyr Ala Gln Leu Val Glu Ser Arg Met Trp Ser
                180                 185                 190

Trp Asn Lys Leu Phe Pro Val Arg Val Arg Thr Ser Leu Gly Glu Gln
                195                 200                 205

Val Ile Val Pro Pro Ser Glu Leu Glu Arg Cys Pro Gly Ala Pro Ser
210                 215                 220

Val Cys Asp Ile Gln Leu Asn Gln Val Ser Pro Ala Asp Phe Thr Val
225                 230                 235                 240

Leu Ser Asp Val Leu Pro Met Phe Ser Val Asp Phe Ser Lys Gln Val
                245                 250                 255

Ser Ser Ser Ala Ala Cys His Ser Arg Gln Phe Val Pro Leu Ala Ser
                260                 265                 270

Gly Gln Ala Gln Val Val Leu Ser Trp Trp Asp Ile Glu Met Asp Pro
                275                 280                 285

Glu Gly Lys Ile Lys Cys Thr Met Ala Pro Phe Trp Ala Gln Thr Asp
290                 295                 300

Pro Gln Glu Leu Gln Trp Arg Asp His Trp Met Gln Cys Val Tyr Phe
305                 310                 315                 320

Leu Pro Gln Glu Glu Pro Val Val Gln Gly Ser Pro Arg Cys Leu Val
                325                 330                 335

Ala His His Asp Asp Tyr Cys Val Trp Tyr Ser Leu Gln Arg Thr Ser
                340                 345                 350

Pro Asp Glu Asn Asp Ser Ala Tyr Gln Val Arg Pro Val Cys Asp Cys
                355                 360                 365

Gln Ala His Leu Leu Trp Asn Arg Pro Arg Phe Gly Glu Ile Asn Asp
                370                 375                 380

Gln Asp Arg Thr Asp His Tyr Ala Gln Ala Leu Arg Thr Val Leu Leu
385                 390                 395                 400

Pro Gly Ser Val Cys Leu Cys Val Ser Asp Gly Ser Leu Leu Ser Met
                405                 410                 415

Leu Ala His His Leu Gly Ala Glu Gln Val Phe Thr Val Glu Ser Ser
                420                 425                 430

Val Ala Ser Tyr Arg Leu Met Lys Arg Ile Phe Lys Val Asn His Leu
                435                 440                 445

Glu Asp Lys Ile Ser Val Ile Asn Lys Arg Pro Glu Leu Leu Thr Ala
450                 455                 460

Ala Asp Leu Glu Gly Lys Lys Val Ser Leu Leu Gly Glu Pro Phe
465                 470                 475                 480

Phe Thr Thr Ser Leu Leu Pro Trp His Asn Leu Tyr Phe Trp Tyr Val
                485                 490                 495

Arg Thr Ser Val Asp Gln His Leu Ala Pro Gly Ala Val Met Pro
                500                 505                 510

Gln Ala Ala Ser Leu His Ala Val Ile Val Glu Phe Arg Asp Leu Trp
                515                 520                 525

Arg Ile Arg Ser Pro Cys Gly Asp Cys Glu Gly Phe Asp Val His Ile
                530                 535                 540

Met Asp Asp Met Ile Lys His Ser Leu Asp Phe Arg Glu Ser Arg Glu
545                 550                 555                 560
```

```
Ala Glu Pro His Pro Leu Trp Glu Tyr Pro Cys Arg Ser Leu Ser Lys
            565             570             575

Pro Gln Glu Ile Leu Thr Phe Asp Phe Gln Gln Pro Ile Pro Gln Gln
            580             585             590

Pro Met Gln Ser Lys Gly Thr Met Glu Leu Thr Arg Pro Gly Lys Ser
        595             600             605

His Gly Ala Val Leu Trp Met Glu Tyr Gln Leu Thr Pro Asp Ser Thr
        610             615             620

Ile Ser Thr Gly Leu Ile Asn Pro Ala Glu Asp Lys Gly Asp Cys Cys
625             630             635             640

Trp Asn Pro His Cys Lys Gln Ala Val Tyr Phe Leu Ser Thr Thr Leu
            645             650             655

Asp Leu Arg Val Pro Leu Asn Gly Pro Arg Ser Val Ser Tyr Val Val
            660             665             670

Glu Phe His Pro Leu Thr Gly Asp Ile Thr Met Glu Phe Arg Leu Ala
            675             680             685

Asp Thr Leu Ser
            690
```